US008685914B2

(12) United States Patent
Hashimoto et al.

(10) Patent No.: US 8,685,914 B2
(45) Date of Patent: Apr. 1, 2014

(54) L-ALANYL-L-GLUTAMINE CRYSTAL

(75) Inventors: Shin-ichi Hashimoto, Hofu (JP); Kazuhiko Tabata, Tokyo (JP); Shizuo Tsuchiya, Hofu (JP); Tetsuo Nishimura, Hofu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 501 days.

(21) Appl. No.: 11/909,313

(22) PCT Filed: Mar. 29, 2006

(86) PCT No.: PCT/JP2006/306421
§ 371 (c)(1),
(2), (4) Date: Sep. 21, 2007

(87) PCT Pub. No.: WO2006/104186
PCT Pub. Date: Oct. 5, 2006

(65) Prior Publication Data
US 2009/0130708 A1    May 21, 2009

(30) Foreign Application Priority Data
Mar. 29, 2005   (JP) ................. 2005-095103

(51) Int. Cl.
A61K 38/00 (2006.01)
A23J 1/00 (2006.01)

(52) U.S. Cl.
USPC ............................. 514/1.1; 514/5.5; 426/656

(58) Field of Classification Search
None
See application file for complete search history.

(56) References Cited

U.S. PATENT DOCUMENTS

| 5,032,675 A | 7/1991 | Kato et al. |
| 5,380,934 A | 1/1995 | Inoue et al. |
| 5,550,283 A | 8/1996 | Inoue et al. |
| 2004/0137558 A1 | 7/2004 | Yokozeki et al. |
| 2004/0171106 A1 | 9/2004 | Hashimoto et al. |
| 2004/0253665 A1 | 12/2004 | Yokozeki et al. |
| 2005/0037453 A1 | 2/2005 | Tonouchi et al. |
| 2005/0054067 A1 | 3/2005 | Nozaki et al. |
| 2005/0287627 A1* | 12/2005 | Hashimoto et al. .......... 435/68.1 |

FOREIGN PATENT DOCUMENTS

| JP | 06-234715 | 8/1994 |
| WO | 2004/022733 | 3/2004 |

OTHER PUBLICATIONS

Tabata et al., "Fermentative Production of L-Alanyl-L-Glutamine by a Metabolically Engineered *Escherichia coli* Strain Expressing L-Amino Acid α-Ligase", Appl. Environmen. Microbiol. 73:6378-6385, 2007.*
Tabata et al., "ywfE in *Bacillus subtilis* Codes for a Novel Enzyme, L-Amino Acid Ligase", J. Bacteriol. 187:5195-5202, 2005.*
Umbarger, H. E., "Amino Acid Biosynthesis and Its Regulation", Ann. Rev. Biochem. 47:533-606, 1978.*
Akabori, et al., "Protection of Amide-Nitrogen for Peptide Synthesis. A Novel Synthesis of Peptides Containing C-Terminal Glutamine", Bull. Chem. Soc., vol. 34 (1961) 739.
Shimonishi, et al., "Studies on the Synthesis of Peptides Containing Glutamine as the C-Terminal. I. Protection of Amide-nitrogen . . . ", Bull. Chem. Soc., vol. 35, No. 12 (1962) 1966-70.
Sano, et al., "Process Research and Development of L-Alanyl-L-glutamine, a Component of Parenteral Nutrition", Organic Process Research & Dev., vol. 4, No. 3 (2000) 147-52.
Sigma-Aldrich, Safety Data Sheet (2012) A7627.
EVONIK, GPS Safety Summary (2011) L-Alanyl-L-glutamine.

* cited by examiner

*Primary Examiner* — David J Steadman
(74) *Attorney, Agent, or Firm* — Fitzpatrick, Cella, Harper & Scinto

(57) ABSTRACT

The present invention provides: (1) crystals of a dipeptide which do not substantially comprise a dipeptide comprising D-amino acid as a constituent or a polypeptide consisting of three or more amino acids; and (2) crystals of a dipeptide which do not substantially comprise a dipeptide comprising D-amino acid as a constituent, a polypeptide consisting of three or more amino acids, or an amino acid amide; and a process for producing the dipeptide crystals.

1 Claim, No Drawings

US 8,685,914 B2

L-ALANYL-L-GLUTAMINE CRYSTAL

TECHNICAL FIELD

The present invention relates to a dipeptide crystal and a process for production thereof.

BACKGROUND ART

In general, it is required to remove as much impurities, particularly artificial compounds, as possible from compounds to be taken into the human body such as pharmaceuticals. According to the bulk pharmaceuticals guideline by International Conference on Harmonisation of Technical Requirements for Registration of Pharmaceuticals for Human Use (ICH), for example, the weight percent of impurities is to be 0.05% or less. L-Alanyl-L-glutamine is a dipeptide used as a pharmaceutical material (e.g., a component of an infusion preparation) and in cosmetics, and when used as a pharmaceutical material or the like, the above standard is applied.

Known examples of processes for producing dipeptides by the chemical synthesis method, for example, processes for producing L-alanyl-L-glutamine, include a process which comprises condensing N-benzyloxycarbonylalanine with a protective group-added glutamine and then removing the protective group (non-patent document Nos. 1 and 2), a process which comprises condensing N-benzyloxycarbonylalanine with glutamine without a protective group and then removing the protective group (patent document No. 1) and a process which comprises subjecting an N-(2-substituted)-propionyl-glutamine derivative to reaction with ammonia (patent document No. 2 and non-patent document No. 3).

Known examples of processes for producing dipeptides which do not comprise D-amino acid as a constituent using an enzyme or a microorganism include a process which comprises subjecting L-amino acid amide and L-amino acid to the action of L-amino acid amidohydrolase (patent document No. 3), a process which comprises subjecting L-amino acid ester and L-amino acid to the action of various microorganisms (patent document No. 4), a process which comprises subjecting L-amino acid ester and L-amino acid to the action of proline iminopeptidase (patent document No. 5), a process which comprises subjecting L-amino acid ester or L-amino acid amide and L-amino acid to the action of an enzyme derived from bacteria belonging to the genus *Empedobacter* or *Sphingobacterium* (patent document No. 6), and a process using a protein having the activity to form a dipeptide from one or more kinds of amino acids (patent document No. 7).

Of these processes, the chemical synthesis method tends to involve isomerization of an amino group and production of tripeptides as by-products. For example, according to non-patent document No. 3, crystals of L-alanyl-L-glutamine obtained by repeating recrystallization contained 0.19% D-alanyl-L-glutamine. It is suggested that the enzymatic synthesis method using amino acid ester and amino acid amide as starting materials may possibly form polypeptides consisting of three or more amino acids (patent document No. 6).

There exists, therefore, a demand for dipeptide crystals which do not contain impurities such as a dipeptide comprising D-amino acid as a constituent and a polypeptide consisting of three or more amino acids, and a process for production thereof.

Non-Patent Document No. 1:
Bull. Chem. Soc. Jpn., 34, 739 (1961)
Non-Patent Document No. 2:
Bull. Chem. Soc. Jpn., 35, 1966 (1962)
Non-Patent Document No. 3:
Org. Process Res. Dev., 4, 147 (2000)
Patent Document No. 1:
U.S. Pat. No. 5,032,675
Patent Document No. 2
Japanese Published Unexamined Patent Application No. 234715/94
Patent Document No. 3
WO03/010187 pamphlet
Patent Document No. 4
WO03/010189 pamphlet
Patent Document No. 5
WO03/010307 pamphlet
Patent Document No. 6
WO04/022733 pamphlet
Patent Document No. 7
WO04/058960 pamphlet

DISCLOSURE OF THE INVENTION

Problems to be Solved by the Invention

An object of the present invention is to provide crystals of a dipeptide which do not substantially comprise a dipeptide comprising D-amino acid as a constituent or a tripeptide, and a process for production thereof.

Means for Solving the Problems

The present invention relates to the following (1) to (11).
(1) A crystal of a dipeptide which does not substantially comprise a dipeptide comprising D-amino acid as a constituent or a polypeptide consisting of three or more amino acids.
(2) A crystal of L-alanyl-L-glutamine which does not substantially comprise a dipeptide comprising D-amino acid as a constituent or a polypeptide consisting of three or more amino acids.
(3) The crystal according to the above (2), wherein the dipeptide comprising D-amino acid as a constituent is D-alanyl-L-glutamine, and the polypeptide consisting of three or more amino acids is alanyl-alanyl-glutamine.
(4) The crystal according to any one of the above (1) to (3), which does not substantially comprise an amino acid amide.
(5) The crystal according to the above (4), wherein the amino acid amide is alanine amide.
(6) A process for producing the crystal according to any one of the above (1) to (5), which comprises the steps of: culturing in a medium a microorganism which has the ability to produce one or more kinds of amino acids selected from the group consisting of L-amino acids and glycine and which has the ability to produce a protein having the activity to form a dipeptide from one or more kinds of amino acids selected from the group consisting of L-amino acids and glycine; and allowing the dipeptide to form and accumulate in the medium.
(7) The process according to the above (6), wherein the protein having the activity to form a dipeptide from one or more kinds of amino acids selected from the group consisting of L-amino acids and glycine is a protein selected from the group consisting of the following [1] to [4]:
[1] a protein having the amino acid sequence of any of SEQ ID NOS: 1 to 8;
[2] a protein consisting of an amino acid sequence which has 65% or more homology to the amino acid sequence of any of SEQ ID NOS: 1 to 8 and having the activity to form a dipeptide;

[3] a protein consisting of an amino acid sequence wherein one or more amino acid residues are deleted, substituted or added in the amino acid sequence of any of SEQ ID NOS: 1 to 8 and having the activity to form a dipeptide; and

[4] a protein comprising an amino acid sequence which has 80% or more homology to the amino acid sequence of SEQ ID NO: 18 and having the activity to form a dipeptide.

(8) The process according to the above (6) or (7), wherein the one or more kinds of amino acids selected from the group consisting of L-amino acids and glycine are L-alanine or L-glutamine, and the dipeptide is L-alanyl-L-glutamine.

(9) A process for producing the crystal according to any one of the above (2) to (5), which comprises: culturing in a medium a microorganism which has the ability to produce L-alanine or L-glutamine and which has the ability to produce a protein having the activity to form L-alanyl-L-glutamine from L-alanine and L-glutamine; allowing L-alanyl-L-glutamine to form and accumulate in the culture; and then carrying out the step of the following [1] or [2]:

[1] heating the culture comprising L-alanyl-L-glutamine or a solution comprising L-alanyl-L-glutamine prepared from the culture; and

[2] preparing a solution comprising L-alanyl-L-glutamine from the culture comprising L-alanyl-L-glutamine and adding methanol to the resulting solution to obtain crystals of L-alanyl-L-glutamine.

(10) A process for producing the crystal according to any one of the above (2) to (5), which comprises:

allowing an enzyme source, L-alanine and L-glutamine to be present in an aqueous medium, said enzyme source being a protein having the activity to form L-alanyl-L-glutamine from L-alanine and L-glutamine, a culture of a microorganism having the ability to produce the protein, or a treated matter of the culture; allowing L-alanyl-L-glutamine to form and accumulate in the aqueous medium; preparing a solution comprising L-alanyl-L-glutamine from the aqueous medium; and adding methanol to the solution to obtain crystals of L-alanyl-L-glutamine.

(11) The process according to the above (10), wherein the protein having the activity to form L-alanyl-L-glutamine from L-alanine and L-glutamine is a protein selected from the group consisting of the following [1] to [4]:

[1] a protein having the amino acid sequence of any of SEQ ID NOS: 1 to 8;

[2] a protein consisting of an amino acid sequence which has 65% or more homology to the amino acid sequence of any of SEQ ID NOS: 1 to 8 and having the activity to form L-alanyl-L-glutamine;

[3] a protein consisting of an amino acid sequence wherein one or more amino acid residues are deleted, substituted or added in the amino acid sequence of any of SEQ ID NOS: 1 to 8 and having the activity to form L-alanyl-L-glutamine; and

[4] a protein comprising an amino acid sequence which has 80% or more homology to the amino acid sequence of SEQ ID NO: 18 and having the activity to form L-alanyl-L-glutamine.

Effect of the Invention

In accordance with the present invention, a crystal of a dipeptide which does not substantially comprise a dipeptide comprising D-amino acid as a constituent or a polypeptide consisting of three or more amino acids can be produced.

BEST MODES FOR CARRYING OUT THE INVENTION

1. Dipeptide Crystals of the Present Invention

The dipeptide crystals of the present invention which do not substantially comprise a dipeptide comprising D-amino acid as a constituent or a polypeptide consisting of three or more amino acids include dipeptide crystals which do not substantially comprise one or more kinds of dipeptides comprising D-form of amino acids which constitute the desired dipeptide crystals, or one or more kinds of polypeptides consisting of three or more amino acids, preferably one or more kinds of tripeptides, which comprise amino acids which constitute the desired dipeptide crystals and/or D-form of the amino acids.

In the present invention, examples of the dipeptides comprising D-amino acid as a constituent are dipeptides comprising, as a constituent, D-amino acid selected from the group consisting of D-alanine (D-Ala), D-glutamine (D-Gln), D-glutamic acid (D-Glu), D-valine (D-Val), D-leucine (D-Leu), D-isoleucine (D-Ile), D proline (D-Pro), D-phenylalanine (D-Phe), D-tryptophan (D-Trp), D-methionine (D-Met), D-serine (D-Ser), D-threonine (D-Thr), D-cysteine (D-Cys), D-asparagine (D-Asn), D-tyrosine (D-Tyr), D-lysine (D-Lys), D-arginine (D-Arg), D-histidine (D-His), D-aspartic acid (D-Asp), D-α-aminobutyric acid (D-α-AB), D-Azaserine, D-theanine, 4-hydroxy-D-proline (4-D-HYP), 3-hydroxy-D-proline (3-D-HYP), D-ornithine (D-Orn), D-citrulline (D-Cit) and 6-diazo-5-oxo-D-norleucine.

In the present invention, examples of the polypeptides consisting of three or more amino acids are polypeptides consisting of three or more amino acids selected from the group consisting of alanine (Ala), glutamine (Gln), glutamic acid (Glu), valine (Val), leucine (Leu), isoleucine (Ile), proline (Pro), phenylalanine (Phe), tryptophan (Trp), methionine (Met), serine (Ser), threonine (Thr), cysteine (Cys), asparagine (Asn), tyrosine (Tyr), lysine (Lys), arginine (Arg), histidine (His), aspartic acid (Asp), α-aminobutyric acid (α-AB), Azaserine, theanine, 4-hydroxyproline (4-HYP), 3-hydroxyproline (3-HYP), ornithine (Orn), citrulline (Cit), D-6-diazo-5-oxo-norleucine, glycine (Gly) and β-alanine (β-Ala), preferably tripeptides.

The dipeptide crystals of the present invention which do not substantially comprise a dipeptide comprising D-amino acid as a constituent or a polypeptide consisting of three or more amino acids include any dipeptide crystals that do not substantially comprise the above dipeptides comprising D-amino acid as a constituent or polypeptides consisting of three or more amino acids, but are preferably crystals of a dipeptide consisting of one or two kinds of amino acids selected from the group consisting of L-alanine (L-Ala), L-glutamine (L-Gln), L-glutamic acid (L-Glu), L-valine (L-Val), L-leucine (L-Leu), L-isoleucine (L-Ile), L-proline (L-Pro), L-phenylalanine (L-Phe), L-tryptophan (L-Trp), L-methionine (L-Met), L-serine (L-Ser), L-threonine (L-Thr), L-cysteine (L-Cys), L-asparagine (L-Asn), L-tyrosine (L-Tyr), L-lysine (L-Lys), L-arginine (L-Arg), L-histidine (L-His), L-aspartic acid (L-Asp), L-α-aminobutyric acid (L-α-AB), L-Azaserine, L-theanine, 4-hydroxy-L-proline (4-L-HYP), 3-hydroxy-L-proline (3-L-HYP), L-ornithine (L-Orn), L-citrulline (L-Cit), 6-diazo-5-oxo-L-norleucine), Gly and β-Ala.

Preferred dipeptide crystals of the present invention include crystals of a dipeptide represented by formula (I):

$$R^1\text{-}R^2 \qquad (I)$$

(wherein $R^1$ is L-Ala, L-Met, L-Ser, L-Thr or β-Ala; and $R^2$ is L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, 4-L-HYP, 3-L-HYP, L-Orn, L-Cit or Gly) which do not substantially comprise, as a dipeptide comprising D-amino acid as a constituent, one or more kinds of dipeptides comprising D-amino acid selected from the group consisting of D-Ala, D-Met, D-Ser, D-Thr, D-Gln, D-Glu, D-Val, D-Leu, D-Ile, D-Pro, D-Phe, D-Trp, D-Cys, D-Asn, D-Tyr, D-Lys, D-Arg, D-His, D-Asp, D-α-AB, 4-D-HYP, 3-D-HYP, D-Orn and D-Cit, or as a polypeptide consisting of three or more amino acids, one or more kinds of polypeptides consisting of three or more amino acids, preferably one or more kinds of tripeptides, which comprise amino acid selected from the group consisting of Ala, Met, Ser, Thr, Gln, Glu, Val, Leu, Ile, Pro, Phe, Trp, Cys, Asn, Tyr, Lys, Arg, His, Asp, α-AB, 4-HYP, 3-HYP, Orn, Cit, Gly and β-Ala. More preferred dipeptide crystals of the present invention include crystals of a dipeptide represented by formula (II):

$$R^3\text{-}R^4 \qquad (II)$$

(wherein when $R^3$ is L-Ala, $R^4$ is L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB or L-Cit; when $R^3$ is Gly, $R^4$ is L-Gln, Gly, L-Phe, L-Trp, L-Met, L-Ser, L-Thr, L-Cys, L-Tyr, L-Lys, L-Arg, L-α-AB or L-Cit; when $R^3$ is L-Met, $R^4$ is L-Phe, L-Met, L-Cys, L-Tyr, L-Lys or L-His; when $R^3$ is L-Ser, $R^4$ is L-Gln, Gly, L-Phe, L-Met, L-Ser, L-Thr, L-Tyr, L-His or L-α-AB; when $R^3$ is L-Thr, $R^4$ is L-Gln, L-Leu, L-Phe, L-Met, L-Ser, L-Thr or L-α-AB; when $R^3$ is L-Gln, $R^4$ is L-Phe or L-α-AB; when $R^3$ is L-Phe, $R^4$ is L-Gln; when $R^3$ is L-Trp, $R^4$ is Gly; when $R^3$ is L-Cys, $R^4$ is L-Ala, L-Gln, Gly or L-Met; when $R^3$ is L-Lys, $R^4$ is L-Ala, Gly or L-Met; when $R^3$ is L-Arg, $R^4$ is L-α-AB; when $R^3$ is L-His, $R^4$ is L-Met; when $R^3$ is L-α-AB, $R^4$ is L-Ala, L-Gln, Gly, L-Ser, L-Thr, L-Arg or L-α-AB; and when $R^3$ is β-Ala, $R^4$ is L-His) which do not substantially comprise, as a dipeptide comprising D-amino acid as a constituent, one or more kinds of dipeptides comprising D-amino acid selected from the group consisting of D-Ala, D-Gln, D-Val, D-Leu, D-Ile, D-Phe, D-Trp, D-Met, D-Ser, D-Thr, D-Cys, D-Asn, D-Tyr, D-Lys, D-Arg, D-His, D-α-AB and D-Cit, or as a polypeptide consisting of three or more amino acids, one or more kinds of polypeptides consisting of three or more amino acids, preferably one or more kinds of tripeptides, which comprise amino acid selected from the group consisting of Ala, Gln, Val, Leu, Ile, Phe, Trp, Met, Ser, Thr, Cys, Asn, Tyr, Lys, Arg, His, α-AB, Cit, Gly and β-Ala.

Further preferred dipeptide crystals of the present invention include crystals of a dipeptide represented by formula (II) (wherein $R^3$ and $R^4$ respectively have the same significances as defined above) which do not substantially comprise, as a dipeptide comprising D-amino acid as a constituent, a dipeptide in which the carboxyl group of D-amino acid selected from the group consisting of D-Ala, D-Gln, D-Val, D-Leu, D-Ile, D-Phe, D-Trp, D-Met, D-Ser, D-Thr, D-Cys, D-Asn, D-Tyr, D-Lys, D-Arg, D-His, D-α-AB and D-Cit and the amino group of L-amino acid selected from the group consisting of L-Ala, L-Gln, L-Val, L-Leu, L-Ile, L-Phe, L-Trp, L-Met, L-Ser, L-Thr, L-Cys, L-Asn, L-Tyr, L-Lys, L-Arg, L-His, L-α-AB and L-Cit are linked by a peptide bond, or as a polypeptide consisting of three or more amino acids, one or more kinds of polypeptides consisting of three or more amino acids, preferably one or more kinds of tripeptides, which comprise amino acid selected from the group consisting of L-Ala, L-Gln, L-Val, L-Leu, L-Ile, L-Phe, L-Trp, L-Met, L-Ser, L-Thr, L-Cys, L-Asn, L-Tyr, L-Lys, L-Arg, L-His, L-α-AB, L-Cit, Gly and β-Ala.

A particularly preferred example of the dipeptide crystals of the present invention is L-alanyl-L-glutamine crystals which do not substantially comprise D-Ala-L-Gln as a dipeptide comprising D-amino acid as a constituent, or alanyl-alanyl-glutamine (Ala-Ala-Gln) as a polypeptide consisting of three or more amino acids.

The dipeptide crystals of the present invention which do not substantially comprise a dipeptide comprising D-amino acid as a constituent or a polypeptide consisting of three or more amino acids also include crystals which further do not substantially comprise an amino acid amide, in addition to the above crystals. Examples of the amino acid amides include alanine amide ($AlaNH_2$), glycine amide and aspartic acid-α-amide, and preferred is $AlaNH_2$.

A preferred example of the dipeptide crystals of the present invention is L-alanyl-L-glutamine crystals which do not substantially comprise D-Ala-L-Gln as a dipeptide comprising D-amino acid as a constituent, Ala-Ala-Gln as a polypeptide consisting of three or more amino acids, or $AlaNH_2$ as an amino acid amide.

The dipeptide crystals of the present invention may be in any crystal form, for example, needles.

The expression "do not substantially comprise a dipeptide comprising D-amino acid as a constituent or a polypeptide consisting of three or more amino acids" means that their weight percentages in the dipeptide crystals of the present invention are as follows: (a) the weight percentage of a dipeptide comprising D-amino acid as a constituent is 0.05% or less and the weight percentage of a polypeptide consisting of three or more amino acids is less than 0.014%; preferably the weight percentage of a dipeptide comprising D-amino acid as a constituent is 0.05% or less and the weight percentage of a polypeptide consisting of three or more amino acids is 0.010% or less; more preferably the weight percentage of a dipeptide comprising D-amino acid as a constituent is 0.05% or less and the weight percentage of a polypeptide consisting of three or more amino acids is 0.005% or less; and further preferably the weight percentage of a dipeptide comprising D-amino acid as a constituent is 0.05% or less and the weight percentage of a polypeptide consisting of three or more amino acids is 0.002% or less; or the weight percentage of a dipeptide comprising D-amino acid as a constituent is less than 0.004% and the weight percentage of a polypeptide consisting of three or more amino acids is less than 0.032%; preferably the weight percentage of a dipeptide comprising D-amino acid as a constituent is 0.003% or less and the weight percentage of a polypeptide consisting of three or more amino acids is 0.020% or less; more preferably the weight percentage of a dipeptide comprising D-amino acid as a constituent is 0.002% or less and the weight percentage of a polypeptide consisting of three or more amino acids is 0.010% or less; further preferably the weight percentage of a dipeptide comprising D-amino acid as a constituent is 0.002% or less and the weight percentage of a polypeptide consisting of three or more amino acids is 0.005% or less; and particularly preferably the weight percentage of a dipeptide comprising D-amino acid as a constituent is 0.002% or less and the weight percentage of a polypeptide consisting of three or more amino acids is 0.002% or less.

The expression "do not substantially comprise a dipeptide comprising D-amino acid as a constituent, a polypeptide consisting of three or more amino acids or an amino acid amide" means that their weight percentages in the dipeptide crystals are as follows: (b) the weight percentage of a dipeptide comprising D-amino acid as a constituent is less than 0.004%, the weight percentage of a polypeptide consisting of three or more amino acids is less than 0.032% and the weight percentage of an amino acid amide is less than 0.023%; preferably the weight percentage of a dipeptide comprising D-amino acid as a constituent is 0.003% or less, the weight percentage of a polypeptide consisting of three or more amino acids is 0.020% or less and the weight percentage of an amino acid amide is 0.015% or less; more preferably the weight percentage of a dipeptide comprising D-amino acid as a constituent is 0.002% or less, the weight percentage of a polypeptide consisting of three or more amino acids is 0.010% or less and the weight percentage of an amino acid amide is 0.012% or less; and further preferably the weight percentage of a dipeptide comprising D-amino acid as a constituent is 0.002% or less, the weight percentage of a polypeptide consisting of three or more amino acids is 0.002% or less and the weight percentage of an amino acid amide is 0.009% or less.

The expression "do not substantially comprise a dipeptide comprising D-amino acid as a constituent or a polypeptide consisting of three or more amino acids" alternatively means that their area percentages to the total peak area of the dipeptide crystals of the present invention as analyzed by HPLC are as follows: (c) the area percentage of a dipeptide comprising D-amino acid as a constituent is 0.05% or less and the area percentage of a polypeptide consisting of three or more amino acids is less than 0.018%; preferably the area percentage of a dipeptide comprising D-amino acid as a constituent is 0.05% or less and the area percentage of a polypeptide consisting of three or more amino acids is 0.013% or less; more preferably the area percentage of a dipeptide comprising D-amino acid as a constituent is 0.05% or less and the area percentage of a polypeptide consisting of three or more amino acids is 0.006% or less; and further preferably the area percentage of a dipeptide comprising D-amino acid as a constituent is 0.05% or less and the area percentage of a polypeptide consisting of three or more amino acids is 0.003% or less; or the area percentage of a dipeptide comprising D-amino acid as a constituent is 0.004% or less and the area percentage of a polypeptide consisting of three or more amino acids is less than 0.032%; preferably the area percentage of a dipeptide comprising D-amino acid as a constituent is 0.003% or less and the area percentage of a polypeptide consisting of three or more amino acids is 0.026% or less; more preferably the area percentage of a dipeptide comprising D-amino acid as a constituent is 0.002% or less and the area percentage of a polypeptide consisting of three or more amino acids is 0.018% or less; and further preferably the area percentage of a dipeptide comprising D-amino acid as a constituent is 0.002% or less and the area percentage of a polypeptide consisting of three or more amino acids is 0.013% or less.

The expression "do not substantially comprise a dipeptide comprising D-amino acid as a constituent, a polypeptide consisting of three or more amino acids or an amino acid amide" alternatively means that their area percentages to the total peak area of the dipeptide crystals as analyzed by HPLC are as follows: (d) the area percentage of a dipeptide comprising D-amino acid as a constituent is less than 0.004%, the area percentage of a polypeptide consisting of three or more amino acids is less than 0.041% and the area percentage of an amino acid amide is less than 0.005%; preferably the area percentage of a dipeptide comprising D-amino acid as a constituent is 0.003% or less, the area percentage of a polypeptide consisting of three or more amino acids is 0.026% or less and the area percentage of an amino acid amide is 0.003% or less; more preferably the area percentage of a dipeptide comprising D-amino acid as a constituent is 0.002% or less, the area percentage of a polypeptide consisting of three or more amino acids is 0.013% or less and the area percentage of an amino acid amide is 0.003% or less; and further preferably the area percentage of a dipeptide comprising D-amino acid as a constituent is 0.002% or less, the area percentage of a polypeptide consisting of three or more amino acids is 0.002% or less and the area percentage of an amino acid amide is 0.002% or less.

The dipeptide crystals of the present invention also include dipeptide crystals which do not substantially comprise a dipeptide comprising D-amino acid as a constituent or a polypeptide consisting of three or more amino acids and in which the area percentage or weight percentage of dipeptide to the total dipeptide crystals is preferably 99.90% or more, more preferably 99.91% or more, further preferably 99.92% or more, and dipeptide crystals which do not substantially comprise a dipeptide comprising D-amino acid as a constituent, a polypeptide consisting of three or more amino acids or an amino acid amide and in which the area percentage or weight percentage is preferably 99.90% or more, more preferably 99.91% or more, further preferably 99.92% or more.

The method for measuring the weight percentage of a dipeptide comprising D-amino acid as a constituent, a polypeptide consisting of three or more amino acids and an amino acid amide contained in the dipeptide crystals of the present invention and that of the dipeptide crystals of the present invention may be any method that can measure the amount of each of the above components. For example, the measurement is preferably made by separating components contained in the dipeptide crystals of the present invention by HPLC, etc., and calculating the amount of each component from its peak area based on the peak area and amount of a standard product.

The area percentage of a dipeptide comprising D-amino acid as a constituent, a polypeptide consisting of three or more amino acids and an amino acid amide contained in the dipeptide crystals of the present invention to the total peak area of the dipeptide crystals of the present invention can be determined by separating the above components by HPLC, and calculating the peak area of each component to the total peak area of the dipeptide crystals of the present invention.

The conditions for HPLC analysis are, for example, as follows.

Analysis Conditions:
    Column: Inertsil ODS-3V (GL Sciences Inc.)
    Column temperature: 30° C.
    Mobil phase: Solution A [0.01 mol/l sodium heptanesulfonate, 0.01 mol/l potassium dihydrogenphosphate (pH 2.5)]: methanol=99:1
    Flow rate: 1.2 ml/min
    Detection: UV 210 nm
    Modification of the conditions, such as change of the solution composition of mobile phase, use of a concentration gradient of plural solutions and change of a detection wavelength, can be appropriately made according to the kind of a dipeptide comprising D-amino acid as a constituent, a polypeptide consisting of three or more amino acids and an amino acid amide contained in the dipeptide sample subjected to analysis. A method which comprises derivatizing a substance in a sample with FMOC (fluorenylmethyl chloroformate) and detecting its emission can also be used.

2. Process for Production of the Dipeptide Crystals of the Present Invention

The crystals of the present invention can be produced by i) a process which comprises allowing an enzyme source and one or more kinds of amino acids selected from the group consisting of L-amino acids, glycine and β-alanine to be present in an aqueous medium, said enzyme source being a protein having the activity to form a dipeptide from one or more kinds of amino acids selected from the group consisting of L-amino acids, glycine and β-alanine, a culture of a microorganism having the ability to produce the protein or a treated culture, allowing the dipeptide to form and accumulate in the aqueous medium, and recovering crystals of the dipeptide from the aqueous medium, ii) a process which comprises culturing in a medium a microorganism which has the ability to form and accumulate one or more kinds of amino acids selected from the group consisting of L-amino acids and glycine and which has the ability to produce a protein having the activity to form a dipeptide from one or more kinds of amino acids selected from the group consisting of L-amino acids and glycine, allowing the dipeptide to form and accumulate in the medium, and recovering crystals of the dipeptide from the medium, and the like.

(1) Proteins Used in the Process of the Present Invention (a) There is no specific restriction as to the protein having the activity to form a dipeptide from one or more kinds of amino acids selected from the group consisting of L-amino acids, glycine and β-alanine used in the process of the present invention as long as it has the activity. Suitable examples of the proteins are those according to the following [1] to [4]:

[1] a protein having the amino acid sequence of any of SEQ ID NOS: 1 to 8;

[2] a protein consisting of an amino acid sequence which has at least 65% homology, preferably 80% or more homology, more preferably 90% or more homology, further preferably 95% or more homology, particularly preferably 98% or more homology, most preferably 99% or more homology to the amino acid sequence of any of SEQ ID NOS: 1 to 8 and having the activity to form a dipeptide;

[3] a protein consisting of an amino acid sequence wherein one or more amino acid residues are deleted, substituted or added in the amino acid sequence of any of SEQ ID NOS: 1 to 8 and having the activity to form a dipeptide; and

[4] a protein comprising an amino acid sequence which has at least 80% homology, preferably 90% or more homology, more preferably 95% or more homology, further preferably 98% or more homology, particularly preferably 99% or more homology to the amino acid sequence of SEQ ID NO: 18 and having the activity to form a dipeptide.

The amino acid sequence of SEQ ID NO: 18 is a region which is conserved among the proteins having the amino acid sequences of SEQ ID NOS: 1 to 7 and which corresponds to the consensus sequence of proteins having Ala-Ala ligase activity derived from various microorganisms.

Therefore, a protein which comprises an amino acid sequence having at least 80% homology, preferably 90% or more homology, more preferably 95% or more homology, further preferably 98% or more homology, particularly preferably 99% or more homology to the amino acid sequence of SEQ ID NO: 18 and which has the activity to form a dipeptide is also a protein having the activity to form a dipeptide.

In order that a protein comprising an amino acid sequence having at least 80% homology, preferably 90% or more homology, more preferably 95% or more homology, further preferably 98% or more homology, particularly preferably 99% or more homology to the amino acid sequence of SEQ ID NO: 18 may have the activity to form a dipeptide, it is desirable that the amino acid sequence of the protein has at least 65% homology, preferably 80% or more homology, more preferably 90% or more homology, further preferably 95% or more homology, particularly preferably 98% or more homology, most preferably 99% or more homology to the amino acid sequence of any of SEQ ID NOS: 1 to 7.

The above protein consisting of an amino acid sequence wherein one or more amino acid residues are deleted, substituted or added and having the activity to form a dipeptide can be obtained, for example, by introducing a site-directed mutation into DNA encoding a protein consisting of the amino acid sequence of any of SEQ ID NOS: 1 to 8 and having the activity to form a dipeptide by site-directed mutagenesis described in Molecular Cloning, A Laboratory Manual, Third Edition, Cold Spring Harbor Laboratory Press (2001) (hereinafter referred to as Molecular Cloning, Third Edition); Current Protocols in Molecular Biology, John Wiley & Sons (1987-1997) (hereinafter referred to as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

The number of amino acid residues which are deleted, substituted or added is not specifically limited so long as it is within the range where deletion, substitution or addition is possible by known methods such as the above site-directed mutagenesis. The suitable number is 1 to dozens, preferably 1 to 20, more preferably 1 to 10, further preferably 1 to 5.

The expression "one or more amino acid residues are deleted, substituted or added in a protein consisting of the amino acid sequence of any of SEQ ID NOS: 1 to 8" means that the amino acid sequence may contain deletion, substitution or addition of a single or plural amino acid residues at an arbitrary position therein.

Deletion, substitution and addition may be simultaneously contained in one sequence, and amino acids to be substituted or added may be either natural or not. Examples of the natural amino acids are L-alanine, L-asparagine, L-aspartic acid, L-glutamine, L-glutamic acid, glycine, L-arginine, L-histidine, L-isoleucine, L-leucine, L-lysine, L-methionine, L-phenylalanine, L-proline, L-serine, L-threonine, L-tryptophan, L-tyrosine, L-valine and L-cysteine.

The following are examples of the amino acids capable of mutual substitution. The amino acids in the same group can be mutually substituted.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine There is no specific restriction as to the position where the deletion, substitution or addition of one or more amino acid residues described above is introduced, so long as a protein having an amino acid sequence carrying the introduced mutation has the activity to form a dipeptide. Examples of the amino acid residues are those that are not conserved in all of the amino acid sequences of SEQ ID NOS: 1 to 8 when the sequences are compared using known alignment software. An example of known alignment software is alignment analysis software contained in gene analysis software Genetyx (Software Development Co., Ltd.). As analysis parameters for the analysis software, default values can be used.

An example of the above protein consisting of an amino acid sequence wherein one or more amino acid residues are deleted, substituted or added and having the activity to form a dipeptide is a protein having at least 65%, preferably 80% or more, more preferably 90% or more, further preferably 95% or more, particularly preferably 98% or more, most preferably 99% or more homology to the amino acid sequence of any of SEQ ID NOS: 1 to 8.

In the above, the homology among amino acid sequences and nucleotide sequences can be determined by using algorithm BLAST by Karlin and Altschul [Pro. Natl. Acad. Sci. USA, 90, 5873 (1993)] and FASTA [Methods Enzymol., 183, 63 (1990)]. On the basis of the algorithm BLAST, programs such as BLASTN and BLASTX have been developed [J. Mol. Biol., 215, 403 (1990)]. When a nucleotide sequence is analyzed by BLASTN on the basis of BLAST, the parameters, for instance, are as follows: score=100 and wordlength=12. When an amino acid sequence is analyzed by BLASTX on the basis of BLAST, the parameters, for instance, are as follows: score=50 and wordlength=3. When BLAST and Gapped BLAST programs are used, default parameters of each program are used. The specific techniques for these analyses are known.

(b) There is no specific restriction as to the protein having the activity to form a dipeptide from one or more kinds of amino acids selected from the group consisting of L-amino acids and glycine of the present invention as long as it has the activity. Suitable examples of the proteins are those according to the following [5] to [8]:

[5] a protein having the amino acid sequence of any of SEQ ID NOS: 1 to 8;
[6] a protein consisting of an amino acid sequence which has at least 65% homology, preferably 80% or more homology, more preferably 90% or more homology, further preferably 95% or more homology, particularly preferably 98% or more homology, most preferably 99% or more homology to the amino acid sequence of any of SEQ ID NOS: 1 to 8 and having the activity to form a dipeptide;
[7] a protein consisting of an amino acid sequence wherein one or more amino acid residues are deleted, substituted or added in the amino acid sequence of any of SEQ ID NOS: 1 to 8 and having the activity to form a dipeptide; and
[8] a protein comprising an amino acid sequence which has at least 80% homology, preferably 90% or more homology, more preferably 95% or more homology, further preferably 98% or more homology, particularly preferably 99% or more homology to the amino acid sequence of SEQ ID NO: 18 and having the activity to form a dipeptide.

The amino acid sequence of SEQ ID NO: 18 is a sequence which has the characteristics described in the above (a).

Therefore, a protein which comprises an amino acid sequence having at least 80% homology, preferably 90% or more homology, more preferably 95% or more homology, further preferably 98% or more homology, particularly preferably 99% or more homology to the amino acid sequence of SEQ ID NO: 18 and which has dipeptide-synthesizing activity is also a protein having the activity to form a dipeptide.

In order that a protein comprising an amino acid sequence having at least 80% homology, preferably 90% or more homology, more preferably 95% or more homology, further preferably 98% or more homology, particularly preferably 99% or more homology to the amino acid sequence shown in SEQ ID NO: 18 may have the activity to form a dipeptide, it is desirable that the amino acid sequence of the protein has at least 65% homology, preferably 80% or more homology, more preferably 90% or more homology, further preferably 95% or more homology, particularly preferably 98% or more homology, most preferably 99% or more homology to the amino acid sequence of any of SEQ ID NOS: 1 to 7.

The above protein consisting of an amino acid sequence wherein one or more amino acid residues are deleted, substituted or added and having the activity to form a dipeptide can be obtained by the method described in Molecular Cloning, Third Edition, etc. in the same manner as in the above (a).

The number of amino acid residues to be deleted, substituted or added is the same as that in the above (a).

The expression "one or more amino acid residues are deleted, substituted or added in a protein consisting of the amino acid sequence of any of SEQ ID NOS: 1 to 8" has the same significance as in the above (a).

Deletion, substitution and addition may be simultaneously contained in one sequence, and amino acids to be substituted or added are the same as those in the above (a).

There is no specific restriction as to the position where the deletion, substitution or addition of one or more amino acid residues described above is introduced, as long as a protein having an amino acid sequence carrying the introduced mutation has the activity to form a dipeptide, and examples of the positions are the same as those in the above (a).

An example of the above protein consisting of an amino acid sequence wherein one or more amino acid residues are deleted, substituted or added and having the activity to form a dipeptide is the same as that in the above (a).

In the above, the homology among amino acid sequences and nucleotide sequences can be determined by using BLAST and FASTA.

(2) Microorganisms Used for Production of the Dipeptide Crystals of the Present Invention (a) There is no specific restriction as to the microorganism which has the ability to produce a protein having the activity to form a dipeptide from one or more kinds of amino acids selected from the group consisting of L-amino acids, glycine and β-alanine of the present invention so long as it is a microorganism having the ability to produce the protein of the above (1)(a). Examples of the microorganisms are those having the ability to produce the protein according to any of [1] to [4] of the above (1)(a).

Examples of the one or more kinds of amino acids selected from the group consisting of L-amino acids, glycine and β-alanine are preferably one or more kinds of amino acids selected from the group consisting of L-Ala, L-Gln, L-Glu, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, L-Azaserine, L-theanine, 4-L-HYP, 3-L-HYP, L-Orn, L-Cit, L-6-diazo-5-oxo-L-norleucine, Gly and β-Ala, more preferably two kinds of amino acids selected from the group consisting of L-Ala, L-Gln, L-Glu, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, 4-L-HYP, 3-L-HYP, L-Orn, L-Cit, Gly and β-Ala, further preferably L-Ala and L-Gln.

Examples of the microorganisms having the ability to produce the protein according to any of [1] to [4] of the above (1)(a) are microorganisms belonging to the genus *Bacillus* which have a bacilysin synthetase gene described in WO2004/058960, preferably, *Bacillus subtilis, Bacillus amyloliquefaciens, Bacillus coagulans, Bacillus licheniformis, Bacillus megaterium* and *Bacillus pumilus*, more preferably, *Bacillus subtilis* 168 (ATCC 23857), *Bacillus subtilis* ATCC 15245, *Bacillus subtilis* ATCC 6633, *Bacillus subtilis* IAM 1213, *Bacillus subtilis* IAM 1107, *Bacillus subtilis* IAM 1214, *Bacillus subtilis* ATCC 9466, *Bacillus subtilis* IAM 1033, *Bacillus subtilis* ATCC 21555, *Bacillus amyloliquefaciens* IFO 3022 and microorganisms transformed with DNA encoding the protein according to any of [1] to [4] of the above (1).

The DNAs encoding the proteins according to [1] to [4] of the above (1) include:

[9] DNA having the nucleotide sequence of any of SEQ ID NOS: 9 to 17;

[10] DNA which hybridizes with DNA having a nucleotide sequence complementary to the nucleotide sequence shown in any of SEQ ID NOS: 9 to 17 under stringent conditions and which encodes a protein having the activity to form a dipeptide; and

[11] DNA comprising a nucleotide sequence which has at least 80% homology, preferably 90% or more homology, more preferably 95% or more homology, further preferably 98% or more homology, particularly preferably 99% or more homology to the nucleotide sequence of SEQ ID NO: 19 and encoding a protein having the activity to form a dipeptide.

"To hybridize" refers to a step of hybridization of DNA with DNA having a specific nucleotide sequence or a part of the DNA. Therefore, the nucleotide sequence of the DNA having a specific nucleotide sequence or a part of the DNA may be DNA which is long enough to be useful as a probe for Northern or Southern blot analysis or to be used as an oligonucleotide primer for PCR analysis. DNAs used as a probe include DNAs consisting of at least 100 nucleotides, preferably 200 or more nucleotides, more preferably 500 or more nucleotides, but may also be DNAs consisting of at least 10 nucleotides, preferably 15 or more nucleotides.

The method for hybridization of DNA is well known and the conditions for hybridization can be determined by a person skilled in the art according to the present specification. The hybridization can be carried out according to the methods described in Molecular Cloning, Second Edition, Third Edition (2001); Methods for General and Molecular Bacteriology, ASM Press (1994); Immunology methods manual, Academic press (Molecular), and many other standard textbooks.

Hybridization under the above stringent conditions is carried out, for example, as follows. A filter with DNA immobilized thereon and a probe DNA are incubated in a solution comprising 50% formamide, 5×SSC (750 mM sodium chloride and 75 mM sodium citrate), 50 mM sodium phosphate (pH 7.6), 5×Denhardt's solution, 10% dextran sulfate and 20 µg/l denatured salmon sperm DNA at 42° C. overnight, and after the incubation, the filter is washed in 0.2×SSC solution (ca. 65° C.). Less stringent conditions can also be employed. Modification of the stringent conditions can be made by adjusting the concentration of formamide (the conditions become less stringent as the concentration of formamide is reduced) and by changing the salt concentrations and the temperature conditions. Hybridization under less stringent conditions is carried out, for example, by incubating a filter with DNA immobilized thereon and a probe DNA in a solution comprising 6×SSCE (20×SSCE: 3 mol/l sodium chloride, 0.2 mol/l sodium dihydrogenphosphate and 0.02 mol/l EDTA, pH 7.4), 0.5% SDS, 30% formamide and 100 µg/l denatured salmon sperm DNA at 37° C. overnight, and washing the filter with 1×SSC solution containing 0.1% SDS (50° C.). Hybridization under still less stringent conditions is carried out by using a solution having a high salt concentration (for example, 5×SSC) under the above less stringent conditions, followed by washing.

Various conditions described above can also be established by adding a blocking reagent used to reduce the background of hybridization or changing the reagent. The addition of the above blocking reagent may be accompanied by changes of conditions for hybridization to make the conditions suitable for the purpose.

The above DNA capable of hybridization under stringent conditions includes DNA having at least 80% homology, preferably 90% or more homology, more preferably 95% or more homology, further preferably 98% or more homology, particularly preferably 99% or more homology to the nucleotide sequence of any of the DNAs described above as calculated by use of programs such as BLAST and FASTA described above based on the above parameters.

The homology among nucleotide sequences can be determined by using programs such as BLAST and FASTA described above.

It is possible to confirm that the DNA which hybridizes with the above DNA under stringent conditions is DNA encoding a protein having the activity to form a dipeptide in the following manner. That is, a recombinant DNA expressing the DNA is prepared, and a microorganism obtained by introducing the recombinant DNA into a host cell as an enzyme source and one or more kinds of amino acids selected from the group consisting of L-amino acids, glycine and β-alanine are allowed to be present in an aqueous medium, followed by HPLC analysis or the like to know whether a dipeptide is formed and accumulated in the aqueous medium.

(b) There is no specific restriction as to the microorganism which has the ability to produce a protein having the activity to form a dipeptide from one or more kinds of amino acids selected from the group consisting of L-amino acids and glycine and has the ability to produce one or more kinds of amino acids selected from the group consisting of L-amino acids and glycine used in the process of the present invention, so long as it is a microorganism having the abilities. Examples of the microorganisms are those having the ability to produce the protein according to any of [5] to [8] of the above (1)(b) and having the ability to produce one or more kinds of amino acids selected from the group consisting of L-amino acids and glycine.

Examples of the one or more kinds of amino acids selected from the group consisting of L-amino acids and glycine are preferably one or more kinds of amino acids selected from the group consisting of L-Ala, L-Gln, L-Glu, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, 4-L-HYP, 3-L-HYP, L-Orn, L-Cit and Gly, more preferably two kinds of amino acids selected from the group consisting of L-Ala, L-Gln, L-Glu, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB and Gly, further preferably L-Ala and L-Gln.

The microorganisms which have the ability to produce a protein having the activity to form a dipeptide from one or more kinds of amino acids selected from the group consisting of L-amino acids and glycine and the ability to produce one or more kinds of amino acids selected from the group consisting of L-amino acids and glycine include microorganisms having the ability to produce the protein of the above (1)(b) and having the ability to produce one or more kinds of amino acids selected from the group consisting of L-amino acids and glycine. Examples of the microorganisms include microorganisms transformed with DNA encoding the proteins according to [5] to [8] of the above (1)(b) and having the enhanced ability to form and accumulate one or more kinds of amino acids selected from the group consisting of L-amino acids and glycine.

The DNAs encoding the proteins according to [5] to [8] of (1)(b) include:

[12] DNA having the nucleotide sequence of any of SEQ ID NOS: 9 to 17;

[13] DNA which hybridizes with DNA having a nucleotide sequence complementary to the nucleotide sequence of any of SEQ ID NOS: 9 to 17 under stringent conditions and which encodes a protein having the activity to form a dipeptide; and [14] DNA comprising a nucleotide sequence which has at least 80% homology, preferably 90% or more homology, more preferably 95% or more homology, further preferably 98% or more homology, particularly preferably 99% or more homology to the nucleotide sequence of SEQ ID NO: 19 and encoding a protein having the activity to form a dipeptide.

The above expression "to hybridize" has the same significance as in the above (a).

It is possible to confirm that the DNA which hybridizes with the above DNA under stringent conditions is DNA encoding a protein having the activity to form a dipeptide from one or more kinds of amino acids selected from the group consisting of L-amino acids and glycine in the following manner. That is, a recombinant DNA expressing the DNA is prepared, and a microorganism obtained by introducing the recombinant DNA into a host cell as an enzyme source and one or more kinds of amino acids selected from the group consisting of L-amino acids and glycine are allowed to be present in an aqueous medium, followed by HPLC analysis or the like to know whether a dipeptide is formed and accumulated in the aqueous medium.

(c) The microorganisms which produce a protein having the activity to form a dipeptide from one or more kinds of amino acids selected from the group consisting of L-amino acids, glycine and β-alanine, and the microorganisms having the ability to produce one or more kinds of amino acids selected from the group consisting of L-amino acids and glycine and having the ability to produce a dipeptide from one or more kinds of amino acids selected from the group consisting of L-amino acids and glycine, which are both used in the present invention, may be the microorganisms of the above (a) or (b) and may also be 1) microorganisms in which the activities of one or more kinds of peptidases and one or more kinds of proteins having peptide-incorporating activity (hereinafter abbreviated as peptide-incorporating protein) are reduced or lost, or 2) microorganisms in which the activities of three or more kinds of peptidases are reduced or lost.

The microorganisms in which the activities of one or more kinds of peptidases and one or more kinds of peptide-incorporating proteins are reduced or lost include microorganisms in which the activities of one or more arbitrary kinds of peptidases and one or more arbitrary kinds of peptide-incorporating proteins are reduced or lost provided that the microorganisms can normally grow, specifically, microorganisms in which the activities of preferably one to nine kinds, more preferably one to seven kinds, further preferably one to four kinds of peptidases and preferably one to five kinds, more preferably one to three kinds, further preferably one or two kinds, particularly preferably one kind of peptide-incorporating protein are reduced or lost.

Examples of such microorganisms are microorganisms in which the activities of one or more kinds of peptidases and one or more kinds of peptide-incorporating proteins are reduced or lost because the nucleotide sequences of one or more kinds of genes encoding peptidases (hereinafter referred to as peptidase genes) and one or more kinds of genes encoding peptide-incorporating proteins (hereinafter referred to as peptide-incorporating protein genes) among the peptidase genes and peptide-incorporating protein genes existing on the genomic DNA of the microorganisms are entirely or partially deleted or said nucleotide sequences contain nucleotide substitutions or additions.

The expression "the activity of peptidase is reduced" means that the peptide degrading activity is reduced compared with peptidase having none of the above deletions, substitutions and additions of nucleotides, preferably, peptidase activity is reduced by at least 20%, more preferably 50% or more, further preferably 80% or more, particularly preferably 90% or more compared with a peptidase encoded by a wild-type gene which contains none of the above deletions, substitutions and additions of nucleotides.

The peptide degrading activity of a microorganism can be measured by allowing a peptide as a substrate and microorganism cells to be present in an aqueous medium, thereby performing peptide degrading reaction, and then determining the amount of the remaining peptide by a known method, e.g., HPLC analysis.

The above peptidases may be any proteins having peptide degrading activity. Preferred are proteins having high dipeptide-degrading activity. More preferred are dipeptidases.

Examples of peptidases include: those existing in *Escherichia coli* such as PepA having the amino acid sequence of SEQ ID NO: 20, PepB having the amino acid sequence of SEQ ID NO: 21, PepD having the amino acid sequence of SEQ ID NO: 22, PepN having the amino acid sequence of SEQ ID NO: 23, PepP [GenBank accession No. (hereinafter abbreviated as Genbank) AAC75946], PepQ (GenBank AAC76850), PepE (GenBank AAC76991), PepT (GenBank AAC74211), Dcp (GenBank AAC74611) and IadA (GenBank AAC77284); those existing in *Bacillus subtilis* such as AmpS (GenBank AF012285), PepT (GenBank X99339), YbaC (GenBank Z99104), YcdD (GenBank Z99105), YjbG (GenBank Z99110), YkvY (GenBank Z99111), YqjE (GenBank Z99116) and YwaD (GenBank Z99123); those existing in *Corynebacterium glutamicum* such as proteins having the amino acid sequences represented by BAB97732, BAB97858, BAB98080, BAB98880, BAB98892, BAB99013, BAB99598 and BAB99819 (registration Nos. of DNA Data Bank of Japan); and those existing in *Saccharomyces cerevisiae* such as OCT1 (GenBank NC$_{001143}$), SPC2 (GenBank NC$_{003143}$), SPY2 [Saccharomyces genome database accession no. L0002875] and YIM1 (GenBank NC$_{001145}$). Examples of dipeptidases include PepA, PepB, PepD and PepN having the amino acid sequences of SEQ ID NOS: 20 to 23, PepQ, PepE and IadA. Proteins having amino acid sequences which have 80% or more, preferably 90% or more, more preferably 95% or more, further preferably 98% or more, particularly preferably 99% or more homology to the amino acid sequence of any of SEQ ID NOS: 20 to 23 and having peptidase activity are also included in the proteins having high dipeptide-degrading activity.

The homology among amino acid sequences can be determined by using programs such as BLAST and FASTA described above.

The expression "the activity of a peptide-incorporating protein is reduced" means that the peptide-incorporating activity of the protein is reduced compared with a peptide-incorporating protein encoded by DNA having none of the above deletions, substitutions and insertions of nucleotides, preferably, the peptide-incorporating activity of the protein is reduced by at least 20%, more preferably 50% or more, further preferably 80% or more, particularly preferably 90% or more compared with a peptide-incorporating protein encoded by a wild-type gene which contains none of the above deletions, substitutions and additions of nucleotides.

The peptide-incorporating activity of a microorganism can be measured by allowing a peptide as a substrate and microorganism cells to be present in an aqueous medium, thereby performing peptide-incorporating reaction, and then determining the amount of the remaining peptide by a known method, e.g., HPLC analysis.

The above peptide-incorporating proteins may be any proteins involved in peptide incorporation of microorganisms, for example, proteins encoded by genes forming an operon on chromosomal DNA which form a complex on cell membrane to express dipeptide-incorporating activity and those which have peptide-incorporating activity as individual proteins. Preferred are proteins having high peptide-incorporating activity.

Examples of the peptide-incorporating proteins include: those existing in *Escherichia coli* such as DppA having the amino acid sequence shown in SEQ ID NO: 24, DppB having the amino acid sequence of SEQ ID NO: 25, DppC having the amino acid sequence of SEQ ID NO: 26, DppD having the amino acid sequence of SEQ ID NO: 27, DppF having the amino acid sequence of SEQ ID NO: 28, OppA (GenBank AAC76569), OppB (GenBank AAC76568), OppC (GenBank AAC76567), OppD (GenBank AAC76566), OppF (GenBank AAC76565), YddO (GenBank AAC74556), YddP (GenBank AAC74557), YddQ (GenBank AAC74558), YddR (GenBank AAC74559), YddS (GenBank AAC74560), YbiK (GenBank AAC73915), MppA (GenBank AAC74411), SapA (GenBank AAC74376), SapB (GenBank AAC74375), SapC (GenBank AAC74374), SapD (GenBank AAC74373) and SapF (GenBank AAC74372); those existing in *Bacillus subtilis* such as DppA (GenBank CAA40002), DppB (GenBank CAA40003), DppC (GenBank CAA40004), DppD (GenBank CAA40005), DppE (GenBank CAA40006), OppA (GenBank CAA39787), OppB (GenBank CAA39788), OppC (GenBank CAA39789), OppD (GenBank CAA39790), OppF (GenBank CAA39791), AppA (GenBank CAA62358), AppB (GenBank CAA62359), AppC (GenBank CAA62360), AppD (GenBank CAA62356), AppP (GenBank CAA62357), YclF (GenBank CAB12175) and YkfD (GenBank CAB13157); those existing in *Corynebacterium glutamicum* such as proteins having the amino acid sequences represented by BAB99048, BAB99383, BAB99384, BAB99385, BAB99713, BAB99714, BAB99715, BAB99830, BAB99831 and BAB99832 (registration Nos. of DNA Data Bank of Japan); and those existing in *Saccharomyces cerevisiae* such as OPT1 (GenBank NP_012323), OPT2 (GenBank NP_015520) and PTR2 (GenBank CAA82172). Examples of the proteins having high peptide-incorporating activity include DppA, DppB, DppC, DppD and DppF having the amino acid sequences of SEQ ID NOS: 24 to 28, and proteins having amino acid sequences which have 80% or more, preferably 90% or more, more preferably 95% or more, further preferably 98% or more, particularly preferably 99% or more homology to the amino acid sequence of any of SEQ ID NOS: 24 to 28.

The homology among amino acid sequences can be determined by using programs such as BLAST and FASTA described above.

The microorganisms in which the activities of three or more kinds of peptidases are reduced or lost include microorganisms in which the activities of three or more arbitrary kinds of peptidases are reduced or lost provided that the microorganisms can normally grow, specifically, microorganisms in which the activities of preferably three to nine kinds, more preferably three to six kinds, further preferably three or four kinds of peptidases are reduced or lost.

Examples of peptidases include the above-described peptidases and dipeptidases existing in *Escherichia coli, Bacillus subtilis, Corynebacterium glutamicum* and *Saccharomyces cerevisiae*. Proteins consisting of amino acid sequences which have 80% or more, preferably 90% or more, more preferably 95% or more, further preferably 98% or more, particularly preferably 99% or more homology to the amino acid sequence of any of SEQ ID NOS: 20 to 23 and having peptidase activity are also included in the proteins having high dipeptide-degrading activity.

The homology among amino acid sequences can be determined by using programs such as BLAST and FASTA described above.

(3) Process for Producing Microorganisms Used in the Process of the Present Invention
(a) Process for Producing Microorganisms which have the Ability to Produce a Protein Having the Activity to Form a Dipeptide from One or More Kinds of Amino Acids Selected from the Group Consisting of L-Amino Acids, Glycine and β-Alanine

*Bacillus subtilis, Bacillus amyloliquefaciens, Bacillus coagulans, Bacillus licheniformis, Bacillus megaterium* and *Bacillus pumilus* having a bacilysin-synthetase gene described in WO2004/058960, specifically, *Bacillus subtilis* ATCC 23857, *Bacillus subtilis* ATCC 15245, *Bacillus subtilis* ATCC 6633, *Bacillus subtilis* IAM 1213, *Bacillus subtilis* IAM 1107, *Bacillus subtilis* IAM 1214, *Bacillus subtilis* ATCC 9466, *Bacillus subtilis* IAM 1033, *Bacillus subtilis* ATCC 21555 and *Bacillus amyloliquefaciens* IFO 3022, which have the ability to produce a protein having the activity to form a dipeptide from one or more kinds of amino acids selected from the group consisting of L-amino acids, glycine and β-alanine, can be used in the process of the present invention.

The microorganisms which have the ability to produce a protein having the activity to form a dipeptide from one or more kinds of amino acids selected from the group consisting of L-amino acids, glycine and β-alanine can also be obtained by transforming a host microorganism with DNA encoding the protein.

[1] Preparation of DNA Encoding a Protein Having the Activity to Form a Dipeptide from One or More Kinds of Amino Acids Selected from the Group Consisting of L-Amino Acids, Glycine and β-Alanine DNA having the activity to form a dipeptide from one or more kinds of amino acids selected from the group consisting of L-amino acids, glycine and β-alanine can be prepared by the method described in WO2004/058960, for example, by Southern hybridization of a chromosomal DNA library from a microorganism, preferably a microorganism belonging to the genus *Bacillus* using a probe which can be designed based on the nucleotide sequence of any of SEQ ID NOS: 9 to 17, or by PCR [PCR Protocols, Academic Press (1990)] using primer DNAs which can be designed based on the nucleotide sequence of any of SEQ ID NOS: 9 to 17, and as a template, the chromosomal DNA of a microorganism, preferably a microorganism belonging to the genus *Bacills*. It is also possible to obtain the DNA encoding a protein having the activity to form a dipeptide by conducting a search through various gene sequence databases for a sequence having 75% or more homology, preferably 85% or more homology, more preferably 90% or more homology, further preferably 95% or more homology, particularly preferably 98% or more homology, most preferably 99% or more homology to the nucleotide sequence of DNA encoding the amino acid sequence of any of SEQ ID NOS: 1 to 8, and obtaining the desired DNA, based on the nucleotide sequence obtained by the search, from a chromosomal DNA or cDNA library of an organism having the nucleotide sequence according to the above-described method.

The obtained DNA, as such or after cleavage with appropriate restriction enzymes, is inserted into a vector by a conventional method, and the obtained recombinant DNA is introduced into a host cell. Then, the nucleotide sequence of the DNA can be determined by a conventional sequencing method such as the dideoxy method [Proc. Natl. Acad. Sci., USA, 74, 5463 (1977)] or by using a nucleotide sequencer such as 373A DNA Sequencer (Perkin-Elmer Corp.).

In cases where the obtained DNA is found to be a partial DNA by the analysis of nucleotide sequence, the full length DNA can be obtained by Southern hybridization of a chromosomal DNA library using the partial DNA as a probe.

It is also possible to prepare the desired DNA by chemical synthesis using a DNA synthesizer (e.g., Model 8905, Per-Septive Biosystems) based on the determined nucleotide sequence of the DNA.

Examples of the DNAs that can be obtained by the above-described method are DNAs having the nucleotide sequences shown in SEQ ID NOS: 9 to 17.

Examples of the vectors for inserting the above DNA include pBluescript II KS(+) (Stratagene), pDIRECT [Nucleic Acids Res., 18, 6069 (1990)], pCR-Script Amp SK(+) (Stratagene), pT7Blue (Novagen, Inc.), pCR II (Invitrogen Corp.) and pCR-TRAP (Genhunter Corp.).

As the host cell, microorganisms belonging to the genus *Escherichia*, etc. can be used. Examples of the microorganisms belonging to the genus *Escherichia* include *Escherichia coli* XL1-Blue, *Escherichia coli* XL2-Blue, *Escherichia coli* DH1, *Escherichia coli* MC1000, *Escherichia coli* ATCC 12435, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522 and *Escherichia coli* ME8415.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

[2] Process for Producing Microorganisms Transformed with DNA Encoding a Protein Having the Activity to Form a Dipeptide from One or More Kinds of Amino Acids Selected from the Group Consisting of L-Amino Acids, Glycine and β-Alanine On the basis of the DNA obtained by the method of the above [1], a DNA fragment of an appropriate length comprising a region encoding the protein having dipeptide-forming activity is prepared according to need. The productivity of the protein can be enhanced by replacing a nucleotide in the nucleotide sequence of the region encoding the protein so as to make a codon most suitable for the expression in a host cell.

The DNA fragment is inserted downstream of a promoter in an appropriate expression vector to prepare a recombinant DNA.

A transformant which produces the protein having the activity to form a dipeptide can be obtained by introducing the recombinant DNA into a host cell suited for the expression vector.

As the host cell, any microorganisms such as bacterial cells and yeast cells that are capable of expressing the desired gene can be used.

The expression vectors that can be employed are those capable of autonomous replication or integration into the chromosome in the above host cells and comprising a promoter at a position appropriate for the transcription of the DNA encoding the protein having the activity to form a dipeptide.

When a procaryote such as a bacterium is used as the host cell, it is preferred that the recombinant DNA comprising the DNA encoding the protein having the activity to form a dipeptide is a recombinant DNA which is capable of autonomous replication in the procaryote and which comprises a promoter, a ribosome binding sequence, the DNA encoding the protein having dipeptide-synthesizing activity, and a transcription termination sequence. The recombinant DNA may further comprise a gene regulating the promoter.

Examples of suitable expression vectors are pBTrp2, pBTac1 and pBTac2 (products of Boehringer Mannheim GmbH), pHelix1 (Roche Diagnostics Corp.), pKK233-2 (Amersham Pharmacia Biotech), pSE280 (Invitrogen Corp.), pGEMEX-1 (Promega Corp.), pQE-8 (Qiagen, Inc.), pET-3 (Novagen, Inc.), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(+), pBluescript II KS(−) (Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [Gene, 33, 103 (1985)], pSTV28 (Takara Shuzo Co., Ltd.), pUC118 (Takara Shuzo Co., Ltd.) and pPA1 (Japanese Published Unexamined Patent Application No. 233798/88).

As the promoters, any promoters capable of functioning in host cells such as *Escherichia coli* can be used. For example, promoters derived from *Escherichia coli* or phage, such as trp promoter ($P_{trp}$), lac promoter ($P_{lac}$), $P_L$ promoter, $P_R$ promoter and $P_{SE}$ promoter, SPO1 promoter, SPO2 promoter and penP promoter can be used. Artificially designed and modified promoters such as a promoter in which two $P_{trp}$s are combined in tandem, tac promoter, lacT7 promoter and letI promoter, etc. can also be used.

Also useful are promoters such as xylA promoter for the expression in bacteria belonging to the genus *Bacillus* [Appl. Microbiol. Biotechnol., 35, 594-599 (1991)] and P54-6 promoter for the expression in bacteria belonging to the genus *Corynebacterium* [Appl. Microbiol. Biotechnol., 53, 674-679 (2000)].

It is preferred to use a plasmid in which the distance between the Shine-Dalgarno sequence (ribosome binding sequence) and the initiation codon is adjusted to an appropriate length (e.g., 6 to 18 nucleotides).

In the recombinant DNA wherein the DNA encoding the protein having dipeptide-forming activity is ligated to an expression vector, the transcription termination sequence is not essential, but it is preferred to place the transcription termination sequence immediately downstream of the structural gene.

An example of such recombinant DNA is pPE43 described in WO2004/058960.

Examples of procaryotes used as the host cells include microorganisms belonging to the genera *Escherichia*, *Bacillus* and *Corynebacterium*. Specific examples are *Escherichia coli* XL1-Blue, *Escherichia coli* XL2-Blue, *Escherichia coli* DH1, *Escherichia coli* DH5α, *Escherichia coli* MC1000, *Escherichia coli* KY3276, *Escherichia coli* W1485, *Escherichia coli* JM101, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Bacillus subtilis* ATCC 33712, *Bacillus megaterium*, *Bacillus* sp. FERM BP-6030, *Bacillus amyloliquefaciens*, *Bacillus coagulans*, *Bacillus licheniformis*, *Bacillus pumilus*, *Corynebacterium glutamicum* ATCC 13032 and *Corynebacterium glutamicum* ATCC 14297.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

When a strain belonging to the genus *Saccharomyces* is used as the host cell, YEp13 (ATCC 37115), YEp24 (ATCC 37051), YCp50 (ATCC 37419), pHS19, pHS15, etc. can be used as the expression vector.

As the promoter, any promoters capable of functioning in strains belonging to the genus *Saccharomyces* can be used. Suitable promoters include PHO5 promoter, PGK promoter, GAP promoter, ADH promoter, gal 1 promoter, gal 10 promoter, heat shock polypeptide promoter, MFα1 promoter and CUP 1 promoter.

Examples of suitable host cells are strains belonging to the genus *Saccharomyces*, specifically, *Saccharomyces cerevisiae*.

Introduction of the recombinant DNA can be carried out by any of the methods for introducing DNA into yeast, for example, electroporation [Methods Enzymol., 194, 182 (1990)], the spheroplast method [Proc. Natl. Acad. Sci. USA, 81, 4889 (1984)] and the lithium acetate method [J. Bacteriol., 153, 163 (1983)].

[3] Process for Producing a Protein Having the Activity to Form a Dipeptide from One or More Kinds of Amino Acids Selected from the Group Consisting of L-Amino Acids, Glycine and β-Alanine A protein having the activity to form a dipeptide from one or more kinds of amino acids selected from the group consisting of L-amino acids, glycine and β-alanine can be produced by culturing a transformant which can be obtained by transforming a host cell with the DNA encoding the protein prepared by the method of the above [1] in a medium, and isolating and purifying the protein from the culture.

As the host cell, any bacterial cells, yeast cells, animal cells, insect cells, plant cells, etc. that are capable of expressing the gene encoding the protein can be used. Preferred are bacterial cells, more preferred are procaryotes, and further preferred are procaryotes belonging to the genus *Escherichia*.

Culturing of the above transformant in a medium and isolation and purification of the protein from the culture can be carried out by known methods, for example, the methods described in WO2004/058960.

(b) Process for Producing Microorganisms which have the Ability to Produce One or More Kinds of Amino Acids Selected from the Group Consisting of L-Amino Acids and Glycine and the Ability to Produce a Protein Having the Activity to Form a Dipeptide from One or More Kinds of Amino Acids Selected from the Group Consisting of L-Amino Acids and Glycine The microorganisms which have the ability to produce one or more kinds of amino acids selected from the group consisting of L-amino acids and glycine and the ability to produce a protein having the activity to form a dipeptide from one or more kinds of amino acids selected from the group consisting of L-amino acids and glycine used in the process of the present invention can be obtained by transforming a microorganism inherently having the ability to produce one or more kinds of amino acids selected from the group consisting of L-amino acids and glycine with DNA encoding a protein having the activity to form a dipeptide from one or more kinds of amino acids selected from the group consisting of L-amino acids and glycine. The microorganisms can also be obtained, for example, (i) by artificially enhancing the ability to produce one or more kinds of amino acids selected from the group consisting of L-amino acids and glycine of a microorganism having the ability to produce a protein having the activity to form a dipeptide from one or more kinds of amino acids selected from the group consisting of L-amino acids and glycine by a known method; or (ii) by transforming a microbial strain having an enhanced ability to produce one or more kinds of amino acids selected from the group consisting of L-amino acids and glycine with DNA encoding a protein having the activity to form a dipeptide from one or more kinds of amino acids selected from the group consisting of L-amino acids and glycine.

The microorganism having the ability to produce a protein having the activity to form a dipeptide from one or more kinds of amino acids selected from the group consisting of L-amino acids and glycine can be produced in the same manner as the process for producing the microorganism having the ability to produce a protein having the activity to form a dipeptide from one or more kinds of amino acids selected from the group consisting of L-amino acids, glycine and β-alanine of the above (a).

The microorganism having the ability to produce one or more kinds of amino acids selected from the group consisting of L-amino acids and glycine and the microorganism whose ability to produce the amino acids is enhanced by a known method may be microorganisms artificially modified by a known method to form and accumulate the amino acids. Examples of the known methods include:

[1] a method in which at least one of the mechanisms regulating the biosynthesis of one or more kinds of amino acids selected from the group consisting of L-amino acids and glycine is relaxed or canceled;

[2] a method in which the expression of at least one of the enzymes involved in the biosynthesis of the amino acids is enhanced;

[3] a method in which the copy number of at least one of the enzyme genes involved in the biosynthesis of the amino acids is increased;

[4] a method in which at least one of the metabolic pathways branching from the biosynthetic pathway of the amino acids into metabolites other than the amino acids is weakened or blocked; and

[5] a method in which a cell strain having a higher resistance to an analogue of the amino acids as compared with a wild-type strain is selected.

The above known methods can be used alone or in combination.

Specific methods of the above [1] are described in Agric. Biol. Chem., 43, 105-111 (1979), J. Bacteriol., 110, 761-763 (1972), Appl. Microbiol. Biotechnol., 39, 318-323 (1993), etc. Specific methods of the above [2] are described in Agric. Biol. Chem., 43, 105-111 (1979), J. Bacteriol., 110, 761-763 (1972), etc. Specific methods of the above [3] are described in Appl. Microbiol. Biotechnol., 39, 318-323 (1993), Agric. Biol. Chem., 39, 371-377 (1987), etc. Specific methods of the above [4] are described in Appl. Environ. Microbiol., 38, 181-190 (1979), Agric. Biol. Chem., 42, 1773-1778 (1978), etc. Specific methods of the above [5] are described in Agric. Biol. Chem., 36, 1675-1684 (1972), Agric. Biol. Chem., 41, 109-116 (1977), Agric. Biol. Chem., 37, 2013-2023 (1973), Agric. Biol. Chem., 51, 2089-2094 (1987), etc. Microorganisms having the ability to form and accumulate various kinds of amino acids can be prepared by referring to the above publications.

Further, as for the preparation of microorganisms having the ability to form and accumulate amino acids by the methods of the above [1] to [5], alone or in combination, many examples are described in Biotechnology 2nd ed., Vol. 6, Products of Primary Metabolism (VCH Verlagsgesellschaft mbH, Weinheim, 1996) section 14a, 14b; Advances in Biochemical Engineering/Biotechnology 79, 1-35 (2003); Hiroshi Soda, et al., Amino Acid Fermentation, Gakkai Shuppan Center (1986), etc. In addition, there are a number of reports on the specific methods for preparing microorganisms having the ability to form and accumulate amino acids; for example, Japanese Published Unexamined Patent Application No. 164297/03; Agric. Biol. Chem., 39, 153-160 (1975); Agric. Biol. Chem., 39, 1149-1153 (1975); Japanese Published Unexamined Patent Application No. 13599/83; J. Gen. Appl. Microbiol., 4, 272-283 (1958); Japanese Published Unexamined Patent Application No. 94985/88; Agric. Biol. Chem., 37, 2013-2023 (1973); WO97/15673; Japanese Published Unexamined Patent Application No. 18596/81; Japanese Published Unexamined Patent Application No. 144092/81; and PCT National Publication No. 511086/03. Microorganisms having the ability to form and accumulate one or more kinds of amino acids selected from the group consisting of L-amino acids and glycine can be prepared by referring to the above publications.

Examples of the microorganisms having the ability to produce amino acids prepared by the above methods include L-glutamine-producing strains (e.g. a microorganism wherein the glnE gene and/or the glnB gene are deleted), L-alanine-producing strains [e.g. a microorganism wherein the expression of alanine dehydrogenase gene (ald gene) is enhanced], and L-proline-producing microorganisms (e.g. a microorganism expressing the phenylalanine-desensitized pheA gene and/or the tyrosine-desensitized aroF gene).

The above microorganisms having the ability to produce amino acids may be any microorganisms to which the above methods [1] to [5] can be applied or any microorganisms having the above genetic characters. Preferred are procaryotes and more preferred are bacteria.

Examples of the procaryotes include microorganisms belonging to the genera *Escherichia, Serratia, Bacillus, Brevibacterium, Corynebacterium, Microbacterium, Pseudomonas, Agrobacterium, Alicyclobacillus, Anabaena, Anacystis, Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus* and *Zymomonas*. Specific examples are *Escherichia coli, Bacillus subtilis, Bacillus megaterium, Bacillus amyloliquefaciens, Bacillus coagulans, Bacillus licheniformis, Bacillus pumilus, Brevibacterium ammoniagenes, Brevibacterium immariophilum, Brevibacterium saccharolyticum, Brevibacterium flavum, Brevibacterium lactofermentum, Corynebacterium glutamicum, Corynebacterium acetoacidophilum, Microbacterium ammoniaphilum, Serratia ficaria, Serratia fonticola, Serratia liquefaciens, Serratia marcescens, Pseudomonas aeruginosa, Pseudomonas putida, Agrobacterium radiobacter, Agrobacterium rhizogenes, Agrobacterium rubi, Anabaena cylindrica, Anabaena doliolum, Anabaena flos-aquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Phormidium* sp. ATCC 29409, *Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus* and *Zymomonas mobilis*. Preferred procaryotes include bacteria belonging to the genera *Escherichia, Serratia, Bacillus, Brevibacterium, Corynebacterium, Pseudomonas* and *Streptomyces*, for example, the above-mentioned species belonging to the genera *Escherichia, Serratia, Bacillus, Brevibacterium, Corynebacterium, Pseudomonas* and *Streptomyces*. More preferred bacteria include *Escherichia coli, Corynebacterium glutamicum, Corynebacterium ammoniagenes, Corynebacterium lactofermentum, Corynebacterium flavum, Corynebacterium efficasis, Bacillus subtilis, Bacillus megaterium, Serratia marcescens, Pseudomonas putida, Pseudomonas aeruginosa, Streptomyces coelicolor* and *Streptomyces lividans*, among which *Escherichia coli* is particularly preferred.

Specific examples of the microorganisms having the ability to produce L-alanine or L-glutamine include *Escherichia coli* JGLE1 and *Escherichia coli* JGLBE1 described below, which are L-glutamine-producing strains, *Escherichia coli* JM101 carrying an ald gene expression plasmid, which is an L-alanine-producing strain, and *Escherichia coli* JGLE1 and *Escherichia coli* JGLBE1 carrying an ald gene expression plasmid, which are L-glutamine- and L-alanine-producing strains.

Specific examples of the microorganisms having the ability to form and accumulate one or more kinds of amino acids selected from the group consisting of L-amino acids and glycine include FERM BP-5807 and ATCC 13032 strains producing L-glutamic acid, FERM P-4806 and ATCC 14751 strains producing L-glutamine, ATCC 21148, ATCC 21277 and ATCC 21650 strains producing L-threonine, FERM P-5084 and ATCC 13286 strains producing L-lysine, FERM P-5479, VKPM B-2175 and ATCC 21608 strains producing L-methionine, FERM BP-3757 and ATCC 14310 strains producing L-isoleucine, ATCC 13005 and ATCC 19561 strains producing L-valine, FERM BP-4704 and ATCC 21302 strains producing L-leucine, FERM BP-4121 and ATCC 15108 strains producing L-alanine, ATCC 21523 and FERM BP-6576 strains producing L-serine, FERM BP-2807 and ATCC 19224 strains producing L-proline, FERM P-5616 and ATCC 21831 strains producing L-arginine, ATCC 13232 strain producing L-ornithine, FERM BP-6674 and ATCC 21607 strains producing L-histidine, DSM 10118, DSM 10121, DSM 10123 and FERM BP-1777 strains producing L-tryptophan, ATCC 13281 and ATCC 21669 strains producing L-phenylalanine, ATCC 21652 strain producing L-tyrosine, W3110/pHC34 strain producing L-cysteine (PCT National Publication No. 511086/03), *Escherichia coli* SOLR/pRH71 producing L-4-hydroxyproline described in WO96/27669, FERM BP-5026 and FERM BP-5409 strains producing L-3-hydroxyproline, and FERM P-5643 and FERM P-1645 strains producing L-citrulline.

The above strains designated by FERM Nos., ATCC Nos., VKPM Nos. and DSM Nos. are available from International Patent Organism Depositary, National Institute of Advanced Industrial Science and Technology (Japan), American Type Culture Collection (U.S.A.), Russian National Collection of Industrial Microorganisms (Russia) and Deutsche Sammlung von Mikroorganismen und Zellkulturen (Germany), respectively.

The microorganisms used in the process of the present invention can be produced by transforming microbial strains having the ability to produce one or more kinds of amino acids selected from the group consisting of L-amino acids and glycine represented by the above strains by the method of the above (a)[2] using the DNA obtained by the method of the above (a)[1].

(c) Process for Producing Microorganisms in which the Activities of Peptidases and Proteins Having Peptide-Incorporating Activity are Reduced or Lost The microorganisms used in the production process of the present invention include microorganisms prepared by the method of the above (a) or (b) in which the activities of one or more kinds of peptidases and one or more kinds of proteins having peptide-incorporating activity (hereinafter referred to as peptide-incorporating proteins) are reduced or lost, or those in which the activities of three or more kinds of peptidases are reduced or lost.

Such microorganisms can be obtained, for example, by the following methods: (i) a method of imparting, by the method of the above (a), the ability to produce a protein having the activity to form a dipeptide to a microorganism in which the functions of one or more kinds of peptidases and one or more kinds of peptide-incorporating proteins are reduced or lost, or a microorganism in which the functions of three or more kinds of peptidases are reduced or lost; (ii) a method of reducing or causing loss of the functions of a) one or more kinds of peptidases and one or more kinds of peptide-incorporating proteins or b) three or more kinds of peptidases of a microorganism having the ability to produce a protein having the activity to form a dipeptide which can be prepared by the method of the above (a); (iii) a method of imparting, by the method of the above (b), the ability to produce a protein having the activity to form a dipeptide and the ability to form and accumulate one or more kinds of amino acids selected from the group consisting of L-amino acids and glycine to a microorganism in which the functions of one or more kinds of peptidases and one or more kinds of peptide-incorporating proteins are reduced or lost, or a microorganism in which the functions of three or more kinds of peptidases are reduced or lost; and (iv) a method of reducing or causing loss of the functions of a) one or more kinds of peptidases and one or more kinds of peptide-incorporating proteins or b) three or more kinds of peptidases of a microorganism having the ability to produce a protein having the activity to form a dipeptide and the ability to form and accumulate one or more kinds of amino acids selected from the group consisting of L-amino acids and glycine which can be prepared by the method of the above (b).

The microorganisms in which the activities of peptidases and peptide-incorporating proteins are reduced or lost may be obtained by any method capable of preparing such microorganisms. For example, they can be obtained by introducing a deletion, substitution or addition of a nucleotide into peptidase genes and peptide-incorporating protein genes on chromosomal DNAs of microorganisms as described below.

The methods for introducing a deletion, substitution or addition of a nucleotide into a gene on the chromosomal DNA of a microorganism include methods utilizing homologous recombination. An example of a general method utilizing homologous recombination is a method using a plasmid for homologous recombination prepared by ligating a mutant gene having an introduced nucleotide deletion, substitution or addition to a plasmid DNA incapable of autonomous replication in a host cell into which the nucleotide deletion or the like is to be introduced and carrying a drug resistance gene.

The plasmid for homologous recombination is introduced into a host cell by an ordinary method, followed by selection of a transformant in which the plasmid for homologous recombination has been integrated into the chromosomal DNA by homologous recombination using the drug resistance as a marker. The obtained transformant is cultured in a medium which does not contain the drug for several hours to one day, and then spread on an agar medium containing the drug and on an agar medium without the drug. By selecting a strain which does not grow on the former medium but can grow on the latter medium, the strain in which second homologous recombination occurred on the chromosomal DNA can be obtained. Introduction of a deletion, substitution or addition of a nucleotide into a desired gene on the chromosomal DNA can be confirmed by determining the nucleotide sequence of a region of the chromosomal DNA containing the gene into which the deletion or the like has been introduced.

By use of the above method, a deletion, substitution or addition of nucleotide can be introduced into desired genes on chromosomal DNAs of microorganisms such as those belonging to the genera *Escherichia*, *Bacillus* and *Corynebacterium*.

Further, a deletion, substitution or addition of nucleotide can be efficiently introduced into plural genes by utilizing homologous recombination according to a method using a straight-chain DNA.

Specifically, a straight-chain DNA containing a gene into which a deletion, substitution or addition of a nucleotide is to be introduced is incorporated into a cell to cause homologous recombination between chromosomal DNA and the introduced straight-chain DNA. This method is applicable to any microorganisms capable of efficiently incorporating a straight-chain DNA. Preferred microorganisms are those belonging to the genera *Escherichia* and *Bacillus*. *Escherichia coli* is more preferred, and *Escherichia coli* expressing a group of recombinant proteins derived from λ phage (Red recombination system) is further preferred.

An example of *Escherichia coli* expressing λ Red recombination system is *Escherichia coli* JM101 carrying pKD46, which is a plasmid DNA comprising a λ Red recombination system gene (available from *Escherichia coli* Genetic Stock Center, Yale University, U.S.A.).

Examples of the DNAs useful for homologous recombination are as follows:

[1] straight-chain DNA in which DNAs present on the outside of both ends of a region of chromosomal DNA to be subjected to introduction of a deletion, substitution or addition of nucleotide or DNAs having homology to the said DNAs are present at both termini of a drug resistance gene;

[2] straight-chain DNA in which DNAs present on the outside of both ends of a region of chromosomal DNA to be subjected to introduction of a deletion, substitution or addition of nucleotide or DNAs having homology to the said DNAs are directly ligated to each other;

[3] straight-chain DNA in which DNAs present on the outside of both ends of a region of chromosomal DNA to be subjected to introduction of a deletion, substitution or addition of nucleotide or DNAs having homology to the said DNAs are present at both termini of a drug resistance gene and a gene that can be used for negative selection; and

[4] straight-chain DNA of the above [1] in which a nucleotide sequence recognized by yeast-derived Flp recombinase [Proc. Natl. Acad. Sci. USA., 82, 5875 (1985)] is additionally present between the drug resistance gene and the DNAs present on the outside of both ends of the region of chromosomal DNA or DNAs having homology to the said DNAs.

As the drug resistance gene, any drug resistance genes that impart resistance to a drug to which the host microorganism shows sensitivity can be used. When *Escherichia coli* is used as the host microorganism, examples of the drug resistance genes are kanamycin resistance gene, chloramphenicol resistance gene, gentamicin resistance gene, spectinomycin resistance gene, tetracycline resistance gene and ampicillin resistance gene.

The "gene that can be used for negative selection" refers to a gene that is fatal to a host microorganism under certain culture conditions when the gene is expressed in the host microorganism. Examples of the genes are sacB gene derived from a microorganism belonging to the genus *Bacillus* [Appl. Environ. Microbiol., 59, 1361-1366 (1993)] and rpsL gene derived from a microorganism belonging to the genus *Escherichia* [Genomics, 72, 99-104 (2001)].

The DNAs present on the outside of both ends of a region of chromosomal DNA to be subjected to introduction of a substitution or deletion or DNAs having homology to the said DNAs, which exist at both ends of the above straight-chain DNAs, are located in the same direction as that on the chromosomal DNA, and their length is preferably about 10 bp to 100 bp, more preferably about 20 bp to 50 bp, and further preferably about 30 bp to 40 bp.

The nucleotide sequence recognized by yeast-derived Flp recombinase is not specifically limited so long as it is a nucleotide sequence recognized by the said protein and catalyzing homologous recombination. Preferred examples are DNA having the nucleotide sequence of SEQ ID NO: 38, and DNA having a nucleotide sequence wherein one to several nucleotides are deleted, substituted or added in the said DNA and having a nucleotide sequence recognized by yeast-derived Flp recombinase and catalyzing homologous recombination.

The "DNA having homology" refers to DNA having such a degree of identity that allows occurrence of homologous recombination between the subject region of chromosomal DNA and the above straight-chain DNA, specifically, DNA having 80% or more homology, preferably 90% or more homology, more preferably 95% or more homology, further preferably 98% or more homology, particularly preferably 99% or more homology, most preferably 100% homology.

The homology among nucleotide sequences can be determined by using programs such as BLAST and FASTA described above.

The above straight-chain DNA fragments can be prepared by PCR. The desired straight-chain DNA can also be obtained by constructing DNA containing the above straight-chain DNA on plasmid and then carrying out treatment with restriction enzymes.

Examples of the methods for introducing a deletion, substitution or addition of a nucleotide into the chromosomal DNA of a microorganism include the following Methods 1 to 4.

Method 1:
A method which comprises introducing the straight-chain DNA of the above [1] or [2] into a host microorganism and selecting a transformant carrying the straight-chain DNA inserted on its chromosomal DNA by homologous recombination using the drug resistance as a marker.

Method 2:
A method which comprises introducing the DNA in which DNAs present on the outside of both ends of a region of chromosomal DNA to be subjected to introduction of a deletion, substitution or addition of a nucleotide or DNAs having homology to the said DNAs are directly ligated to each other into the transformant obtained according to the above Method 1 and eliminating the drug resistance gene inserted on its chromosomal DNA by Method 1 to substitute or delete a region of the chromosomal DNA of the microorganism.

Method 3:
A method which comprises:
a) introducing the straight-chain DNA of the above [3] into a host microorganism and selecting a transformant carrying the straight-chain DNA inserted on its chromosomal DNA by homologous recombination using the drug resistance as a marker;
b) synthesizing DNA by ligating DNAs having homology to the DNAs present on the outside of both ends of a region of chromosomal DNA to be subjected to introduction of a substitution or deletion in the same direction as that on the chromosomal DNA, and introducing the synthesized DNA into the transformant obtained in the above a); and
c) culturing the transformant subjected to the operation of the above b) under conditions such that the gene that can be used for negative selection is expressed, and selecting a strain capable of growing by the culturing as a strain in which the drug resistance gene and the gene that can be used for negative selection are eliminated from the chromosomal DNA.

Method 4:
A method which comprises:
a) introducing the straight-chain DNA of the above [4] into a host microorganism and selecting a transformant carrying the straight-chain DNA inserted on its chromosomal DNA by homologous recombination using the drug resistance as a marker; and
b) introducing a Flp recombinase gene expression plasmid into the transformant obtained in the above a), and after expression of the gene, obtaining a strain sensitive to the drug used in the above a).

In the above methods, introduction of the straight-chain DNA into a host microorganism can be carried out by any of the methods for introducing DNA into the microorganism, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

By using DNA in which an arbitrary gene to be inserted to chromosomal DNA is incorporated in the center part of the DNA used in Method 2 or Method 3 b), it is possible to eliminate the drug resistance gene and the like and at the same time to insert an arbitrary gene to the chromosomal DNA.

The above Methods 2 to 4 are methods that leave no foreign genes such as a drug resistance gene and a gene usable for negative selection on the chromosomal DNA of the transformant to be finally obtained. Therefore, it is possible to readily produce a microorganism having deletions, substitutions or additions of nucleotides in two or more different regions of the chromosomal DNA by repeating the above operations using the same drug resistance gene and the same gene usable for negative selection.

(4) Process for Producing Dipeptide Crystals of the Present Invention (a) The dipeptide crystals of the present invention can be produced by allowing an enzyme source and one or more kinds of amino acids selected from the group consisting of L-amino acids, glycine and β-alanine to be present in an aqueous medium, said enzyme source being a protein having the activity to form a dipeptide from one or more kinds of amino acids selected from the group consisting of L-amino acids, glycine and β-alanine, a culture of a microorganism having the ability to produce the protein or a treated matter of the culture, allowing the dipeptide to form and accumulate in the aqueous medium, and recovering crystals of the dipeptide from the aqueous medium.

A culture of the microorganism can be obtained by culturing the microorganism in a medium. Culturing can be carried out according to an ordinary method used for culturing of a microorganism.

That is, any of natural media and synthetic media can be used insofar as it is a medium suitable for efficient culturing of the microorganism which contains carbon sources, nitrogen sources, inorganic salts, etc. which can be assimilated by the microorganism.

As the carbon sources, any carbon sources that can be assimilated by the microorganism can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration. The culturing temperature is preferably 15 to 40° C., and the culturing period is usually 5 hours to 7 days. The pH is maintained at 3.0 to 9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside or the like may be added to the medium; and in the case of a microorganism transformed with an expression vector comprising trp promoter, indoleacrylic acid or the like may be added.

In the above process, the protein having dipeptide-forming activity used as an enzyme source is added in an amount of 0.01 to 100 mg, preferably 0.1 mg to 10 mg per mg of amino acid used as a substrate, and ATP may be added to the reaction solution at a concentration of 0.5 mmol to 10 mol/l as an energy source according to need.

In the above process, the amino acid used as a substrate is added to the aqueous medium at the start or in the course of reaction to give a concentration of 0.1 to 500 g/l, preferably 0.2 to 200 g/l.

The aqueous medium used in the above process may comprise any components and may have any composition so far as the dipeptide-forming reaction is not inhibited. Suitable aqueous media include water and buffers such as phosphate buffer, carbonate buffer, acetate buffer, borate buffer, citrate buffer and Tris buffer. The aqueous medium may comprise alcohols such as methanol and ethanol, esters such as ethyl acetate, ketones such as acetone, and amides such as acetamide.

Further, when a culture of a microorganism or a treated matter of the culture is used as an enzyme source, the culture of a microorganism used as an enzyme source can also be used as the aqueous medium in addition to the above aqueous media. Compounds which can be metabolized by the microorganism to produce ATP, for example, sugars such as glucose, alcohols such as ethanol, and organic acids such as acetic acid may be added, as ATP source, to the aqueous medium.

If necessary, a surfactant or an organic solvent may further be added to the aqueous medium. Any surfactant that promotes the formation of a dipeptide can be used. Suitable surfactants include nonionic surfactants such as polyoxyethylene octadecylamine (e.g., Nymeen S-215, NOF Corporation), cationic surfactants such as cetyltrimethylammonium bromide and alkyldimethylbenzylammonium chloride (e.g., Cation F2-40E, NOF Corporation), anionic surfactants such as lauroyl sarcosinate, and tertiary amines such as alkyldimethylamine (e.g., Tertiary Amine FB, NOF Corporation), which may be used alone or in combination. The surfactant is usually used at a concentration of 0.1 to 50 g/l. As the organic solvent, xylene, toluene, aliphatic alcohols, acetone, ethyl acetate, etc. may be used usually at a concentration of 0.1 to 50 ml/l.

When a culture or a treated matter of the culture is used as the enzyme source, the amount of the enzyme source to be added varies according to its specific activity, etc., but is, for example, 5 to 1000 mg (wet cell weight), preferably 10 to 400 mg per mg of amino acid used as a substrate.

Examples of the treated matters of a culture of the microorganism used in the process of the present invention include products obtained by subjecting the culture obtained by culturing the microorganism of the above (2) to concentration and drying, cells obtained by centrifuging or filtering the culture, products obtained by subjecting the cells to drying, freeze-drying, treatment with a surfactant, ultrasonication, mechanical friction, treatment with a solvent and enzymatic treatment, and treated matters of the culture containing living cells having the same function as the microorganism as an enzyme source, such as a product obtained by subjecting the cells to immobilization.

The dipeptide-forming reaction is carried out in the aqueous medium at pH 5 to 11, preferably pH 6 to 10, at 20 to 65° C., preferably 25 to 55° C., more preferably 30 to 45° C., for 1 minute to 150 hours, preferably 3 minutes to 120 hours, more preferably 30 minutes to 100 hours.

The method for recovering the dipeptide crystals of the present invention formed and accumulated in the aqueous medium is not specifically limited so long as dipeptide crystals which do not substantially comprise a dipeptide comprising D-amino acid as a constituent or a polypeptide consisting of three or more amino acids or those which further do not substantially comprise an amino acid amide can be obtained by the method. For example, a solution comprising the dipeptide of the present invention is subjected, as such (when a protein was used as an enzyme source) or after the removal of the cells by centrifugation or filtration (when a culture or a treated matter of the culture was used as an enzyme source), to treatment for separation of contaminant amino acids and polypeptides, such as treatment using a synthetic adsorbent and ion exchange resins such as a cation exchange resin and an anion exchange resin, treatment using activated carbon and crystallizing treatment, as well as treatment for removal of specific contaminants, which are carried out singly or in combination according to need, followed by crystallization of the desired dipeptide.

There is no specific restriction as to the synthetic adsorbent as long as it can separate the desired dipeptide from contaminants. Examples of the adsorbents include nonpolar and porous adsorption resins such as DIAION HP resins (e.g., HP10 and HP20; Mitsubishi Chemical Corporation), DIAION SP800 resins (e.g., SP800 and SP825; Mitsubishi Chemical Corporation), DIAION SP200 resins (e.g., SP205, SP207 and SP207S; Mitsubishi Chemical Corporation) and Amberlite XAD resins (e.g., XAD4 and XAD1600; Rohm and Haas).

There is no specific restriction as to the cation exchange resin as long as it can separate the desired dipeptide from contaminants. Examples of strongly acidic cation exchange resins include Amberlite IR resins (e.g., 124Na and 252Na; Organo Corporation) and DOWEX resins (e.g., MARATHON C and XUS-40232.01; The Dow Chemical Company), and examples of weakly acidic cation exchange resins include Amberlite IRC resins (e.g., IRC50 and IRC70; Rohm and Haas) and WK resins (e.g., WK40; Mitsubishi Chemical Corporation).

There is no specific restriction as to the anion exchange resin as long as it can separate the desired dipeptide from contaminants. Examples of strongly basic anion exchange resins include DIAION PA resins (e.g., PA306, PA312 and PA412; Mitsubishi Chemical Corporation), and examples of weakly basic anion exchange resins include DIAION WA resins (e.g., WA10, WA20 and WA30; Mitsubishi Chemical Corporation).

Crystals of L-alanyl-L-glutamine can be recovered, for example, in the following manner. After the completion of the reaction, a solution comprising L-alanyl-L-glutamine, after the removal of cells by centrifugation or filtration when the cells are contained in the reaction solution, is passed through a strongly acidic cation exchange resin (e.g., MARATHON-C) to obtain an eluate fraction comprising L-alanyl-L-glutamine, then the obtained fraction is passed through a weakly acidic cation exchange resin (e.g., IRC50) to obtain an eluate fraction comprising L-alanyl-L-glutamine, and the obtained fraction is passed through a strongly basic anion exchange resin (e.g., PA412) to obtain a solution comprising L-alanyl-L-glutamine, which is used for crystallization of L-alanyl-L-glutamine.

An example of the treatment for removal of specific contaminants is treatment for removal of amino acid selected from the group consisting of L-amino acids, glycine and β-alanine used as a substrate when it is remaining in the aqueous medium. For instance, when L-glutamine is remaining, any treatment capable of removing L-glutamine may be carried out. Preferred are treatments capable of degrading L-glutamine, such as treatment by a resin, heating treatment, and treatment with an acid or a base, and more preferred is heating treatment.

Specifically, heating treatment is carried out, for example, after producing L-alanyl-L-glutamine in an aqueous medium using L-alanine and L-glutamine as substrates, by treating the aqueous medium at 55° C. to 120° C. for 5 minutes to 24 hours, preferably at 70° C. to 100° C. for 15 minutes to 6 hours.

There is no specific restriction as to the method for crystallization of a dipeptide so long as it is a method capable of crystallizing the desired dipeptide. For example, crystallization can be carried out by adding lower alcohol (e.g., methanol, ethanol and propanol), ketone (e.g., acetone) or a solvent (e.g., tetrahydrofuran) to an aqueous solution comprising a dipeptide.

There is no specific restriction as to the conditions for crystallization so long as crystals are deposited. For example, a solvent for crystallization (2 to 5 times the volume of the aqueous solution comprising the dipeptide) is added to the aqueous solution, and then, if necessary, the solution is cooled to 10 to 30° C.

Specifically, crystallization of L-alanyl-L-glutamine can be carried out, for example, by adding methanol (ca. 2 to 5 times, preferably 3 to 4 times the volume of an aqueous solution comprising L-alanyl-L-glutamine) to the aqueous solution at 20 to 70° C., preferably 50 to 70° C., and then cooling the aqueous solution to 10 to 30° C., preferably 15 to 25° C.

Further, crystals of the desired dipeptide may be added to a solution comprising the dipeptide as seed crystals at the time of crystallization. For example, when L-alanyl-L-glutamine is crystallized, methanol (0.3 to 0.5 times the volume of an aqueous solution comprising L-alanyl-L-glutamine) is added to the solution, crystals of L-alanyl-L-glutamine are added thereto in an amount of 1 to 5% by weight based on the weight of L-alanyl-L-glutamine contained in the solution, and then methanol is further added until the total volume becomes 4 times the volume of the starting aqueous solution.

(b) The dipeptide crystals of the present invention can be obtained by culturing in a medium a microorganism having the ability to produce one or more kinds of amino acids selected from the group consisting of L-amino acids and glycine and the ability to produce a protein having the activity to form a dipeptide from one or more kinds of amino acids selected from the group consisting of L-amino acids and glycine, allowing the dipeptide to form and accumulate in the medium, and recovering the dipeptide crystals from the medium.

An example of the method for culturing the microorganism is the method of the above (a).

The medium used for culturing the microorganism does not need to contain amino acids which constitute the desired dipeptide. However, a natural medium or a medium for culturing an amino acid-requiring strain sometimes contains the amino acids. The medium used in the process of the present invention may contain the amino acids in the amount required for the growth of the microorganism used in the present invention. That is, as the amount of amino acids contained in an ordinary medium is very small compared with the amount of those formed and accumulated by the microorganism used, the presence of the amino acids does not affect the amount of dipeptide produced by the present invention, and such amount of the amino acids may be contained in the medium used in the process of the present invention.

The amount of amino acids that may be contained in the medium used in the present invention is, for example, in the case of a natural medium, usually less than 2.5 g/l, preferably 0.5 g/l or less, more preferably 0.1 g/l or less, further preferably 20 mg/l or less, and in the case of a synthetic medium, usually 1 g/l or less, preferably 50 mg/l or less, more preferably 1 mg/l or less, further preferably 0.5 mg/l or less. When the dipeptide to be produced by the process of the present invention consists of two different kinds of amino acids and the microorganism to be used has the ability to produce only one of the amino acids which constitute the dipeptide, the other kind of amino acid which cannot be formed and accumulated by the microorganism may be added to the medium used in the present invention. The amount of the amino acid to be added is usually 0.5 g/l to 100 g/l, preferably 2 g/l to 50 g/l.

An example of the method for recovering the dipeptide crystals of the present invention formed and accumulated in the medium is the method of the above (a), specifically, the method which comprises centrifuging or filtering the culture to remove the cells from the medium and then crystallizing the dipeptide in the same manner as in the above (a).

When L-alanyl-L-glutamine is formed and accumulated in a medium by culturing a microorganism having the ability to produce L-alanine or L-glutamine and the ability to form L-alanyl-L-glutamine from L-alanine and L-glutamine, the contaminant L-glutamine remaining in the medium can be removed by treating the medium in the same manner as the aqueous medium of the above (a), preferably, by heating treatment.

Specifically, heating treatment is carried out, for example, after allowing L-alanyl-L-glutamine to form and accumulate in a medium, by treating the medium at 55° C. to 120° C. for 5 minutes to 24 hours, preferably at 70° C. to 100° C. for 15 minutes to 6 hours.

Crystallization of a dipeptide can be carried out by the same method as in the above (a).

Specifically, crystallization of L-alanyl-L-glutamine can be carried out, for example, by adding methanol (ca. 2 to 5 times, preferably 3 to 4 times the volume of an aqueous solution comprising L-alanyl-1-glutamine) to the aqueous solution at 20 to 70° C., preferably 50 to 70° C., and then cooling the aqueous solution to 10 to 30° C., preferably 15 to 25° C.

At the time of crystallization, crystals of the desired dipeptide may be added to a solution comprising the dipeptide as seed crystals. For example, when L-alanyl-L-glutamine is crystallized by the above method, methanol (0.3 to 0.5 times the volume of an aqueous solution comprising L-alanyl-L-glutamine) is added to the solution, crystals of L-alanyl-L-glutamine are added thereto in an amount of 1 to 5% by weight based on the weight of L-alanyl-L-glutamine contained in the solution, and then methanol is further added until the total volume becomes 4 times the volume of the starting aqueous solution.

Substances contained in commercially available alanyl-glutamine crystals were analyzed and the analysis results are shown as the reference example below.

REFERENCE EXAMPLE

Analysis of Commercially Available L-Alanyl-L-Glutamine Crystals

Table 1 below shows the results of HPLC analysis of commercially available reagents carried out under the following conditions. The upper rows show the area percentage as analyzed by HPLC and the lower rows show the weight percentage calculated from the area percentage.
Analysis Conditions:
  Column: Inertsil ODS-3V (GL Sciences Inc.)
  Temperature: 30° C.
  Mobile phase: Solution A [0.01 mol/l sodium heptane-sulfonate, 0.01 mol/l potassium dihydrogenphosphate (pH 2.5)]: methanol 99:1
  Flow rate: 1.2 ml/min
  Detection: UV 210 nm

TABLE 1

Analysis Results of Substances Contained in L-Alanyl-L-Glutamine Reagents

| | HPLC purity (upper row; area %, lower row; weight %) | | | |
|---|---|---|---|---|
| | L-Ala-L-Gln | DL form | AlaAlaGln | AlaNH$_2$ |
| Nacalai Tesque (Prod. No. M9G7129) | 99.92<br>99.92 | 0.017<br>0.017 | 0.018<br>0.014 | ND |

TABLE 1-continued

Analysis Results of Substances Contained in L-Alanyl-L-Glutamine Reagents

| | HPLC purity (upper row; area %, lower row; weight %) | | | |
|---|---|---|---|---|
| | L-Ala-L-Gln | DL form | AlaAlaGln | AlaNH$_2$ |
| Kokusan Chemical (Prod. No. H558024) | 99.40<br>99.40 | 0.004<br>0.004 | 0.041<br>0.032 | 0.005<br>0.023 |
| Bachem (Prod. No. 114149) | 99.39<br>99.39 | 0.004<br>0.004 | 0.041<br>0.032 | 0.005<br>0.023 |
| Sigma (Prod. No. 032K14932) | 99.71<br>99.71 | 0.150<br>0.150 | ND | ND |
| Tokyo Chemical Ind. (Prod. No. GA11) | 99.46<br>99.46 | 0.004<br>0.004 | 0.068<br>0.053 | ND |

In the table, ND indicates a value below the detection limit (area %: 0.002%), and DL form indicates D-alanyl-L-glutamine.

All of the reagents substantially comprised one or more substances selected from the group consisting of DL form, alanyl-alanyl-glutamine and alanine amide.

The following experimental examples illustrate a process for producing microorganisms having the ability to produce one or more kinds of amino acids selected from the group consisting of L-amino acids and glycine and the ability to produce a protein having the activity to form a dipeptide from one or more kinds of amino acids selected from the group consisting of L-amino acids and glycine in which the activities of one or more kinds of peptidases and one or more kinds of peptide-incorporating proteins are reduced or lost, or those in which the activities of three or more kinds of peptidases are reduced or lost. The method for producing the microorganisms is not limited to the experimental examples.

EXPERIMENTAL EXAMPLE 1

Preparation of Strains in which the pepD, pepN, pepB and pepA Genes and the ddp Operon are Deleted Strains in which specific genes on *Escherichia coli* chromosomal DNA are deleted were prepared according to the method utilizing the homologous recombination system of lambda phage [Proc. Natl. Acad. Sci. USA, 97, 6641-6645 (2000)].

Plasmids pKD46, pKD3 and pCP20 used below were prepared by extraction from *Escherichia coli* strains carrying them which were obtained from *Escherichia coli* Genetic Stock Center, Yale University, U.S.A.

(1) Cloning of DNA Fragments for Gene Deletion

For the purpose of deleting the following genes existing on the chromosomal DNA of *Escherichia coli* K12, DNAs having nucleotide sequences homologous to 36-bp nucleotide sequences that lie upstream and downstream of the respective genes to be deleted on the chromosomal DNA of *Escherichia coli* K12 and the nucleotide sequence of SEQ ID NO: 38 which is recognized by yeast-derived Flp recombinase were synthesized using a DNA synthesizer (Model 8905, PerSeptive Biosystems, Inc.). The genes to be deleted are the pepD gene having the nucleotide sequence of SEQ ID NO: 29, the pepN gene having the nucleotide sequence of SEQ ID NO: 30, the pepB gene having the nucleotide sequence of SEQ ID NO: 31, the pepA gene having the nucleotide sequence of SEQ ID NO: 32, the dppA gene having the nucleotide sequence of SEQ ID NO: 33, the dppB gene having the nucleotide sequence of SEQ ID NO: 34, the dppC gene having the nucleotide sequence of SEQ ID NO: 35, the dppD gene having the nucleotide sequence of SEQ ID NO: 36 and the dppF gene having the nucleotide sequence of SEQ ID NO: 37. In the case of the dppA, dppB, dppC, dppD and dppF genes, which form an operon, DNAs having nucleotide sequences homologous to the nucleotide sequences that lie upstream and downstream of the operon were synthesized.

That is, DNAs consisting of the following nucleotide sequences were synthesized as respective sets of primers for amplification of DNA fragments for gene deletion: SEQ ID NOS: 39 and 40 for pepD gene deletion; SEQ ID NOS: 41 and 42 for pepN gene deletion; SEQ ID NOS: 43 and 44 for pepA gene deletion; SEQ ID NOS: 45 and 46 for pepB gene deletion; and SEQ ID NOS: 47 and 48 for dpp operon deletion.

Subsequently, PCR was carried out using each set of the above synthetic DNAs as a set of primers and pKD3 DNA as a template. PCR was carried out for 30 cycles of 94° C. for one minute, 55° C. for 2 minutes and 72° C. for 3 minutes, using 40 µl of a reaction mixture comprising 10 ng of the plasmid DNA, 0.5 µmol/l each of the primers, 2.5 units of Pfu DNA polymerase (Stratagene), 4 µl of buffer for Pfu DNA polymerase (10×) (Stratagene) and 200 µmol/l each of deoxyNTPs (dATP, dGTP, dCTP and TTP).

One-tenth of each of the resulting reaction mixtures was subjected to agarose gel electrophoresis to confirm that the desired fragment was amplified. Then, the remaining reaction mixture was mixed with an equal amount of phenol/chloroform (1 vol/1 vol) saturated with TE [10 mmol/l Tris-HCl (pH 8.0), 1 mmol/l EDTA].

The resulting mixture was centrifuged, and the obtained upper layer was mixed with a two-fold volume of cold ethanol and allowed to stand at −80° C. for 30 minutes, followed by centrifugation. By this procedure, chloramphenicol resistance gene-containing DNA fragments for deletion of the pepD, pepN, pepB and pepA genes and the dpp operon were obtained.

(2) Preparation of *Escherichia coli* JM101 Having pepD Gene Deletion

*Escherichia coli* JM101 was transformed with pKD46, spread on LB agar medium containing 100 mg/l ampicillin, and cultured at 30° C. to select a transformant.

The plasmid pKD46 carries an inserted λ Red recombinase gene and is designed so that the expression of the gene is induced by L-arabinose. Accordingly, when *Escherichia coli* grown in the presence of L-arabinose is transformed using a straight-chain DNA, homologous recombination occurs with high frequency. Further, as pKD46 has a thermosensitive replication origin, curing of the plasmid can be readily caused by culturing the strain at 42° C.

The chloramphenicol resistance gene-containing DNA fragment for pepD gene deletion obtained above was introduced into *Escherichia coli* JM101/pKD46 obtained by culturing with addition of 10 mmol/l L-arabinose and 50 µg/ml ampicillin by electroporation. The resulting cells were spread on LB agar medium (10 g/l Bacto-tryptone, 5 g/l Bacto-yeast extract, 5 g/l sodium chloride and 15 g/l agar) containing 25 mg/l chloramphenicol and cultured at 30° C. to select a transformant in which the chloramphenicol resistance gene-containing DNA fragment for pepD gene deletion was integrated into the chromosomal DNA of *Escherichia coli* JM101 by homologous recombination.

The selected chloramphenicol-resistant strain was inoculated onto LB agar medium containing 25 mg/l chloramphenicol and cultured at 42° C. for 14 hours, followed by single colony isolation. Replicas of the obtained colonies were made on LB agar medium containing 25 mg/l chloramphenicol and LB agar medium containing 100 mg/l ampicillin, followed by culturing at 37° C. By selecting a colony showing chloramphenicol resistance and ampicillin sensitivity, a pKD46-cured strain was obtained.

The pKD46-cured strain thus obtained was transformed using pCP20, followed by selection on LB agar medium containing 100 mg/l ampicillin to obtain a pKD46-cured strain carrying pCP20.

The plasmid pCP20 carries an inserted yeast-derived Flp recombinase gene and is designed so that the expression of the gene is induced at a temperature of 42° C.

The chloramphenicol resistance gene-containing DNA fragments for deletion of the pepD, pepN, pepB and pepA genes and the dpp operon prepared above contain nucleotide sequences recognized by Flp recombinase at both termini of the chloramphenicol resistance gene. Therefore, the resistance gene can be readily deleted by homologous recombination catalyzed by Flp recombinase.

Further, as pCP20 has a thermosensitive replication origin, expression of Flp recombinase and curing of pCP20 can be simultaneously induced by culturing the pCP20-carrying strain at 42° C.

The pCP20-carrying pKD46-cured strain obtained above was inoculated onto drug-free LB agar medium and cultured at 42° C. for 14 hours, followed by single colony isolation. Replicas of the obtained colonies were made on drug-free LB agar medium, LB agar medium containing 25 mg/l chloramphenicol and LB agar medium containing 100 mg/l ampicillin, followed by culturing at 30° C. Then, colonies showing chloramphenicol sensitivity and ampicillin sensitivity were selected.

Chromosomal DNAs were prepared from the respective strains selected above according to an ordinary method [Seibutsukogaku Jikkensho (Experiments in Biotechnology), edited by The Society for Biotechnology, Japan, p. 97-98, Baifukan (1992)]. PCR was carried out using, as a set of primers, DNAs having the nucleotide sequences shown in SEQ ID NOS: 49 and 50 which were designed based on an internal nucleotide sequence of the pepD gene to be deleted, and using each of the chromosomal DNAs as a template. PCR was carried out for 30 cycles of 94° C. for one minute, 55° C. for 2 minutes and 72° C. for 3 minutes, using 40 µl of a reaction mixture comprising 0.1 µg of the chromosomal DNA, 0.5 µmol/l each of the primers, 2.5 units of Pfu DNA polymerase, 4 µl of buffer for Pfu DNA polymerase (10×) and 200 µmol/l each of deoxyNTPs.

A strain with which no amplified DNA fragment was detected in the above PCR was identified as a strain having pepD gene deletion and was designated as *Escherichia coli* JPD1.

(3) Preparation of a Strain in which the pepD and pepN Genes on the Chromosomal DNA of *Escherichia coli* JM101 are Deleted

*Escherichia coli* JPD1 obtained in the above (2) was transformed with pKD46, spread on LB agar medium containing 100 mg/l ampicillin, and cultured at 30° C. to select a transformant. The chloramphenicol resistance gene-containing DNA fragment for pepN gene deletion was introduced into the obtained transformant (*Escherichia coli* JPD1/pKD46) by electroporation to obtain a transformant in which the chloramphenicol resistance gene-containing DNA fragment for pepN gene deletion was integrated into the chromosomal DNA of *Escherichia coli* JPD1/pKD46 by homologous recombination.

Subsequently, the same procedure as in the above (2) was carried out to obtain a strain in which the chloramphenicol resistance gene was deleted from the chromosomal DNA, which was designated as *Escherichia coli* JPDN2.

(4) Preparation of Strains in which the pepN, pepA or pepB Gene or the dpp Operon on the Chromosomal DNA of *Escherichia coli* JM101 is Deleted and Strains Having Multiple Gene Deletions The strains having pepN, pepA or pepB gene or dpp operon deletion were prepared according to the same procedure as in the above (2) using the respective chloramphenicol resistance gene-containing DNA fragments for gene or operon deletion prepared in the above (1).

Acquisition of the strains having gene deletions by the above method was confirmed by carrying out PCR in the same manner as in the above (2) using, as sets of primers, DNAs having the nucleotide sequences of SEQ ID NOS: 51 to 58 which were designed and synthesized based on internal nucleotide sequences of the respective genes to be deleted.

That is, DNAs having the following nucleotide sequences were used as respective sets of primers for the confirmation of gene deletion: SEQ ID NOS: 51 and 52 for pepN gene deletion; SEQ ID NOS: 53 and 54 for pepA gene deletion; SEQ ID NOS: 55 and 56 for pepB gene deletion; and SEQ ID NOS: 57 and 58 for dpp operon deletion.

The thus obtained dpp operon-deleted strain, pepN gene-deleted strain, pepA gene-deleted strain and pepB gene-deleted strain were designated as *Escherichia coli* JDPP1, *Escherichia coli* JPN1, *Escherichia coli* JPA1 and *Escherichia coli* JPB7, respectively.

Further, strains having multiple gene deletions, i.e., deletions of two or more genes or operon selected from the group consisting of the pepD, pepN, pepA and pepB genes and the dpp operon were prepared according to the method of the above (3). Acquisition of the strains having multiple gene deletions was confirmed by PCR similar to that in the above (2). The thus obtained double gene-deleted strain having pepD gene and dpp operon deletions was designated as *Escherichia coli* JPDP49, triple gene-deleted strain having pepB, pepD and pepN gene deletions as *Escherichia coli* JPDNB43, triple gene-deleted strain having pepD and pepN gene and dpp operon deletions as *Escherichia coli* JPNDDP36, quadruple gene-deleted strain having pepA, pepD and pepN gene and dpp operon deletions as *Escherichia coli* JPNDAP5, and quadruple gene-deleted strain having pepB, pepD and pepN gene and dpp operon deletions as *Escherichia coli* JPNDBP7. The genes deleted in the gene-deleted strains are shown in Table 2.

TABLE 2

Gene-Deleted Strains and Deleted Genes

| Strain | Deleted gene |
|---|---|
| JM101 | none |
| JDPP1 | dpp operon |
| JPN1 | pepN |
| JPA1 | pepA |
| JPB7 | pepB |
| JPD1 | pepD |
| JPDN2 | pepD, pepN |
| JPNDB43 | pepB, pepD, pepN |
| JPDP49 | pepD, dpp operon |
| JPNDDP36 | pepD, pepN, dpp operon |
| JPNDAP5 | pepA, pepD, pepN, dpp operon |
| JPNDBP7 | pepB, pepD, pepN, dpp operon |

EXPERIMENTAL EXAMPLE 2

Preparation of a Microorganism Having the Ability to Form and Accumulate Amino Acid in which Dipeptidase Genes and Genes of Dipeptide-Incorporating Protein are Deleted Deletion of specific genes on *Escherichia coli* chromosomal DNA was carried out according to the method utilizing the homologous recombination system of lambda phage [Proc. Natl. Acad. Sci. USA, 97, 6641-6645 (2000)].

(1) Cloning of Drug Resistance Gene Fragments for Gene Deletion

The nucleotide sequences of the glnE gene and the glnB gene involved in the regulation of L-glutamine biosynthesis of *Escherichia coli* K12 were already disclosed [Science, 5331, 1453-1474 (1997)].

On the basis of the reported nucleotide sequences, DNAs consisting of the nucleotide sequences of SEQ ID NOS: 59 and 60 to be used as primer DNAs for glnE gene deletion and DNAs consisting of the nucleotide sequences of SEQ ID NOS: 61 and 62 to be used as primer DNAs for glnB gene deletion were synthesized using a DNA synthesizer (Model 8905, PerSeptive Biosystems, Inc.). The synthesized primer DNAs were designed based on the 36-bp nucleotide sequences that lie upstream and downstream of the respective target genes to be deleted.

PCR was carried out using each set of the above synthetic DNAs as a set of primers and pKD3 DNA as a template. PCR was carried out for 30 cycles of 94° C. for one minute, 55° C. for 2 minutes and 72° C. for 3 minutes, using 40 μl of a reaction mixture comprising 10 ng of the plasmid DNA, 0.5 μmol/l each of the primers, 2.5 units of Pfu DNA polymerase, 4 μl of buffer for Pfu DNA polymerase (10×) and 200 μmol/l each of deoxyNTPs.

One-tenth of each of the resulting reaction mixtures was subjected to agarose gel electrophoresis to confirm that the desired fragment was amplified. Then, the remaining reaction mixture was mixed with an equal amount of phenol/chloroform saturated with TE.

The resulting mixture was centrifuged, and the obtained upper layer was mixed with a two-fold volume of cold ethanol and allowed to stand at −80° C. for 30 minutes, followed by centrifugation to precipitate DNA. Then, the DNA precipitate was dissolved in 20 μl of TE. By this procedure, chloramphenicol resistance gene fragments for deletion of the glnE gene and the glnB gene were obtained.

(2) Preparation of *Escherichia coli* JPNDDP36 in which the glnE Gene on the Chromosomal DNA is Deleted

*Escherichia coli* JPNDDP36 obtained in the above (1) was transformed with pKD46, and *Escherichia coli* JPNDDP36 carrying pKD46 (hereinafter referred to as *Escherichia coli* JPNDDP36/pKD46) was selected on LB agar medium containing 100 mg/l ampicillin. *Escherichia coli* JPNDDP36/pKD46 cultured in the presence of 10 mmol/l L-arabinose and 50 μg/ml ampicillin was transformed by electroporation using the chloramphenicol resistance gene fragment for glnE gene deletion, and a recombinant strain in which the chloramphenicol resistance gene was inserted into the glnE gene on the chromosomal DNA of JPNDDP36 strain and the glnE structural gene was deleted was selected on LB agar medium containing 25 mg/l chloramphenicol.

Replicas of the obtained chloramphenicol-resistant strain were made on LB agar medium containing 25 mg/l chloramphenicol, followed by single colony isolation at 42° C. Then, replicas of the obtained colonies were made on LB agar medium containing 25 mg/l chloramphenicol and LB agar medium containing 100 mg/l ampicillin to select a colony showing chloramphenicol resistance and ampicillin sensitivity. The selected pKD46-cured strain was transformed using pCP20, spread on LB agar medium containing 100 mg/l ampicillin, and cultured overnight at 30° C.

Replicas of the ampicillin-resistant strain that grew on the medium were made on drug-free LB agar medium, followed by single colony isolation at 42° C. Then, replicas of the obtained colonies were made on drug-free LB agar medium and LB agar medium containing 25 mg/l chloramphenicol and LB agar medium containing 100 mg/l ampicillin to select colonies showing chloramphenicol sensitivity and ampicillin sensitivity. Chromosomal DNAs were prepared from the respective strains thus obtained according to an ordinary method [Seibutsukogaku Jikkensho (Experiments in Biotechnology), edited by The Society for Biotechnology, Japan, p. 97-98, Baifukan (1992)]. Colony PCR was carried out using primer DNAs consisting of the nucleotide sequences of SEQ ID NOS: 63 and 64 which were designed based on an internal nucleotide sequence of the glnE gene to be deleted. Colony PCR was carried out for 30 cycles of 94° C. for one minute, 55° C. for 2 minutes and 72° C. for 3 minutes, using 40 µl of a reaction mixture comprising the cells in an amount obtained by contacting a 200-µl pipette tip with the colony, 0.5 µmol/l each of the primers, 2.5 units of Pfu DNA polymerase, 4 µl of buffer for Pfu DNA polymerase (10×) and 200 µmol/l each of deoxyNTPs. Of the strains subjected to PCR, a strain with which no gene amplification was detected was identified as a strain having glnE gene deletion and was designated as *Escherichia coli* JPNDDPGLE1.

(3) Preparation of *Escherichia coli* JPNDDP36 in which the glnE and glnB Genes on the Chromosomal DNA are Deleted

*Escherichia coli* JPNDDPGLE1 obtained in the above (2) was transformed with pKD46, spread on LB agar medium containing 100 mg/l ampicillin, and cultured overnight at 30° C. to obtain *Escherichia coli* JPNDDPGLE1 carrying pKD46 (hereinafter referred to as *Escherichia coli* JPNDDPGLE1/pKD46). *Escherichia coli* JPNDDPGLE[1/pKD46 was transformed by electroporation using the chloramphenicol resistance gene fragment for glnB gene deletion to obtain a recombinant strain in which the chloramphenicol resistance gene was inserted into the glnB gene on the chromosomal DNA and the glnB structural gene was deleted. Colony PCR was carried out under the same conditions as in the above (2) using primer DNAs consisting of the nucleotide sequences of SEQ ID NOS: 65 and 66 which were designed based on an internal nucleotide sequence of the glnB gene. A strain with which no gene amplification was detected in the above PCR was identified as a strain having glnB gene deletion and was designated as *Escherichia coli* JPNDDPGBE1.

EXPERIMENTAL EXAMPLE 4

Preparation of Plasmid DNA Expressing a Protein Having the Activity to Form L-Alanyl-L-Glutamine By using a DNA synthesizer (Model 8905, PerSeptive Biosystems, Inc.), DNAs having the nucleotide sequences of SEQ ID NOS: 67 to 70 (hereinafter referred to as primer A, primer B., primer C and primer D, respectively) were synthesized. The sequence shown in SEQ ID NO: 67 is a sequence wherein a sequence containing the XhoI recognition sequence is added to the 5' end of a region containing the Shine-Dalgarno sequence (ribosome binding sequence) of the ywfE gene on plasmid pQE60ywfE produced by the method described in WO2004/058960. The sequence of SEQ ID NO: 68 is a sequence wherein a sequence containing the BamHI recognition sequence is added to the 5' end of a sequence complementary to a sequence containing the termination codon of the ywfE gene.

The sequence of SEQ ID NO: 69 is a sequence wherein a sequence containing the EcoRI recognition sequence is added to the 5' end of the sequence of the trp promoter region of expression vector pTrS30 containing the trp promoter. The sequence of SEQ ID NO: 70 is a sequence wherein a sequence containing the XhoI recognition sequence is added to the 5' end of a sequence complementary to the sequence of the trp promoter region of expression vector pTrS30 containing the trp promoter.

PCR was carried out using plasmid pQE60ywfE as a template and the above primer A and primer B for amplification of a ywfE gene fragment, and primer C and primer D for amplification of a trp promoter region fragment, as respective sets of primers. PCR was carried out for 30 cycles of 94° C. for one minute, 55° C. for 2 minutes and 72° C. for 3 minutes, using 40 µl of a reaction mixture comprising 10 ng of pQE60ywfE, 0.5 µmol/l each of the primers, 2.5 units of Pfu DNA polymerase, 4 µl of buffer for Pfu DNA polymerase (10×) and 200 µmol/l each of dNTPs.

One-tenth of each of the resulting reaction mixtures was subjected to agarose gel electrophoresis to confirm that a ca. 1.4 kb fragment corresponding to the ywfE gene fragment was amplified by PCR using primer A and primer B, and a ca. 0.3 kb fragment corresponding to the trp promoter region fragment was amplified by PCR using primer C and primer D. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. for 30 minutes. The resulting solution was centrifuged, and the obtained DNA was dissolved in 20 µl of TE.

The thus obtained DNA solutions (5 µl each) were respectively subjected to reaction to cleave the DNA amplified using primer A and primer B with restriction enzymes XhoI and BamHI and to reaction to cleave the DNA amplified using primer C and primer D with restriction enzymes EcoRI and XhoI. DNA fragments were separated by agarose gel electrophoresis, and a 1.4 kb DNA fragment containing the ywfE gene and a 0.3 kb DNA fragment containing the trp promoter region were respectively recovered using GENECLEAN II Kit.

Expression vector pTrS30 containing trp promoter (0.2 µg) was cleaved with restriction enzymes EcoRI and BamHI. DNA fragments were separated by agarose gel electrophoresis, and a 4.5 kb DNA fragment was recovered in the same manner as above.

The 1.4 kb fragment containing the ywfE gene, the 0.3 kb fragment containing the trp promoter region and the 4.5 kb fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 50 µg/ml ampicillin, and cultured overnight at 30° C.

A plasmid was extracted from a colony of the transformant that grew on the medium according to a known method. By restriction enzyme digestion, it was confirmed that the plasmid was an expression plasmid carrying the ywfE gene at a position downstream of the trp promoter, and the plasmid was designated as pPE56.

On the basis of the expression plasmid pPE56, an expression plasmid which constitutively expresses an alanine dehydrogenase gene (ald gene) derived from *Bacillus subtilis* at the same time was constructed in the following manner.

By using a DNA synthesizer (Model 8905, PerSeptive Biosystems, Inc.), DNAs having the nucleotide sequences of SEQ ID NOS: 71 and 72 (hereinafter referred to as primer E and primer F, respectively) were synthesized. The sequence of SEQ ID NO: 71 is a sequence wherein a sequence containing the BamHI recognition sequence is added to the 5' end of a region containing the Shine-Dalgarno sequence (ribosome binding sequence) of the ald gene. The sequence of SEQ ID NO: 72 is a sequence wherein a sequence containing the BamHI recognition sequence is added to the 5' end of a sequence complementary to a sequence containing the termination codon of the ald gene.

PCR was carried out using the chromosomal DNA of *Bacillus subtilis* as a template and the above primer E and primer F as a set of primers. PCR was carried out for 30 cycles of 94° C. for one minute, 55° C. for 2 minutes and 72° C. for 3 minutes, using 40 µl of a reaction mixture comprising 0.1 µg of the chromosomal DNA, 0.5 µmol/l each of the primers, 2.5 units of Pfu DNA polymerase, 4 µl of buffer for Pfu DNA polymerase (10×) and 200 µmol/l each of dNTPs.

One-tenth of the resulting reaction mixture was subjected to agarose gel electrophoresis to confirm that a ca. 1.2 kb fragment corresponding to the ald gene fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

The thus obtained solution (5 µl) was subjected to reaction to cleave the amplified DNA with restriction enzyme BamHI. DNA fragments were separated by agarose gel electrophoresis, and a 1.2 kb DNA fragment containing the ald gene was recovered using GENECLEAN II Kit.

pPE56 (0.2 µg) was cleaved with restriction enzyme BamHI. DNA fragments were separated by agarose gel electrophoresis, and a 6.3 kb DNA fragment was recovered in the same manner as above. Dephosphorylation of the end of the 6.3 kb DNA fragment was carried out by treatment with alkaline phosphatase (*E. coli* C75, Takara Bio Inc.) at 60° C. for 30 minutes. The reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

The 1.2 kb DNA fragment containing the ald gene and the alkaline phosphatase-treated 6.3 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 50 µg/ml ampicillin, and cultured overnight at 30° C.

A plasmid was extracted from a colony of the transformant that grew on the medium according to a known method. By restriction enzyme digestion, it was confirmed that a plasmid into which the ald gene was inserted in the same direction as the ywfE gene was obtained, and the plasmid was designated as pPE86.

EXPERIMENTAL EXAMPLE 5

Preparation of a Microorganism Having the Ability to Produce a Protein Having the Activity to Form a Dipeptide and the Ability to Form L-Alanine and L-Glutamine in which Dipeptidase Genes and Dipeptide-Incorporating Genes are Deleted

*Escherichia coli* JPNDDPGBE1 obtained in the above Experimental Example 2 was transformed with pPE86 prepared in the above Experimental Example 4 to obtain *Escherichia coli* JPNDDPGBE1/pPE86 carrying the plasmid.

Certain embodiments of the present invention are illustrated in the following examples. These examples are not to be construed as limiting the scope of the present invention.

EXAMPLE 1

Fermentative Production of L-Alanyl-L-Glutamine

*Escherichia coli* JPNDDPGBE1/pPE86 obtained in the above Experimental Example 5 was inoculated into LB medium (10 g/l tryptone, 5 g/l yeast extract and 5 g/l sodium chloride) containing 50 µg/ml ampicillin in a test tube and cultured at 28° C. for 17 hours. The resulting culture was added to TF medium (16 g/l disodium hydrogenphosphate, 14 g/l potassium dihydrogenphosphate, 5 g/l ammonium sulfate, 1 g/l citric acid, 0.5 g/l Casamino acid, 1 g/l proline, 2.5 g/l alanine, 2.5 g/l glutamine, 10 mg/l vitamin B1, 25 mg/l magnesium sulfate, 50 mg/l ferrous sulfate and 10 g/l glucose) containing 100 µg/ml ampicillin in an amount of 1% and cultured at 30° C. for 24 hours.

After the completion of the culturing, the culture supernatant was derivatized by the F-moc method and then analyzed by HPLC. The HPLC analysis was carried out using ODS-HG5 (Nomura Chemical Co., Ltd.) as a separation column and, as eluents, solution A [6 ml/l acetic acid and 20% (v/v) acetonitrile, adjusted to pH 4.8 with triethylamine] and solution B [6 ml/l acetic acid and 70% (v/v) acetonitrile, adjusted to pH 4.8 with triethylamine]. The ratio of solution A to solution B was 8:2 during the first 5 minutes of analysis, and from minute 5 to minute 20, the ratio of solution B was increased with a linear gradient so that the A:B ratio became 1:1 at minute 20. As a result, it was confirmed that 1 g/l alanylglutamine was accumulated in the culture supernatant.

EXAMPLE 2

Production of Crystals of L-Alanyl-L-Glutamine

*Escherichia coli* JPNDDPGBE1/pPE86 was inoculated into LB medium containing 50 µg/ml ampicillin in an Erlenmeyer flask and cultured at 28° C. for 24 hours. The obtained culture (50 ml) was added to 1.95 l of JF medium (6 g/l disodium hydrogenphosphate, 3 g/l potassium dihydrogenphosphate, 5 g/l sodium chloride, 5 g/l yeast extract, 2 g/l magnesium sulfate, 0.2 g/l ferrous sulfate, 0.01 g/l manganese sulfate, 1 g/l ammonium chloride, 0.2 g/l proline, 0.01 g/l thiamine hydrochloride and 10 g/l glucose) in a 6-l jar, followed by culturing at 32° C. with aeration and agitation. During the culturing, glucose, L-glutamine and L-alanine were appropriately added and the culture was maintained at pH 6.6 to 7.0 with aqueous ammonia. Culturing was carried out for 60 hours and L-alanyl-L-glutamine was accumulated in the culture.

The obtained culture containing L-alanyl-L-glutamine was adjusted to pH 3 by addition of hydrochloric acid and then heated at 80° C. for one hour to degrade the remaining glutamine. The culture was cooled to room temperature and centrifuged to remove the cells. The obtained supernatant was passed through a column packed with a strongly acidic cation exchange resin (MARATHON C, The Dow Chemical Company) (loading: 1.6 ml supernatant/ml resin) to adsorb L-alanyl-L-glutamine onto the resin. After the resin was sufficiently washed with water, L-alanyl-L-glutamine was eluted with 0.7 mol/l sodium hydroxide to obtain a fraction containing L-alanyl-L-glutamine.

The fraction was passed through a column packed with a weakly acidic cation exchange resin (IRC50, Rohm and Haas) (loading: 10 ml fraction/ml resin) to adsorb L-alanyl-L-glutamine. Then water was passed through the column to elute L-alanyl-L-glutamine, whereby a fraction containing L-alanyl-L-glutamine was obtained.

The fraction was passed through a column packed with a strongly basic anion exchange resin (PA412, Mitsubishi Chemical Corporation) (loading: 23 ml fraction/ml resin) to adsorb L-alanyl-L-glutamine, and then water was passed through the column to obtain a fraction containing L-alanyl-L-glutamine.

The fraction was concentrated under reduced pressure to obtain a concentrated solution of L-alanyl-L-glutamine having a concentration of ca. 450 g/l. The solution was adjusted to pH 5.7 with hydrochloric acid, and methanol was added thereto with gentle stirring at 60° C. When the methanol concentration became ca. 33%, crystals of L-alanyl-L-glutamine were added as seed crystals in an amount of 2.5% by weight based on the weight of L-alanyl-L-glutamine contained in the concentrated solution. Methanol was further added until the methanol concentration reached 80%. Then, the methanol solution was cooled to 20° C., and the formed crystals were separated by filtration to obtain crude crystals.

The crude crystals were dissolved in water, and the resulting solution was passed through a column packed with a weakly basic anion exchange resin (WA30, Mitsubishi Chemical Corporation) (loading: 2800 ml solution/ml resin) to adsorb L-alanyl-L-glutamine. Then water was passed through the column to elute L-alanyl-L-glutamine, whereby a fraction containing L-alanyl-L-glutamine was obtained.

The fraction was concentrated in the same manner as above and methanol was added thereto for crystallization. The obtained crystals were filtered and dried to obtain a purified preparation of L-alanyl-L-glutamine as needle crystals.

The analysis result of the crystals is shown below. For measurement of the optical rotation, HORIBA SEPA-200 (HORIBA, Ltd.) was used, and RAD-X (Rigaku Corporation) was used for powder X-ray diffraction analysis. Measurement was carried out according to the manuals of respective apparatus.

Optical rotation (20° C.) of purified preparation: +9.7° Powder X-ray diffraction (diffraction angle: $2\theta°$) [the number in parenthesis indicates the relative intensity ratio $(I/I_0)$]: 6.80 (4), 11.10(2), 13.70(100), 18.60(4), 19.55(5), 20.65(75), 21.36(17), 21.60(9), 22.45(14), 23.25(8), 24.05(4), 24.75(3), 25.45(12), 26.00(2), 27.55(6), 29.85(3), 30.45(2), 32.40(2), 32.95(2), 33.95(2), 34.80(25), 35.15(3), 36.45(7), 36.80(3), 42.55(2), 43.40(2)

Impurities contained in the crystals of L-alanyl-L-glutamine obtained above were analyzed in the same manner as in Reference Example. The results are shown in Table 3.

TABLE 3

Analysis Result of Substances Contained in the Crystals of L-Alanyl-L-Glutamine

| | HPLC purity (upper row: area %, lower row: weight %) | | | |
|---|---|---|---|---|
| | L-Ala-L-Gln | DL form | AlaAlaGln | AlaNH$_2$ |
| L-alanyl-L-glutamine crystals of the present invention | 99.92<br>99.92 | ND | ND | ND |

In the table, ND indicates a value below the detection limit (area %: 0.002%) and DL form indicates D-alanyl-L-glutamine.

As can be seen from Table 3, the crystals of L-alanyl-L-glutamine of the present invention did not comprise DL form, alanyl-alanyl-glutamine or alanine amide. That is, dipeptide crystals which do not substantially comprise a dipeptide comprising D-amino acid as a constituent or a polypeptide consisting of three or more amino acids were obtained.

EXAMPLE 3

Effect of Methanol Crystallization

The crude crystals of L-alanyl-L-glutamine obtained in Example 2 (comprising 0.111% alanyl-alanyl-glutamine) were dissolved in water, and the resulting solution was fractionated using WA30 resin and then concentrated in the same manner as in Example 2. After the obtained concentrated solution was divided into two portions, crystallization of L-alanyl-L-glutamine was carried out. That is, methanol was added to one portion in the same manner as in Example 2, and the other portion was treated in the same manner as in Example 2 except that ethanol was added instead of methanol until the ethanol concentration reached 75%.

The obtained crystals were dried and the amount of alanyl-alanyl-glutamine was measured in the same manner as in Reference Example. The results are shown in Table 4.

TABLE 4

Effect of Crystallization with Methanol and Ethanol

| Solvent for crystallization | HPLC area % | | Crystallization rate (%) of L-Ala-L-Gln |
|---|---|---|---|
| | L-Ala-L-Gln | AlaAlaGln | |
| Methanol | 99.9 | 0.004 | 96.1 |
| Ethanol | 99.9 | 0.014 | 97.2 |

The crystallization rate in the table indicates values calculated by the formula: [(amount of L-Ala-L-Gln in the solution before addition of the solvent)−(amount of L-Ala-L-Gln remaining in the supernatant after crystallization)]/(amount of L-Ala-L-Gln in the solution before addition of the solvent)×100.

The results shown in Table 4 revealed that alanyl-alanyl-glutamine can be efficiently removed from the crystals of L-alanyl-L-glutamine by crystallizing L-alanyl-L-glutamine using methanol.

INDUSTRIAL APPLICABILITY

The present invention can provide dipeptide crystals which do not substantially comprise a dipeptide comprising D-amino acid as a constituent or a polypeptide consisting of three or more amino acids.

SEQUENCE LISTING FREE TEXT
SEQ ID NO: 38—Description of Artificial Sequence: Synthetic DNA
SEQ ID NO: 39—Description of Artificial Sequence: Synthetic DNA
SEQ ID NO: 40—Description of Artificial Sequence: Synthetic DNA
SEQ ID NO: 41—Description of Artificial Sequence: Synthetic DNA
SEQ ID NO: 42—Description of Artificial Sequence: Synthetic DNA
SEQ ID NO: 43—Description of Artificial Sequence: Synthetic DNA
SEQ ID NO: 44—Description of Artificial Sequence: Synthetic DNA
SEQ ID NO: 45—Description of Artificial Sequence: Synthetic DNA
SEQ ID NO: 46—Description of Artificial Sequence: Synthetic DNA
SEQ ID NO: 47—Description of Artificial Sequence: Synthetic DNA
SEQ ID NO: 48—Description of Artificial Sequence: Synthetic DNA
SEQ ID NO: 49—Description of Artificial Sequence: Synthetic DNA
SEQ ID NO: 50—Description of Artificial Sequence: Synthetic DNA
SEQ ID NO: 51—Description of Artificial Sequence: Synthetic DNA
SEQ ID NO: 52—Description of Artificial Sequence: Synthetic DNA
SEQ ID NO: 53—Description of Artificial Sequence: Synthetic DNA
SEQ ID NO: 54—Description of Artificial Sequence: Synthetic DNA
SEQ ID NO: 55—Description of Artificial Sequence: Synthetic DNA
SEQ ID NO: 56—Description of Artificial Sequence: Synthetic DNA
SEQ ID NO: 57—Description of Artificial Sequence: Synthetic DNA
SEQ ID NO: 58—Description of Artificial Sequence: Synthetic DNA
SEQ ID NO: 59—Description of Artificial Sequence: Synthetic DNA
SEQ ID NO: 60—Description of Artificial Sequence: Synthetic DNA
SEQ ID NO: 61—Description of Artificial Sequence: Synthetic DNA
SEQ ID NO: 62—Description of Artificial Sequence: Synthetic DNA
SEQ ID NO: 63—Description of Artificial Sequence: Synthetic DNA
SEQ ID NO: 64—Description of Artificial Sequence: Synthetic DNA
SEQ ID NO: 65—Description of Artificial Sequence: Synthetic DNA
SEQ ID NO: 66—Description of Artificial Sequence: Synthetic DNA
SEQ ID NO: 67—Description of Artificial Sequence: Synthetic DNA
SEQ ID NO: 68—Description of Artificial Sequence: Synthetic DNA
SEQ ID NO: 69—Description of Artificial Sequence Synthetic DNA
SEQ ID NO: 70—Description of Artificial Sequence: Synthetic DNA
SEQ ID NO: 71—Description of Artificial Sequence: Synthetic DNA
SEQ ID NO: 72—Description of Artificial Sequence: Synthetic DNA

The invention claimed is:

1. A crystal of L-alanyl-L-glutamine that is at least 99.91% pure as determined by high performance liquid chromatography (HPLC), wherein the total weight percent of D-alanyl-L-glutamine in the crystal is less than 0.002 as determined by HPLC, the total weight percent of AlaAlaGln in the crystal is less than 0.002 as determined by HPLC, and wherein the total weight percent of alanine amide in the crystal is less than 0.002 as determined by HPLC.

* * * * *

```
                         SEQUENCE LISTING

<160> NUMBER OF SEQ ID NOS: 72

<210> SEQ ID NO 1
<211> LENGTH: 472
<212> TYPE: PRT
<213> ORGANISM: Bacillus subtilis 168

<400> SEQUENCE: 1

Met Glu Arg Lys Thr Val Leu Val Ile Ala Asp Leu Gly Gly Cys Pro
 1               5                  10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Glu Val Val Glu Gln Ile Val Lys Val Ala
                85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125
```

```
Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
210                 215                 220

Ala Glu Glu Phe Leu Gln Gly Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Ala Lys Lys
        275                 280                 285

Lys Ile Val Glu Ala Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
450                 455                 460

Thr Ala Lys Tyr Val Leu Pro Val
465                 470

<210> SEQ ID NO 2
<211> LENGTH: 472
<212> TYPE: PRT
<213> ORGANISM: Bacillus subtilis ATCC6633

<400> SEQUENCE: 2

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30
```

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Gln Ser
        50                  55                  60

Leu Ala Asp Phe Glu His Pro Asp Ser Ile Tyr Trp Ala His Glu Asp
65                  70                  75                  80

His Asp Lys Pro Glu Glu Val Val Glu Gln Ile Val Lys Val Ala
                85                  90                  95

Gln Met Phe Glu Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
            130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
            195                 200                 205

Lys Ser Ile Asn Val Pro Lys Ala Val Thr Phe Glu Ala Pro Phe Ile
210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
            275                 280                 285

Lys Ile Val Glu Ala Ala Lys Lys Ala Asn Glu Gly Leu Gly Leu Gln
            290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
            355                 360                 365

Gln Glu Pro Tyr Tyr Val Ala Asp Cys His Leu Tyr Pro Gln His Phe
            370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Thr Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
            435                 440                 445

Gln Asp Val Ala Glu Ser Ile Arg Gln Ile Gln Gln His Ala Lys Leu

```
                    450                 455                 460
Thr Ala Lys Tyr Val Leu Pro Val
465                 470

<210> SEQ ID NO 3
<211> LENGTH: 472
<212> TYPE: PRT
<213> ORGANISM: Bacillus subtilis IAM1213

<400> SEQUENCE: 3

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
        50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Lys Ala
                85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
    290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
```

```
                    355                 360                 365
Gln Glu Pro Tyr Tyr Val Ala Asp Cys His Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Leu Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
                420                 425                 430

Glu Ala Phe Asn Ser Ile Ala Ala Phe Glu Leu Lys Gly Ser Asn Ser
                435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470

<210> SEQ ID NO 4
<211> LENGTH: 472
<212> TYPE: PRT
<213> ORGANISM: Bacillus subtilis IAM1107

<400> SEQUENCE: 4

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Val Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Asn Glu Leu Phe Ile
                100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
```

```
                    260                 265                 270
Glu Thr Ser His Ile Thr Pro Ser Ile Leu Asp Glu Ala Lys Lys
                275                 280                 285

Lys Ile Val Glu Ala Ala Lys Lys Ala Asn Glu Gly Leu Gly Leu Gln
            290                 295                 300

Asn Cys Ala Thr His Thr Glu Val Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
            355                 360                 365

Gln Glu Pro Tyr Tyr Val Ala Asp Cys His Leu Tyr Pro Gln His Phe
            370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Phe
                405                 410                 415

Ser Phe Ser Ala Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
            435                 440                 445

Gln Asp Val Ala Glu Ser Ile Arg Gln Ile Gln Gln His Ala Lys Leu
            450                 455                 460

Thr Ala Lys Tyr Val Leu Pro Val
465                 470

<210> SEQ ID NO 5
<211> LENGTH: 472
<212> TYPE: PRT
<213> ORGANISM: Bacillus subtilis IAM1214

<400> SEQUENCE: 5

Met Glu Arg Lys Thr Val Leu Val Ile Ala Asp Leu Gly Gly Cys Pro
  1               5                  10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Gln Ser
        50                  55                  60

Leu Ala Asp Phe Glu His Pro Asp Ser Ile Tyr Trp Ala His Glu Asp
 65                  70                  75                  80

His Asp Lys Pro Glu Glu Glu Val Val Glu Gln Ile Val Lys Val Ala
                85                  90                  95

Gln Met Phe Glu Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
```

```
                        165                 170                 175
Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
            245                 250                 255

Tyr Phe Pro Ile Ala Ile His Asp Lys Thr Pro Gln Ile Gly Phe Thr
        260                 265                 270

Glu Thr Ser His Ile Thr Pro Ser Ile Leu Asp Glu Glu Ala Lys Lys
    275                 280                 285

Lys Ile Val Glu Ala Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
            325                 330                 335

Asn Ile Lys Lys Val Phe Gly Leu Asp Met Ala Gln Leu Leu Leu Asp
        340                 345                 350

Val Leu Cys Phe Gly Lys Asp Ala Asp Leu Pro Asp Gly Leu Leu Asp
    355                 360                 365

Gln Glu Pro Tyr Tyr Val Ala Asp Cys His Leu Tyr Pro Gln His Phe
370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
            405                 410                 415

Thr Phe Ser Ala Ala Pro Gly Thr Ser Val Asp Leu Thr Leu Phe
        420                 425                 430

Glu Ala Phe Asn Ser Ile Ala Ala Phe Glu Leu Lys Gly Ser Asn Ser
    435                 440                 445

Gln Asp Val Ala Glu Ser Ile Arg Gln Ile Gln Gln His Ala Lys Leu
450                 455                 460

Thr Ala Lys Tyr Val Leu Pro Val
465                 470

<210> SEQ ID NO 6
<211> LENGTH: 472
<212> TYPE: PRT
<213> ORGANISM: Bacillus subtilis ATCC21555

<400> SEQUENCE: 6

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Ile Ala Val Ile Lys Asp Lys Asp Tyr Phe Lys Ser
    50                  55                  60

Leu Ala Asp Phe Glu His Pro Asp Ser Ile Tyr Trp Ala His Glu Asp
```

```
               65                  70                  75                  80
        His Asp Lys Pro Glu Glu Val Val Glu Ile Val Lys Val Ala
                            85                  90                  95

Asp Met Phe Gly Val Asp Ala Ile Thr Thr Asn Asn Glu Leu Phe Ile
                        100                 105                 110

Ala Pro Met Ala Lys Ala Cys Lys Arg Leu Gly Leu Arg Gly Ala Gly
                        115                 120                 125

Val Gln Ala Ala Glu Asn Ala Arg Asp Lys Asn Lys Met Arg Ala Ala
                        130                 135                 140

Phe Asn Arg Ala Gly Val Lys Ser Ile Lys Asn Lys Arg Val Thr Thr
        145                 150                 155                 160

Leu Glu Asp Phe Arg Ala Ala Leu Gln Glu Ile Gly Thr Pro Leu Ile
                        165                 170                 175

Leu Lys Pro Thr Tyr Leu Ala Ser Ser Ile Gly Val Thr Leu Ile Lys
                        180                 185                 190

Glu Met Glu Thr Ala Glu Ala Glu Phe Asn Arg Val Asn Glu Tyr Leu
                        195                 200                 205

Lys Ser Ile Asn Val Pro Lys Ala Val Thr Phe Glu Ala Pro Phe Ile
                        210                 215                 220

Ala Glu Glu Phe Leu Gln Gly Glu Tyr Asp Asp Trp Tyr Glu Thr Ser
        225                 230                 235                 240

Gly Tyr Ser Asp Tyr Ile Ser Ile Glu Gly Ile Met Ala Asp Gly Glu
                        245                 250                 255

Tyr Phe Pro Val Ala Ile His Asp Lys Thr Pro Gln Ile Gly Phe Thr
                        260                 265                 270

Glu Thr Ala His Ile Thr Pro Ser Ile Leu Asp Asp Ala Lys Arg
                        275                 280                 285

Lys Ile Val Glu Ala Ala Lys Lys Ala Asn Glu Gly Leu Gly Leu Glu
                        290                 295                 300

Asn Cys Ala Thr His Thr Glu Ile Lys Leu Met Lys Asn Arg Glu Ala
        305                 310                 315                 320

Gly Leu Ile Glu Ser Ala Ala Arg Phe Ala Gly Trp Asn Met Ile Pro
                        325                 330                 335

Asn Ile Lys Lys Val Phe Gly Val Asp Met Ala Gln Leu Leu Leu Asp
                        340                 345                 350

Val Leu Cys Tyr Gly Lys Glu Ala Asp Leu Pro Lys Gly Leu Leu Glu
                        355                 360                 365

Gln Glu Pro Cys Tyr Val Ala Asp Cys His Leu Tyr Pro Gln His Phe
                        370                 375                 380

Lys Glu Asn Gly Gln Leu Pro Glu Thr Val Val Asp Phe Val Ile Glu
        385                 390                 395                 400

Ser Ile Glu Ile Pro Asp Gly Val Leu Lys Gly Asp Thr Glu Leu Val
                        405                 410                 415

Ser Phe Ser Ala Ala Glu Ala Gly Thr Ser Val Asp Leu Arg Leu Phe
                        420                 425                 430

Glu Ala Phe Asn Ser Ile Ala Ala Phe Glu Leu Lys Gly Ser Asn Ser
                        435                 440                 445

Asn Asp Val Ala Glu Ser Ile Lys Gln Ile Gln Gln Ala Lys Leu
                        450                 455                 460

Thr Ala Lys Tyr Ala Leu Ser Val
        465                 470

<210> SEQ ID NO 7
<211> LENGTH: 472
```

```
<212> TYPE: PRT
<213> ORGANISM: Bacillus amyloliquefaciens IFO3022

<400> SEQUENCE: 7

Met Glu Arg Lys Thr Val Leu Val Ile Ala Asp Leu Gly Gly Cys Pro
 1               5                  10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asp Lys Pro Glu Glu Val Val Glu Ile Val Lys Val Ala
                85                  90                  95

Gly Met Phe Ala Val Asp Ala Ile Thr Thr Asn Asn Glu Leu Phe Ile
                100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Ala Ala
130                 135                 140

Phe Asn Arg Ala Gly Val Lys Ser Ile Lys Asn Arg Val Thr Thr
145                 150                 155                 160

Leu Glu Asp Phe Arg Ala Ala Leu Gln Glu Ile Gly Thr Pro Leu Ile
                165                 170                 175

Leu Lys Pro Thr Tyr Leu Ala Ser Ser Ile Gly Val Thr Leu Ile Lys
            180                 185                 190

Glu Arg Glu Thr Ala Glu Ala Glu Phe Asn Arg Val Asn Glu Tyr Leu
    195                 200                 205

Lys Ser Ile Asn Val Pro Lys Ala Val Thr Phe Glu Ala Pro Phe Ile
210                 215                 220

Ala Glu Glu Phe Leu Gln Gly Glu Tyr Asp Asp Trp Tyr Glu Thr Ser
225                 230                 235                 240

Gly Tyr Ser Asp Tyr Ile Ser Ile Glu Gly Ile Met Ala Asp Gly Glu
                245                 250                 255

Tyr Phe Pro Val Ala Ile His Asp Lys Thr Pro Gln Ile Gly Phe Thr
            260                 265                 270

Glu Thr Ser His Ile Thr Pro Ser Ile Leu Asp Asp Ala Lys Arg
    275                 280                 285

Lys Ile Val Glu Ala Ala Lys Lys Ala Asn Glu Gly Leu Gly Leu Glu
290                 295                 300

Asn Cys Ala Thr His Thr Glu Ile Lys Leu Met Lys Asn Arg Glu Ala
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Val Asp Met Ala Gln Leu Leu Leu Asp
            340                 345                 350

Val Leu Cys Phe Gly Lys Glu Ala Asp Leu Pro Lys Gly Leu Leu Glu
    355                 360                 365

Gln Glu Pro Cys Tyr Val Ala Asp Cys His Leu Tyr Pro Gln His Phe
370                 375                 380

Lys Glu Asn Gly Gln Leu Pro Thr Ala Val Asp Phe Val Ile Glu
385                 390                 395                 400
```

-continued

```
Ser Ile Asp Ile Pro Asp Gly Val Leu Lys Gly Asp Thr Glu Ile Val
            405                 410                 415

Ser Phe Ser Ala Glu Ala Gly Thr Ser Val Asp Leu Arg Leu Phe
        420                 425                 430

Glu Ala Phe Asn Ser Ile Ala Ala Phe Glu Leu Lys Gly Ser Asn Ser
        435                 440                 445

Gly Asp Val Ala Glu Ser Ile Lys Gln Ile Gln Gln Ala Lys Leu
450                 455                 460

Thr Ala Lys Tyr Ala Leu Pro Val
465                 470
```

<210> SEQ ID NO 8
<211> LENGTH: 476
<212> TYPE: PRT
<213> ORGANISM: Bacillus pumilus NRRL B-12025

<400> SEQUENCE: 8

```
Val Leu Ser Leu Ser Lys Lys Thr Val Leu Val Ile Ala Asp Leu Gly
1               5                   10                  15

Gly Cys Pro Pro His Met Phe Tyr Glu Ser Val Ala Ala Ser Tyr His
                20                  25                  30

Ile Val Ser Tyr Ile Pro Arg Pro Phe Ala Ile Thr Lys Gly His Ala
            35                  40                  45

Glu Leu Ile Glu Lys Tyr Ser Ile Ala Val Ile Lys Asp Arg Asp Tyr
        50                  55                  60

Phe Glu Thr His Pro Ser Phe Glu His Pro Asp Ser Ile Tyr Trp Ala
65                  70                  75                  80

His Asp Asp Tyr Pro Lys Ser Glu Glu Val Val Glu Asp Phe Ile
                85                  90                  95

Arg Val Ala Ser Phe Phe Lys Ala Asp Ala Ile Thr Thr Asn Asn Glu
            100                 105                 110

Leu Phe Ile Ala Pro Met Ala Lys Ala Ala Glu Arg Leu Gly Leu Arg
        115                 120                 125

Gly Ala Gly Val Lys Ala Ala Glu Met Ala Arg Asp Lys Ser Gln Met
    130                 135                 140

Arg Ala Ala Phe Asn Ala Ser Gly Val Lys Ala Val Lys Thr Gln Pro
145                 150                 155                 160

Val Thr Thr Leu Ser Asp Phe Gln Gln Ala Ile Glu Ser Ile Gly Thr
                165                 170                 175

Pro Leu Ile Leu Lys Pro Thr Tyr Leu Ala Ser Ser Ile Gly Val Thr
            180                 185                 190

Leu Phe His Asp Lys Ala Gly Ser Asp Asp Leu Phe Leu Gln Val Gln
        195                 200                 205

Ser Tyr Leu Glu Thr Ile Pro Val Pro Asp Ala Val Thr Tyr Glu Ala
    210                 215                 220

Pro Phe Val Ala Glu Thr Tyr Leu Glu Gly Ala Tyr Glu Asp Trp Tyr
225                 230                 235                 240

Glu Asp Glu Gly Tyr Ala Asp Tyr Val Ser Val Glu Gly Leu Val Val
                245                 250                 255

Glu Gly Glu Tyr Leu Pro Phe Val Ile His Asp Lys Thr Pro Gln Ile
            260                 265                 270

Gly Phe Thr Glu Thr Ala His Ile Thr Pro Thr Ile Leu Asp Asn Glu
        275                 280                 285

Ala Lys Gln Ile Ile Ile Glu Ala Ala Arg Lys Ala Asn Glu Gly Leu
    290                 295                 300
```

```
Gly Leu Glu His Cys Ala Thr His Thr Glu Ile Lys Leu Met Lys Asn
305                 310                 315                 320

Arg Glu Thr Gly Leu Ile Glu Ala Ala Ala Arg Phe Ala Gly Trp Asn
                325                 330                 335

Met Ile Pro Asn Ile Lys Lys Val Phe Gly Val Asp Met Ala Lys Leu
            340                 345                 350

Leu Ile Asp Val Leu Val Asp Gly Lys Lys Ala Val Leu Pro Lys Gln
        355                 360                 365

Leu Leu Ser Gly His Thr Phe Tyr Val Ala Asp Cys His Leu Tyr Pro
370                 375                 380

Gln His Phe Lys Glu Ser Gly Leu Ile Pro Pro Glu Ala Thr His Ile
385                 390                 395                 400

Thr Ile Asp His Val Ser Ile Pro Gln Glu Ala Phe Val Gly Asp Thr
                405                 410                 415

Ala Ile Val Ser Gln Ser Phe Pro Ala Lys Gly Thr Ile Val Asp Leu
            420                 425                 430

Glu Leu Phe Glu Ala Phe Asn Gly Ile Val Ser Leu Glu Leu Lys Gly
        435                 440                 445

Ser Ser Ser Gln Asp Val Ala Ala Ser Ile Arg Asn Ile Gln Lys Gln
450                 455                 460

Ala Thr Ile Gln Leu Met Asp Glu Leu Val Lys Gly
465                 470                 475

<210> SEQ ID NO 9
<211> LENGTH: 1416
<212> TYPE: DNA
<213> ORGANISM: Bacillus subtilis 168

<400> SEQUENCE: 9 atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
                20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
            35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
        50                  55                  60 tta gct gat ttt gaa cac cct gat tcc att tat tgg gcg cat gaa gat     240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc     288
His Asn Lys Pro Glu Glu Glu Val Val Glu Gln Ile Val Lys Val Ala
                85                  90                  95 gaa atg ttt ggg gcg gat gcc atc aca aca aac aat gaa tta ttc att     336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ttg aga ggt gcc ggc     384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct     432
Val Gln Ala Ala Glu Asn Ala Arg Asp Lys Asn Lys Met Arg Asp Ala
130                 135                 140 ttt aat aag gcc gga gtc aaa tcg atc aaa aac aaa cga gtc aca act     480
Phe Asn Lys Ala Gly Val Lys Ser Ile Lys Asn Lys Arg Val Thr Thr
145                 150                 155                 160
```

```
ctt gaa gat ttc cgt gct gct ctt gaa gag atc ggc aca cct ctt atc      528
Leu Glu Asp Phe Arg Ala Ala Leu Glu Glu Ile Gly Thr Pro Leu Ile
            165                 170                 175 tta aag cct aca tac tta gcg agt tct atc ggt gta acg ctg att acg      576
Leu Lys Pro Thr Tyr Leu Ala Ser Ser Ile Gly Val Thr Leu Ile Thr
        180                 185                 190 gac act gag acg gca gaa gat gaa ttt aac aga gtc aat gac tat ctg      624
Asp Thr Glu Thr Ala Glu Asp Glu Phe Asn Arg Val Asn Asp Tyr Leu
    195                 200                 205 aaa tca att aac gtg cca aag gcg gtt acg ttt gaa gcg ccg ttt atc      672
Lys Ser Ile Asn Val Pro Lys Ala Val Thr Phe Glu Ala Pro Phe Ile
210                 215                 220 gct gaa gaa ttt tta cag ggt gag tac gga gac tgg tat caa aca gaa      720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag      768
Gly Tyr Ser Asp Tyr Ile Ser Ile Glu Gly Ile Met Ala Asp Gly Glu
            245                 250                 255 tat ttc ccg atc gcc att cat gat aaa acg ccg caa atc ggg ttt aca      816
Tyr Phe Pro Ile Ala Ile His Asp Lys Thr Pro Gln Ile Gly Phe Thr
        260                 265                 270 gag aca tcc cac att acg ccg tcc att ctg gat gaa gag gca aaa aag      864
Glu Thr Ser His Ile Thr Pro Ser Ile Leu Asp Glu Glu Ala Lys Lys
    275                 280                 285 aaa att gtc gaa gct gcc aaa aag gca aat gaa ggg ctt gga ctg caa      912
Lys Ile Val Glu Ala Ala Lys Lys Ala Asn Glu Gly Leu Gly Leu Gln
290                 295                 300 aat tgc gca aca cat aca gag atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gca gcc aga ttt gcc ggc tgg aat atg atc ccc     1008
Gly Leu Ile Glu Ser Ala Ala Arg Phe Ala Gly Trp Asn Met Ile Pro
            325                 330                 335 aat att aaa aag gtc ttt ggc ctt gat atg gcg caa tta tta tta gat     1056
Asn Ile Lys Lys Val Phe Gly Leu Asp Met Ala Gln Leu Leu Leu Asp
        340                 345                 350 gtc ctc tgt ttc gga aaa gac gcc gat ctg ccg gac gga tta ttg gat     1104
Val Leu Cys Phe Gly Lys Asp Ala Asp Leu Pro Asp Gly Leu Leu Asp
    355                 360                 365 caa gag cct tat tat gtt gcc gac tgc cat ttg tac ccg cag cat ttc     1152
Gln Glu Pro Tyr Tyr Val Ala Asp Cys His Leu Tyr Pro Gln His Phe
370                 375                 380 aaa caa aat ggc caa att cct gaa act gct gag gat ttg gtc att gaa     1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt     1248
Ala Ile Asp Ile Pro Asp Gly Leu Leu Lys Gly Asp Thr Glu Ile Val
            405                 410                 415 tct ttt tcg gcc gca gca cca ggc act tca gtt gat ttg aca ttg ttt     1296
Ser Phe Ser Ala Ala Pro Gly Thr Ser Val Asp Leu Thr Leu Phe
        420                 425                 430 gaa gct ttc aat tcc att gct gca ttt gaa ctg aaa ggc agt aat tca     1344
Glu Ala Phe Asn Ser Ile Ala Ala Phe Glu Leu Lys Gly Ser Asn Ser
    435                 440                 445 cag gat gtg gct gaa tca atc aga caa att cag cag cat gcg aag ctg     1392
Gln Asp Val Ala Glu Ser Ile Arg Gln Ile Gln Gln His Ala Lys Leu
450                 455                 460 acg gca aag tat gtg ctg cca gta                                     1416
Thr Ala Lys Tyr Val Leu Pro Val
465                 470
```

<210> SEQ ID NO 10
<211> LENGTH: 1416
<212> TYPE: DNA
<213> ORGANISM: Bacillus subtilis ATCC6633

<400> SEQUENCE: 10

```
atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtt agc      96
Pro His Met Phe Tyr Lys Ser Ala Ala Glu Lys Tyr Asn Leu Val Ser
                20                  25                  30 ttt att ccg aga cct ttt gca ata aca gcc tcc cat gca gca ctg att     144
Phe Ile Pro Arg Pro Phe Ala Ile Thr Ala Ser His Ala Ala Leu Ile
            35                  40                  45 gaa aaa tac tcg gtc gcg gtc ata aaa gat aaa gac tat ttt cag agc     192
Glu Lys Tyr Ser Val Ala Val Ile Lys Asp Lys Asp Tyr Phe Gln Ser
        50                  55                  60 tta gct gat ttt gag cat ccc gat tca att tat tgg gcg cat gag gat     240
Leu Ala Asp Phe Glu His Pro Asp Ser Ile Tyr Trp Ala His Glu Asp
65                  70                  75                  80 cat gac aag cct gaa gaa gag gtt gtc gag caa atc gtc aag gtt gcc     288
His Asp Lys Pro Glu Glu Glu Val Val Glu Gln Ile Val Lys Val Ala
                85                  90                  95 caa atg ttt gag gcg gac gcc atc aca aca aac aat gaa tta ttc att     336
Gln Met Phe Glu Ala Asp Ala Ile Thr Thr Asn Asn Glu Leu Phe Ile
                100                 105                 110 gcc ccg atg gcg aaa gcc tgt gaa cgc ctt ggc ctg agg ggc gcc gga     384
Ala Pro Met Ala Lys Ala Cys Glu Arg Leu Gly Leu Arg Gly Ala Gly
            115                 120                 125 gtg cag gca gcg gaa aat gcc aga gat aaa aat aaa atg agg gac gct     432
Val Gln Ala Ala Glu Asn Ala Arg Asp Lys Asn Lys Met Arg Asp Ala
        130                 135                 140 ttt aat aag gcg gga gtc aaa tcg atc aaa aac aaa cga gtc aca act     480
Phe Asn Lys Ala Gly Val Lys Ser Ile Lys Asn Lys Arg Val Thr Thr
145                 150                 155                 160 ctt gag gat ttt cgt gct gca ctt gaa gag atc ggc aca cct cta atc     528
Leu Glu Asp Phe Arg Ala Ala Leu Glu Glu Ile Gly Thr Pro Leu Ile
                165                 170                 175 tta aag cct aca tac tta gcg agt tca atc ggc gta acg ctg att acc     576
Leu Lys Pro Thr Tyr Leu Ala Ser Ser Ile Gly Val Thr Leu Ile Thr
            180                 185                 190 gac acg gag acg gca gaa gat gaa ttt aac aga gtc aat gac tac ctg     624
Asp Thr Glu Thr Ala Glu Asp Glu Phe Asn Arg Val Asn Asp Tyr Leu
        195                 200                 205 aaa tcg att aac gtg ccg aag gcg gtc aca ttt gaa gca ccg ttt att     672
Lys Ser Ile Asn Val Pro Lys Ala Val Thr Phe Glu Ala Pro Phe Ile
    210                 215                 220 gct gag gaa ttt tta cag ggt gag tac gga gac tgg tat caa aca gaa     720
Ala Glu Glu Phe Leu Gln Gly Glu Tyr Gly Asp Trp Tyr Gln Thr Glu
225                 230                 235                 240 ggg tac tcc gac tat atc agc ata gaa ggc att atg gca gat ggt gag     768
Gly Tyr Ser Asp Tyr Ile Ser Ile Glu Gly Ile Met Ala Asp Gly Glu
                245                 250                 255 tat ttt ccg atc gcc att cat gac aaa acg ccg caa att gga ttt aca     816
Tyr Phe Pro Ile Ala Ile His Asp Lys Thr Pro Gln Ile Gly Phe Thr
            260                 265                 270 gag aca tca cat att acg cca tcc att ctg gat gaa gag gcg aaa aag     864
Glu Thr Ser His Ile Thr Pro Ser Ile Leu Asp Glu Glu Ala Lys Lys
        275                 280                 285
```

```
aaa att gtc gaa gcg gct aaa aag gca aat gaa ggg ctt gga ctg caa      912
Lys Ile Val Glu Ala Ala Lys Lys Ala Asn Glu Gly Leu Gly Leu Gln
    290                 295                 300 aat tgc gca aca cat aca gaa atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gct gcc aga ttc gca ggc tgg aat atg att cct     1008
Gly Leu Ile Glu Ser Ala Ala Arg Phe Ala Gly Trp Asn Met Ile Pro
                325                 330                 335 aac att aaa aag gtt ttc ggc ctt gat atg gcg caa tta tta tta gat     1056
Asn Ile Lys Lys Val Phe Gly Leu Asp Met Ala Gln Leu Leu Leu Asp
            340                 345                 350 gtt ctc tgt ttc gga aaa gat gct gat ctg ccg gac ggg tta ttg gat     1104
Val Leu Cys Phe Gly Lys Asp Ala Asp Leu Pro Asp Gly Leu Leu Asp
        355                 360                 365 caa gag cct tac tat gtt gct gac tgc cat ctg tac cct cag cat ttc     1152
Gln Glu Pro Tyr Tyr Val Ala Asp Cys His Leu Tyr Pro Gln His Phe
    370                 375                 380 aaa caa aat ggc cag atc cct gaa act gcc gag gat ttg gta atc gaa     1200
Lys Gln Asn Gly Gln Ile Pro Glu Thr Ala Glu Asp Leu Val Ile Glu
385                 390                 395                 400 gcg atc gat att ccg gat ggg ctt ttg aag ggt gat aca gaa atc gtt     1248
Ala Ile Asp Ile Pro Asp Gly Leu Leu Lys Gly Asp Thr Glu Ile Val
                405                 410                 415 act ttt tcg gct gcg gca cca gga aca tca gtt gat ttg aca ctg ttt     1296
Thr Phe Ser Ala Ala Ala Pro Gly Thr Ser Val Asp Leu Thr Leu Phe
            420                 425                 430 gaa gcc ttc aac tcc att gct gca ttt gaa ctg aaa ggc agc aat tca     1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg     1392
Gln Asp Val Ala Glu Ser Ile Arg Gln Ile Gln Gln His Ala Lys Leu
    450                 455                 460 acg gca aag tat gtg ctg cca gta                                     1416
Thr Ala Lys Tyr Val Leu Pro Val
465                 470
```

<210> SEQ ID NO 11
<211> LENGTH: 1416
<212> TYPE: DNA
<213> ORGANISM: Bacillus subtilis IAM1213

<400> SEQUENCE: 11

```
atg gag aga aaa aca gta ttg gtc atc gct gat ctt gga ggc tgc ccg       48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc       96
Pro His Met Phe Tyr Lys Ser Ala Ala Glu Lys Tyr Asn Leu Val Ser
                20                  25                  30 ttt att cca aga cct ttt gca att aca gcc tcc cat gca gca ttg att      144
Phe Ile Pro Arg Pro Phe Ala Ile Thr Ala Ser His Ala Ala Leu Ile
            35                  40                  45 gaa aaa tac tcg gtc gcg gtc ata aaa gat aaa gac tat ttt aag agt      192
Glu Lys Tyr Ser Val Ala Val Ile Lys Asp Lys Asp Tyr Phe Lys Ser
        50                  55                  60 tta gct gat ttt gag cat cct gac tcc att tat tgg gcg cat gag gat      240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc      288
His Asn Lys Pro Glu Glu Glu Val Val Glu Gln Ile Val Lys Val Ala
                85                  90                  95
```

```
gaa atg ttt ggg gcg gat gcc atc aca aca aac aat gaa tta ttc att        336
Glu Met Phe Gly Ala Asp Ala Ile Thr Thr Asn Asn Glu Leu Phe Ile
        100                 105                 110 gct ccg atg gcg aaa gcc tgt gaa cgt ctg ggc ctg aga ggt gcc ggc        384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct        432
Val Gln Ala Ala Glu Asn Ala Arg Asp Lys Asn Lys Met Arg Asp Ala
        130                 135                 140 ttt aat aag gcc gga gtc aaa tcg atc aaa aac aaa cga gtc aca act        480
Phe Asn Lys Ala Gly Val Lys Ser Ile Lys Asn Lys Arg Val Thr Thr
145                 150                 155                 160 ctc gaa gat ttc cgt gct gct ctt gaa gag atc ggc aca cct ctt atc        528
Leu Glu Asp Phe Arg Ala Ala Leu Glu Glu Ile Gly Thr Pro Leu Ile
                165                 170                 175 tta aag cct aca tac tta gcg agt tca atc ggt gta acg ctg att acg        576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg        624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc        672
Lys Ser Ile Asn Val Pro Lys Ala Val Thr Phe Glu Ala Pro Phe Ile
    210                 215                 220 gct gaa gaa ttt tta cag ggt gag tac gga gac tgg tat caa aca gaa        720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag        768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca        816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag        864
Glu Thr Ser His Ile Thr Pro Ser Ile Leu Asp Glu Glu Ala Lys Lys
        275                 280                 285 aaa att gtc gaa gct gcc aaa aag gca aat gaa ggt ctt ggc ctg caa        912
Lys Ile Val Glu Ala Ala Lys Lys Ala Asn Glu Gly Leu Gly Leu Gln
    290                 295                 300 aat tgc gca aca cat aca gag atc aag cta atg aaa aat aga gaa ccg        960
Asn Cys Ala Thr His Thr Glu Ile Lys Leu Met Lys Asn Arg Glu Pro
305                 310                 315                 320 ggt tta att gaa tcg gca gcc aga ttc gcc ggc tgg aat atg atc ccc       1008
Gly Leu Ile Glu Ser Ala Ala Arg Phe Ala Gly Trp Asn Met Ile Pro
                325                 330                 335 aat att aaa aag gtc ttt ggc ctt gat atg gcg caa tta tta tta gat       1056
Asn Ile Lys Lys Val Phe Gly Leu Asp Met Ala Gln Leu Leu Leu Asp
            340                 345                 350 gtc ctt tgt ttc gga aaa gac gcc gat ctg ccg gac gga tta ttg gat       1104
Val Leu Cys Phe Gly Lys Asp Ala Asp Leu Pro Asp Gly Leu Leu Asp
        355                 360                 365 caa gag cct tat tat gtt gcc gac tgc cat ttg tac ccg caa cat ttc       1152
Gln Glu Pro Tyr Tyr Val Ala Asp Cys His Leu Tyr Pro Gln His Phe
    370                 375                 380 aaa caa aat ggc cag att cca gaa act gct gag gat ttg gtc att gaa       1200
Lys Gln Asn Gly Gln Ile Pro Glu Thr Ala Glu Asp Leu Val Ile Glu
385                 390                 395                 400 gcg atc gat ctg cct gac ggg ctt tta aaa ggg gat act gag atc gtt       1248
Ala Ile Asp Leu Pro Asp Gly Leu Leu Lys Gly Asp Thr Glu Ile Val
                405                 410                 415
```

```
tct ttt tcg gcc gca gca cca gga act tca gtt gat ttg aca ttg ttt    1296
Ser Phe Ser Ala Ala Ala Pro Gly Thr Ser Val Asp Leu Thr Leu Phe
        420                 425                 430 gaa gct ttc aat tcc att gct gca ttt gaa ctg aaa ggc agt aat tca    1344
Glu Ala Phe Asn Ser Ile Ala Ala Phe Glu Leu Lys Gly Ser Asn Ser
            435                 440                 445 cag gat gtg gct gaa tca atc aga caa att cag cag cat gcg aag ctg    1392
Gln Asp Val Ala Glu Ser Ile Arg Gln Ile Gln Gln His Ala Lys Leu
450                 455                 460 acg gca aag tat gtg ctg cca gta                                    1416
Thr Ala Lys Tyr Val Leu Pro Val
465                 470

<210> SEQ ID NO 12
<211> LENGTH: 1416
<212> TYPE: DNA
<213> ORGANISM: Bacillus subtilis IAM1107

<400> SEQUENCE: 12 atg gag aga aaa aca gta ttg gtc atc gct gat ctt gga ggc tgc ccg    48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc    96
Pro His Met Phe Tyr Lys Ser Ala Ala Glu Lys Tyr Asn Leu Val Ser
                20                  25                  30 ttt att cca aga cct ttt gca att aca gcc tcc cat gca gca ttg att    144
Phe Ile Pro Arg Pro Phe Ala Ile Thr Ala Ser His Ala Ala Leu Ile
            35                  40                  45 gaa aaa tac tcg gtc gcg gtc gta aaa gat aaa gac tat ttt aag agt    192
Glu Lys Tyr Ser Val Ala Val Val Lys Asp Lys Asp Tyr Phe Lys Ser
        50                  55                  60 tta gct gat ttt gag cat cct gac tcc att tat tgg gcg cat gag gat    240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc    288
His Asn Lys Pro Glu Glu Glu Val Val Glu Gln Ile Val Lys Val Ala
                85                  90                  95 gaa atg ttc ggg gcg gat gcc atc aca aca aac aat gaa tta ttc att    336
Glu Met Phe Gly Ala Asp Ala Ile Thr Thr Asn Asn Glu Leu Phe Ile
                100                 105                 110 gct ccg atg gcg aaa gcc tgt gaa cgt ctg ggc ttg aga ggt gcc ggc    384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct    432
Val Gln Ala Ala Glu Asn Ala Arg Asp Lys Asn Lys Met Arg Asp Ala
        130                 135                 140 ttt aat aag gcc gga gtc aaa tcg atc aaa aac aaa cga gtc aca act    480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc    528
Leu Glu Asp Phe Arg Ala Ala Leu Glu Glu Ile Gly Thr Pro Leu Ile
                165                 170                 175 tta aag cct aca tac tta gcg agt tct atc ggt gta acg ctg att acg    576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg    624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc    672
Lys Ser Ile Asn Val Pro Lys Ala Val Thr Phe Glu Ala Pro Phe Ile
210                 215                 220
```

```
gct gaa gaa ttt tta cag ggt gag tac gga gac tgg tat caa aca gaa      720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag      768
Gly Tyr Ser Asp Tyr Ile Ser Ile Glu Gly Ile Met Ala Asp Gly Glu
            245                 250                 255 tat ttc ccg atc gcc att cat gat aaa acg ccg caa atc ggg ttt aca      816
Tyr Phe Pro Ile Ala Ile His Asp Lys Thr Pro Gln Ile Gly Phe Thr
    260                 265                 270 gag aca tcc cac att acg ccg tcc att ctg gat gaa gag gca aaa aag      864
Glu Thr Ser His Ile Thr Pro Ser Ile Leu Asp Glu Glu Ala Lys Lys
275                 280                 285 aaa att gtc gaa gct gcc aaa aag gca aat gaa ggg ctt ggc ctg caa      912
Lys Ile Val Glu Ala Ala Lys Lys Ala Asn Glu Gly Leu Gly Leu Gln
290                 295                 300 aat tgc gca aca cat aca gag gtc aag cta atg aaa aac aga gaa ccg      960
Asn Cys Ala Thr His Thr Glu Val Lys Leu Met Lys Asn Arg Glu Pro
305                 310                 315                 320 ggt tta att gaa tcg gca gcc aga ttt gcc ggc tgg aat atg atc cct     1008
Gly Leu Ile Glu Ser Ala Ala Arg Phe Ala Gly Trp Asn Met Ile Pro
            325                 330                 335 aac att aaa aag gtt ttc ggc ctt gat atg gcg caa tta tta tta gat     1056
Asn Ile Lys Lys Val Phe Gly Leu Asp Met Ala Gln Leu Leu Leu Asp
    340                 345                 350 gtc ctc tgt ttc gga aaa gat gcc gat ctg ccg gac gga tta ttg gat     1104
Val Leu Cys Phe Gly Lys Asp Ala Asp Leu Pro Asp Gly Leu Leu Asp
355                 360                 365 caa gag cct tac tat gtc gcc gac tgc cat ttg tac ccg cag cat ttc     1152
Gln Glu Pro Tyr Tyr Val Ala Asp Cys His Leu Tyr Pro Gln His Phe
370                 375                 380 aaa caa aat ggc cag att cca gaa acc gct gag gat ttg gtc att gaa     1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc ttt     1248
Ala Ile Asp Ile Pro Asp Gly Leu Leu Lys Gly Asp Thr Glu Ile Phe
            405                 410                 415 tct ttt tcg gcc gca gca cca ggc act tca gtt gat ttg aca ttg ttt     1296
Ser Phe Ser Ala Ala Ala Pro Gly Thr Ser Val Asp Leu Thr Leu Phe
    420                 425                 430 gaa gct ttc aat tcc att gct gca ttt gaa ctg aaa ggc agt aat tca     1344
Glu Ala Phe Asn Ser Ile Ala Ala Phe Glu Leu Lys Gly Ser Asn Ser
435                 440                 445 cag gat gtg gct gaa tca atc aga caa att cag cag cat gcg aag ctg     1392
Gln Asp Val Ala Glu Ser Ile Arg Gln Ile Gln Gln His Ala Lys Leu
450                 455                 460 acg gca aag tat gtg ctg cca gta                                    1416
Thr Ala Lys Tyr Val Leu Pro Val
465                 470

<210> SEQ ID NO 13
<211> LENGTH: 1416
<212> TYPE: DNA
<213> ORGANISM: Bacillus subtilis IAM1214

<400> SEQUENCE: 13 atg gag aga aaa aca gta ttg gtc atc gct gat ctt gga ggc tgc ccg       48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtt agc       96
Pro His Met Phe Tyr Lys Ser Ala Ala Glu Lys Tyr Asn Leu Val Ser
            20                  25                  30
```

| | |
|---|---|
| ttt att ccg aga cct ttt gca ata aca gcc tcc cat gca gca ctg att<br>Phe Ile Pro Arg Pro Phe Ala Ile Thr Ala Ser His Ala Ala Leu Ile<br>35                  40                  45 | 144 |
| gaa aaa tac tcg gtc gcg gtc ata aaa gat aaa gac tat ttt cag agc<br>Glu Lys Tyr Ser Val Ala Val Ile Lys Asp Lys Asp Tyr Phe Gln Ser<br>50                  55                  60 | 192 |
| tta gct gat ttt gag cat ccc gat tca att tat tgg gcg cat gag gat<br>Leu Ala Asp Phe Glu His Pro Asp Ser Ile Tyr Trp Ala His Glu Asp<br>65                  70                  75                  80 | 240 |
| cat gac aag cct gaa gaa gag gtt gtc gag caa atc gtc aag gtt gcc<br>His Asp Lys Pro Glu Glu Glu Val Val Glu Gln Ile Val Lys Val Ala<br>                85                  90                  95 | 288 |
| caa atg ttt gag gcg gac gcc atc aca aca aac aat gaa tta ttc att<br>Gln Met Phe Glu Ala Asp Ala Ile Thr Thr Asn Asn Glu Leu Phe Ile<br>            100                 105                 110 | 336 |
| gcc ccg atg gcg aaa gcc tgt gaa cgc ctt ggc ctg agg ggc gcc gga<br>Ala Pro Met Ala Lys Ala Cys Glu Arg Leu Gly Leu Arg Gly Ala Gly<br>        115                 120                 125 | 384 |
| gtg cag gca gcg gaa aat gcc aga gat aaa aat aaa atg agg gac gct<br>Val Gln Ala Ala Glu Asn Ala Arg Asp Lys Asn Lys Met Arg Asp Ala<br>130                 135                 140 | 432 |
| ttt aat aag gcg gga gtc aaa tcg atc aaa aac aaa cga gtc aca act<br>Phe Asn Lys Ala Gly Val Lys Ser Ile Lys Asn Lys Arg Val Thr Thr<br>145                 150                 155                 160 | 480 |
| ctt gag gat ttt cgt gct gca ctt gaa gag atc ggc aca cct cta atc<br>Leu Glu Asp Phe Arg Ala Ala Leu Glu Glu Ile Gly Thr Pro Leu Ile<br>                165                 170                 175 | 528 |
| tta aag cct aca tac tta gcg agt tca atc ggc gta acg ctg att acc<br>Leu Lys Pro Thr Tyr Leu Ala Ser Ser Ile Gly Val Thr Leu Ile Thr<br>            180                 185                 190 | 576 |
| gac acg gag acg gca gaa gat gaa ttt aac aga gtc aat gac tac ctg<br>Asp Thr Glu Thr Ala Glu Asp Glu Phe Asn Arg Val Asn Asp Tyr Leu<br>        195                 200                 205 | 624 |
| aaa tcg att aac gtg ccg aag gcg gtc aca ttt gaa gca ccg ttt att<br>Lys Ser Ile Asn Val Pro Lys Ala Val Thr Phe Glu Ala Pro Phe Ile<br>210                 215                 220 | 672 |
| gct gag gaa ttt tta cag ggt gag tac gga gac tgg tat caa aca gaa<br>Ala Glu Glu Phe Leu Gln Gly Glu Tyr Gly Asp Trp Tyr Gln Thr Glu<br>225                 230                 235                 240 | 720 |
| ggg tac tcc gac tat atc agc ata gaa ggc att atg gca gat ggt gag<br>Gly Tyr Ser Asp Tyr Ile Ser Ile Glu Gly Ile Met Ala Asp Gly Glu<br>                245                 250                 255 | 768 |
| tat ttt ccg atc gcc att cat gac aaa acg ccg caa att gga ttt aca<br>Tyr Phe Pro Ile Ala Ile His Asp Lys Thr Pro Gln Ile Gly Phe Thr<br>            260                 265                 270 | 816 |
| gag aca tca cat att acg cca tcc att ctg gat gaa gag gcg aaa aag<br>Glu Thr Ser His Ile Thr Pro Ser Ile Leu Asp Glu Glu Ala Lys Lys<br>        275                 280                 285 | 864 |
| aaa att gtc gaa gcg gct aaa aag gca aat gaa ggg ctt gga ctg caa<br>Lys Ile Val Glu Ala Ala Lys Lys Ala Asn Glu Gly Leu Gly Leu Gln<br>290                 295                 300 | 912 |
| aat tgc gca aca cat aca gaa atc aag cta atg aaa aac aga gaa ccg<br>Asn Cys Ala Thr His Thr Glu Ile Lys Leu Met Lys Asn Arg Glu Pro<br>305                 310                 315                 320 | 960 |
| ggt tta ata gag tcg gct gcc aga ttc gca ggc tgg aat atg att cct<br>Gly Leu Ile Glu Ser Ala Ala Arg Phe Ala Gly Trp Asn Met Ile Pro<br>                325                 330                 335 | 1008 |
| aac att aaa aag gtt ttc ggc ctt gat atg gcg caa tta tta tta gat<br>Asn Ile Lys Lys Val Phe Gly Leu Asp Met Ala Gln Leu Leu Leu Asp<br>            340                 345                 350 | 1056 |

```
gtt ctc tgt ttc gga aaa gat gct gat ctg ccg gac ggg tta ttg gat          1104
Val Leu Cys Phe Gly Lys Asp Ala Asp Leu Pro Asp Gly Leu Leu Asp
        355                 360                 365 caa gag cct tac tat gtt gct gac tgc cat ctg tac cct cag cat ttc          1152
Gln Glu Pro Tyr Tyr Val Ala Asp Cys His Leu Tyr Pro Gln His Phe
370                 375                 380 aaa caa aat ggc cag atc cct gaa act gcc gag gat ttg gta atc gaa          1200
Lys Gln Asn Gly Gln Ile Pro Glu Thr Ala Glu Asp Leu Val Ile Glu
385                 390                 395                 400 gcg atc gat att ccg gat ggg ctt ttg aag ggt gat aca gaa atc gtt          1248
Ala Ile Asp Ile Pro Asp Gly Leu Leu Lys Gly Asp Thr Glu Ile Val
                405                 410                 415 act ttt tcg gct gcg gca cca gga aca tca gtt gat ttg aca ctg ttt          1296
Thr Phe Ser Ala Ala Ala Pro Gly Thr Ser Val Asp Leu Thr Leu Phe
            420                 425                 430 gaa gcc ttc aac tcc att gct gca ttt gaa ctg aaa ggc agc aat tca          1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg          1392
Gln Asp Val Ala Glu Ser Ile Arg Gln Ile Gln Gln His Ala Lys Leu
450                 455                 460 acg gca aag tat gtg ctg cca gta                                          1416
Thr Ala Lys Tyr Val Leu Pro Val
465                 470

<210> SEQ ID NO 14
<211> LENGTH: 1416
<212> TYPE: DNA
<213> ORGANISM: Bacillus subtilis ATCC21555

<400> SEQUENCE: 14 atg gag aga aaa aca gta ttg gtt atc gct gat ctt ggg ggc tgc ccg          48
Met Glu Arg Lys Thr Val Leu Val Ile Ala Asp Leu Gly Gly Cys Pro
1               5                   10                  15 ccg cat atg ttt tac aaa agc gca gcc gaa aaa tac aac ctc gtc agc          96
Pro His Met Phe Tyr Lys Ser Ala Ala Glu Lys Tyr Asn Leu Val Ser
                20                  25                  30 ttt att ccg aga ccc ttt gca att aca gcc tct cat gcg gcc tta att          144
Phe Ile Pro Arg Pro Phe Ala Ile Thr Ala Ser His Ala Ala Leu Ile
            35                  40                  45 gaa aaa tac tcg att gcg gtc att aaa gat aaa gac tat ttt aag agt          192
Glu Lys Tyr Ser Ile Ala Val Ile Lys Asp Lys Asp Tyr Phe Lys Ser
        50                  55                  60 ctg gct gat ttt gaa cat ccc gat tcg att tat tgg gct cat gaa gat          240
Leu Ala Asp Phe Glu His Pro Asp Ser Ile Tyr Trp Ala His Glu Asp
65                  70                  75                  80 cat gac aaa cct gag gaa gaa gtc gtc gaa gaa atc gtg aaa gtg gcc          288
His Asp Lys Pro Glu Glu Glu Val Val Glu Glu Ile Val Lys Val Ala
                85                  90                  95 gac atg ttt ggg gtt gac gcc att acg acc aac aat gaa ctg ttt atc          336
Asp Met Phe Gly Val Asp Ala Ile Thr Thr Asn Asn Glu Leu Phe Ile
                100                 105                 110 gct ccg atg gca aaa gcg tgt aaa cgt ctc ggc ctg cgg gga gcg ggc          384
Ala Pro Met Ala Lys Ala Cys Lys Arg Leu Gly Leu Arg Gly Ala Gly
            115                 120                 125 gta cag gcc gct gaa aac gcc aga gat aaa aat aaa atg aga gcc gcc          432
Val Gln Ala Ala Glu Asn Ala Arg Asp Lys Asn Lys Met Arg Ala Ala
        130                 135                 140 ttc aac cgg gcc ggc gtc aaa tcc atc aaa aac aaa cgg gtg acg acc          480
Phe Asn Arg Ala Gly Val Lys Ser Ile Lys Asn Lys Arg Val Thr Thr
145                 150                 155                 160
```

```
ctg gaa gat ttc cgc gcc gcg ctt cag gaa atc gga acg ccg ctt att        528
Leu Glu Asp Phe Arg Ala Ala Leu Gln Glu Ile Gly Thr Pro Leu Ile
                165                 170                 175 ctg aag cct aca tat ctg gca agc tcg atc ggc gtg acg ctt att aaa        576
Leu Lys Pro Thr Tyr Leu Ala Ser Ser Ile Gly Val Thr Leu Ile Lys
            180                 185                 190 gag atg gaa acg gcc gaa gct gaa ttc aac aga gtc aat gag tac ttg        624
Glu Met Glu Thr Ala Glu Ala Glu Phe Asn Arg Val Asn Glu Tyr Leu
        195                 200                 205 aaa tcg att aat gta ccg aaa gcg gtg acg ttt gaa gcg ccg ttt atc        672
Lys Ser Ile Asn Val Pro Lys Ala Val Thr Phe Glu Ala Pro Phe Ile
    210                 215                 220 gcg gaa gaa ttc ttg cag ggc gag tat gat gac tgg tac gaa aca agc        720
Ala Glu Glu Phe Leu Gln Gly Glu Tyr Asp Asp Trp Tyr Glu Thr Ser
225                 230                 235                 240 ggt tat tcc gac tat atc agc atc gaa ggc atc atg gcc gac gga gaa        768
Gly Tyr Ser Asp Tyr Ile Ser Ile Glu Gly Ile Met Ala Asp Gly Glu
                245                 250                 255 tac ttc ccc gtt gcg atc cat gat aaa aca ccg caa atc gga ttc acg        816
Tyr Phe Pro Val Ala Ile His Asp Lys Thr Pro Gln Ile Gly Phe Thr
            260                 265                 270 gag aca gcg cat att acg ccg tcc atc ctg gat gat gac gcc aag cgg        864
Glu Thr Ala His Ile Thr Pro Ser Ile Leu Asp Asp Asp Ala Lys Arg
        275                 280                 285 aaa atc gtc gaa gct gcc aag aag gcg aat gaa gga ctc ggc ctc gaa        912
Lys Ile Val Glu Ala Ala Lys Lys Ala Asn Glu Gly Leu Gly Leu Glu
    290                 295                 300 aac tgt gca acg cat aca gaa ata aaa tta atg aaa aac cgg gaa gcc        960
Asn Cys Ala Thr His Thr Glu Ile Lys Leu Met Lys Asn Arg Glu Ala
305                 310                 315                 320 gga ctg att gag tca gcg gcc aga ttc gcg gga tgg aat atg att ccg       1008
Gly Leu Ile Glu Ser Ala Ala Arg Phe Ala Gly Trp Asn Met Ile Pro
                325                 330                 335 aat att aaa aag gtc ttc ggc gtt gat atg gcg cag cta tta ttg gat       1056
Asn Ile Lys Lys Val Phe Gly Val Asp Met Ala Gln Leu Leu Leu Asp
            340                 345                 350 gtt ctc tgt tac gga aaa gaa gct gat ctg ccg aaa gga tta ttg gag       1104
Val Leu Cys Tyr Gly Lys Glu Ala Asp Leu Pro Lys Gly Leu Leu Glu
        355                 360                 365 cag gag cca tgc tat gtc gca gac tgc cac ttg tat cct cag cat ttc       1152
Gln Glu Pro Cys Tyr Val Ala Asp Cys His Leu Tyr Pro Gln His Phe
    370                 375                 380 aaa gag aac ggc cag ctg cct gag acg gtt gtc gat ttc gtc att gaa       1200
Lys Glu Asn Gly Gln Leu Pro Glu Thr Val Val Asp Phe Val Ile Glu
385                 390                 395                 400 agc att gaa att cct gac ggc gtc tta aag gga gac act gaa ctc gtt       1248
Ser Ile Glu Ile Pro Asp Gly Val Leu Lys Gly Asp Thr Glu Leu Val
                405                 410                 415 tct ttc tca gcg gct gag gcg ggt acg tca gtg gat ctg cgg ctg ttc       1296
Ser Phe Ser Ala Ala Glu Ala Gly Thr Ser Val Asp Leu Arg Leu Phe
            420                 425                 430 gaa gcg ttc aac agc att gcg gcg ttt gag ctg aaa gga agc aat tcg       1344
Glu Ala Phe Asn Ser Ile Ala Ala Phe Glu Leu Lys Gly Ser Asn Ser
        435                 440                 445 aac gac gtg gcc gaa tca atc aaa caa att cag cag cag gcg aag ctg       1392
Asn Asp Val Ala Glu Ser Ile Lys Gln Ile Gln Gln Gln Ala Lys Leu
    450                 455                 460 act gca aag tat gcg tta tcg gta                                       1416
Thr Ala Lys Tyr Ala Leu Ser Val
```

<210> SEQ ID NO 15
<211> LENGTH: 1416
<212> TYPE: DNA
<213> ORGANISM: Bacillus amyloliquefaciens IFO3022

<400> SEQUENCE: 15

| | | | | | | | | | | | | | | | | |
|---|---|---|---|---|---|---|---|---|---|---|---|---|---|---|---|---|
| atg | gag | aga | aaa | aca | gta | ttg | gtt | atc | gct | gac | ctt | ggg | gga | tgc | ccg | 48 |
| Met | Glu | Arg | Lys | Thr | Val | Leu | Val | Ile | Ala | Asp | Leu | Gly | Gly | Cys | Pro | |
| 1 | | | | 5 | | | | | 10 | | | | | 15 | | |
| ccg | cat | atg | ttt | tac | aaa | agc | gca | gcc | gaa | aaa | tac | aac | ctc | gtc | agc | 96 |
| Pro | His | Met | Phe | Tyr | Lys | Ser | Ala | Ala | Glu | Lys | Tyr | Asn | Leu | Val | Ser | |
| | | | 20 | | | | | 25 | | | | | 30 | | | |
| ttt | att | ccg | aga | cct | ttt | gca | att | aca | gcc | tct | cat | gcg | gca | tta | att | 144 |
| Phe | Ile | Pro | Arg | Pro | Phe | Ala | Ile | Thr | Ala | Ser | His | Ala | Ala | Leu | Ile | |
| | | 35 | | | | | 40 | | | | | 45 | | | | |
| gaa | aaa | tac | tcg | gtc | gcg | gtc | ata | aaa | gat | aaa | gac | tat | ttt | aag | agt | 192 |
| Glu | Lys | Tyr | Ser | Val | Ala | Val | Ile | Lys | Asp | Lys | Asp | Tyr | Phe | Lys | Ser | |
| | 50 | | | | | 55 | | | | | 60 | | | | | |
| ctg | gct | gat | ttt | gag | cat | ccc | gat | tcg | att | tac | tgg | gct | cat | gaa | gat | 240 |
| Leu | Ala | Asp | Phe | Glu | His | Pro | Asp | Ser | Ile | Tyr | Trp | Ala | His | Glu | Asp | |
| 65 | | | | | 70 | | | | | 75 | | | | | 80 | |
| cat | gac | aaa | cct | gag | gaa | gaa | gta | gtc | gaa | gaa | atc | gtc | aag | gtg | gcc | 288 |
| His | Asp | Lys | Pro | Glu | Glu | Glu | Val | Val | Glu | Glu | Ile | Val | Lys | Val | Ala | |
| | | | | 85 | | | | | 90 | | | | | 95 | | |
| ggc | atg | ttc | gcg | gtt | gac | gcc | att | acg | acc | aac | aat | gaa | ctg | ttt | atc | 336 |
| Gly | Met | Phe | Ala | Val | Asp | Ala | Ile | Thr | Thr | Asn | Asn | Glu | Leu | Phe | Ile | |
| | | | 100 | | | | | 105 | | | | | 110 | | | |
| gct | ccg | atg | gca | aaa | gcg | tgt | gaa | cgt | ctc | ggc | ctg | cgg | gga | gcg | ggc | 384 |
| Ala | Pro | Met | Ala | Lys | Ala | Cys | Glu | Arg | Leu | Gly | Leu | Arg | Gly | Ala | Gly | |
| | | 115 | | | | | 120 | | | | | 125 | | | | |
| gta | cag | gcc | gct | gaa | aat | gcc | aga | gat | aaa | aac | aaa | atg | aga | gcc | gct | 432 |
| Val | Gln | Ala | Ala | Glu | Asn | Ala | Arg | Asp | Lys | Asn | Lys | Met | Arg | Ala | Ala | |
| | 130 | | | | | 135 | | | | | 140 | | | | | |
| ttc | aac | cgg | gcc | ggc | gtc | aag | tct | atc | aaa | aac | aga | cgg | gtg | acg | acg | 480 |
| Phe | Asn | Arg | Ala | Gly | Val | Lys | Ser | Ile | Lys | Asn | Arg | Arg | Val | Thr | Thr | |
| 145 | | | | | 150 | | | | | 155 | | | | | 160 | |
| ctg | gaa | gat | ttc | cgc | gcc | gcg | ctt | cag | gaa | atc | gga | acg | ccg | ctc | att | 528 |
| Leu | Glu | Asp | Phe | Arg | Ala | Ala | Leu | Gln | Glu | Ile | Gly | Thr | Pro | Leu | Ile | |
| | | | | 165 | | | | | 170 | | | | | 175 | | |
| ctg | aag | cct | aca | tat | ctg | gcg | agc | tcc | atc | ggc | gtg | acg | ctc | atc | aaa | 576 |
| Leu | Lys | Pro | Thr | Tyr | Leu | Ala | Ser | Ser | Ile | Gly | Val | Thr | Leu | Ile | Lys | |
| | | | 180 | | | | | 185 | | | | | 190 | | | |
| gag | agg | gaa | acg | gcc | gaa | gcc | gaa | ttt | aac | aga | gtc | aat | gaa | tac | ctg | 624 |
| Glu | Arg | Glu | Thr | Ala | Glu | Ala | Glu | Phe | Asn | Arg | Val | Asn | Glu | Tyr | Leu | |
| | | 195 | | | | | 200 | | | | | 205 | | | | |
| aag | tcg | atc | aac | gta | ccg | aaa | gcg | gtc | acg | ttt | gaa | gcg | ccg | ttt | atc | 672 |
| Lys | Ser | Ile | Asn | Val | Pro | Lys | Ala | Val | Thr | Phe | Glu | Ala | Pro | Phe | Ile | |
| | 210 | | | | | 215 | | | | | 220 | | | | | |
| gcg | gaa | gaa | ttt | ttg | cag | ggc | gag | tat | gac | gac | tgg | tac | gaa | aca | agc | 720 |
| Ala | Glu | Glu | Phe | Leu | Gln | Gly | Glu | Tyr | Asp | Asp | Trp | Tyr | Glu | Thr | Ser | |
| 225 | | | | | 230 | | | | | 235 | | | | | 240 | |
| ggt | tat | tcc | gac | tat | atc | agc | ata | gaa | ggc | atc | atg | gcc | gac | gga | gaa | 768 |
| Gly | Tyr | Ser | Asp | Tyr | Ile | Ser | Ile | Glu | Gly | Ile | Met | Ala | Asp | Gly | Glu | |
| | | | | 245 | | | | | 250 | | | | | 255 | | |
| tac | ttc | cct | gtc | gca | att | cat | gat | aaa | aca | ccg | caa | atc | gga | ttc | acg | 816 |
| Tyr | Phe | Pro | Val | Ala | Ile | His | Asp | Lys | Thr | Pro | Gln | Ile | Gly | Phe | Thr | |
| | | | 260 | | | | | 265 | | | | | 270 | | | |
| gag | aca | tcg | cat | att | acg | ccg | tcc | atc | ctg | gat | gat | gac | gcg | aag | cgg | 864 |
| Glu | Thr | Ser | His | Ile | Thr | Pro | Ser | Ile | Leu | Asp | Asp | Asp | Ala | Lys | Arg | |
| | | 275 | | | | | 280 | | | | | 285 | | | | |

```
aaa atc gtc gaa gca gcc aag aag gcg aat gaa gga ctc ggc ctc gaa    912
Lys Ile Val Glu Ala Ala Lys Lys Ala Asn Glu Gly Leu Gly Leu Glu
    290                 295                 300 aac tgc gca acc cat aca gag att aaa tta atg aaa aac cgg gaa gcc    960
Asn Cys Ala Thr His Thr Glu Ile Lys Leu Met Lys Asn Arg Glu Ala
305                 310                 315                 320 gga ctg att gaa tca gcg gca cga ttt gcg ggc tgg aac atg att ccg   1008
Gly Leu Ile Glu Ser Ala Ala Arg Phe Ala Gly Trp Asn Met Ile Pro
                325                 330                 335 aat att aaa aag gtc ttc ggc gtc gat atg gcg cag ctg tta ttg gat   1056
Asn Ile Lys Lys Val Phe Gly Val Asp Met Ala Gln Leu Leu Leu Asp
            340                 345                 350 gtt ctc tgt ttc gga aaa gaa gcc gat ctg ccg aaa gga tta ttg gag   1104
Val Leu Cys Phe Gly Lys Glu Ala Asp Leu Pro Lys Gly Leu Leu Glu
        355                 360                 365 cag gag ccg tgc tat gtc gcc gac tgc cac ttg tat cct cag cat ttc   1152
Gln Glu Pro Cys Tyr Val Ala Asp Cys His Leu Tyr Pro Gln His Phe
    370                 375                 380 aaa gag aac ggc cag ctg cct gag acg gct gtc gat ttc gtc att gaa   1200
Lys Glu Asn Gly Gln Leu Pro Glu Thr Ala Val Asp Phe Val Ile Glu
385                 390                 395                 400 agc att gac att ccc gac ggc gtc tta aag gga gac acc gaa atc gtt   1248
Ser Ile Asp Ile Pro Asp Gly Val Leu Lys Gly Asp Thr Glu Ile Val
                405                 410                 415 tct ttc tcg gcg gcc gag gcg ggt aca tcc gtg gat ctg cgg ctg ttc   1296
Ser Phe Ser Ala Ala Glu Ala Gly Thr Ser Val Asp Leu Arg Leu Phe
            420                 425                 430 gaa gcg ttc aac agc att gcg gcg ttc gag ctg aaa gga agc aat tcg   1344
Glu Ala Phe Asn Ser Ile Ala Ala Phe Glu Leu Lys Gly Ser Asn Ser
        435                 440                 445 ggt gac gtg gcc gaa tca atc aaa caa att cag cag cag gcg aag ctg   1392
Gly Asp Val Ala Glu Ser Ile Lys Gln Ile Gln Gln Gln Ala Lys Leu
    450                 455                 460 act gca aag tat gcg tta ccg gta                                   1416
Thr Ala Lys Tyr Ala Leu Pro Val <210> SEQ ID NO 16
<211> LENGTH: 1428
<212> TYPE: DNA
<213> ORGANISM: Bacillus pumilus NRRL B-12025

<400> SEQUENCE: 16 gtg ctt tca ttg agt aaa aaa act gta ctt gtc att gct gac tta gga     48
Val Leu Ser Leu Ser Lys Lys Thr Val Leu Val Ile Ala Asp Leu Gly
  1               5                  10                  15 ggg tgc ccg ccc cat atg ttt tat gaa agc gtg gcg gca tca tac cat     96
Gly Cys Pro Pro His Met Phe Tyr Glu Ser Val Ala Ala Ser Tyr His
                 20                  25                  30 atc gtt tct tat atc cca aga ccc ttt gcg att aca aag gga cat gcc    144
Ile Val Ser Tyr Ile Pro Arg Pro Phe Ala Ile Thr Lys Gly His Ala
             35                  40                  45 gag cta atc gaa aaa tac tcc att gcc gtc atc aaa gac cgt gat tat    192
Glu Leu Ile Glu Lys Tyr Ser Ile Ala Val Ile Lys Asp Arg Asp Tyr
         50                  55                  60 ttt gag aca cac cct tct ttt gaa cac cct gat tct att tac tgg gca    240
Phe Glu Thr His Pro Ser Phe Glu His Pro Asp Ser Ile Tyr Trp Ala
 65                  70                  75                  80 cat gat gat tat cca aaa tca gaa gaa gaa gtt gtg gaa gac ttc att    288
His Asp Asp Tyr Pro Lys Ser Glu Glu Glu Val Val Glu Asp Phe Ile
                 85                  90                  95 cga gta gct tcc ttt ttc aaa gca gat gca atc acg acc aat aat gaa    336
```

```
                    Arg Val Ala Ser Phe Phe Lys Ala Asp Ala Ile Thr Thr Asn Asn Glu
                                100                 105                 110 tta ttc att gca ccg atg gca aag gcc gct gaa cgt ctt ggg cta cga          384
Leu Phe Ile Ala Pro Met Ala Lys Ala Ala Glu Arg Leu Gly Leu Arg
            115                 120                 125 ggt gcc ggt gtc aag gca gcc gaa atg gcg cgt gat aaa agc caa atg          432
Gly Ala Gly Val Lys Ala Ala Glu Met Ala Arg Asp Lys Ser Gln Met
130                 135                 140 agg gct gca ttc aat gcc tct ggc gtc aaa gcg gtg aaa act cag cct          480
Arg Ala Ala Phe Asn Ala Ser Gly Val Lys Ala Val Lys Thr Gln Pro
145                 150                 155                 160 gtc acg act tta tct gat ttc caa caa gcc att gag tct atc gga aca          528
Val Thr Thr Leu Ser Asp Phe Gln Gln Ala Ile Glu Ser Ile Gly Thr
                165                 170                 175 ccg ctc att tta aag cct aca tat tta gcc agt tct att ggc gtc acc          576
Pro Leu Ile Leu Lys Pro Thr Tyr Leu Ala Ser Ser Ile Gly Val Thr
            180                 185                 190 ttg ttt cat gac aaa gcc gga agt gat gac ttg ttt tta caa gta caa          624
Leu Phe His Asp Lys Ala Gly Ser Asp Asp Leu Phe Leu Gln Val Gln
        195                 200                 205 tcg tat ttg gaa acc ata cca gtc cca gac gct gtc acg tat gaa gca          672
Ser Tyr Leu Glu Thr Ile Pro Val Pro Asp Ala Val Thr Tyr Glu Ala
    210                 215                 220 ccg ttt gtc gct gaa aca tat tta gag ggt gct tac gaa gat tgg tat          720
Pro Phe Val Ala Glu Thr Tyr Leu Glu Gly Ala Tyr Glu Asp Trp Tyr
225                 230                 235                 240 gaa gac gaa gga tat gct gat tat gtc agt gta gaa ggg ctg gtc gta          768
Glu Asp Glu Gly Tyr Ala Asp Tyr Val Ser Val Glu Gly Leu Val Val
                245                 250                 255 gag ggc gaa tat ctc cct ttt gtc ata cat gat aaa acc cct caa atc          816
Glu Gly Glu Tyr Leu Pro Phe Val Ile His Asp Lys Thr Pro Gln Ile
            260                 265                 270 ggc ttt aca gaa acg gct cat atc act ccg acg atc tta gac aat gaa          864
Gly Phe Thr Glu Thr Ala His Ile Thr Pro Thr Ile Leu Asp Asn Glu
        275                 280                 285 gcc aag caa atc atc att gaa gca gca agg aag gca aat gaa ggg cta          912
Ala Lys Gln Ile Ile Ile Glu Ala Ala Arg Lys Ala Asn Glu Gly Leu
    290                 295                 300 ggt ctt gaa cat tgt gca acc cat aca gaa atc aaa ctc atg aaa aat          960
Gly Leu Glu His Cys Ala Thr His Thr Glu Ile Lys Leu Met Lys Asn
305                 310                 315                 320 cga gaa act gga ctg atc gag gca gcg gct cga ttc gct ggc tgg aat         1008
Arg Glu Thr Gly Leu Ile Glu Ala Ala Ala Arg Phe Ala Gly Trp Asn
                325                 330                 335 atg atc ccg aat att aaa aaa gtc ttt ggc gtc gat atg gcg aag cta         1056
Met Ile Pro Asn Ile Lys Lys Val Phe Gly Val Asp Met Ala Lys Leu
            340                 345                 350 ttg att gat gta tta gtt gat ggt aaa aag gct gta ctg cca aaa cag         1104
Leu Ile Asp Val Leu Val Asp Gly Lys Lys Ala Val Leu Pro Lys Gln
        355                 360                 365 ctg ctt tct gga cat aca ttt tat gta gcg gac tgc cac ctg tac cct         1152
Leu Leu Ser Gly His Thr Phe Tyr Val Ala Asp Cys His Leu Tyr Pro
    370                 375                 380 cag cat ttt aaa gag agt ggg ctt atc ccg cct gaa gcc aca cat att         1200
Gln His Phe Lys Glu Ser Gly Leu Ile Pro Pro Glu Ala Thr His Ile
385                 390                 395                 400 acc att gat cat gtg tct att ccg cag gaa gca ttc gtt gga gat act         1248
Thr Ile Asp His Val Ser Ile Pro Gln Glu Ala Phe Val Gly Asp Thr
                405                 410                 415 gcg att gtc agt caa tca ttc cct gcc aaa ggg act att gtg gat ctt         1296
```

```
                                        -continued

Ala Ile Val Ser Gln Ser Phe Pro Ala Lys Gly Thr Ile Val Asp Leu
        420                 425                 430 gaa tta ttt gaa gct ttt aat gga atc gta tct ctt gaa tta aaa gga     1344
Glu Leu Phe Glu Ala Phe Asn Gly Ile Val Ser Leu Glu Leu Lys Gly
            435                 440                 445 tca tcc tca caa gat gtt gcc gcg tcc atc cgc aac att cag aaa cag     1392
Ser Ser Ser Gln Asp Val Ala Ala Ser Ile Arg Asn Ile Gln Lys Gln
        450                 455                 460 gca acg att cag tta atg gat gaa tta gtg aag gga                      1428
Ala Thr Ile Gln Leu Met Asp Glu Leu Val Lys Gly
465                 470                 475

<210> SEQ ID NO 17
<211> LENGTH: 1416
<212> TYPE: DNA
<213> ORGANISM: Bacillus subtilis ATCC 15245 and Bacillus subtilis IAM
      1033

<400> SEQUENCE: 17 atg gag aga aaa aca gta ttg gtc atc gct gat ctt gga ggc tgc ccg      48
Met Glu Arg Lys Thr Val Leu Val Ile Ala Asp Leu Gly Gly Cys Pro
  1               5                  10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
                 20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
             35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
         50                  55                  60 tta gct gat ttt gag cat cct gat tcc att tat tgg gcg cat gag gat     240
Leu Ala Asp Phe Glu His Pro Asp Ser Ile Tyr Trp Ala His Glu Asp
 65                  70                  75                  80 cat aac aag cct gag gaa gag gtc gtc gag caa atc gtc aag gtt gcc     288
His Asn Lys Pro Glu Glu Glu Val Val Glu Gln Ile Val Lys Val Ala
                 85                  90                  95 gaa atg ttt ggg gcg gat gcc atc aca aca aac aat gaa tta ttc att     336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ctg aga ggt gcc ggc     384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct     432
Val Gln Ala Ala Glu Asn Ala Arg Asp Lys Asn Lys Met Arg Asp Ala
    130                 135                 140 ttt aat aag gcc gga gtc aaa tcg atc aaa aac aaa cga gtc aca act     480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc     528
Leu Glu Asp Phe Arg Ala Ala Leu Glu Glu Ile Gly Thr Pro Leu Ile
                165                 170                 175 tta aag cct aca tac tta gcg agt tca atc ggt gta acg ctg att acg     576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg     624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc     672
Lys Ser Ile Asn Val Pro Lys Ala Val Thr Phe Glu Ala Pro Phe Ile
    210                 215                 220
```

```
gct gaa gaa ttt tta cag ggt gag tac gga gac tgg tat caa aca gaa      720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag      768
Gly Tyr Ser Asp Tyr Ile Ser Ile Glu Gly Ile Met Ala Asp Gly Glu
            245                 250                 255 tat ttc ccg atc gcc att cat gat aaa acg ccg caa atc ggg ttt aca      816
Tyr Phe Pro Ile Ala Ile His Asp Lys Thr Pro Gln Ile Gly Phe Thr
260                 265                 270 gag aca tcc cac att acg ccg tcc att ctg gat gaa gag gca aaa aag      864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt ggc ctg caa      912
Lys Ile Val Glu Ala Ala Lys Lys Ala Asn Glu Gly Leu Gly Leu Gln
290                 295                 300 aat tgc gca aca cat aca gag atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gca gcc aga ttc gca ggc tgg aat atg att cct     1008
Gly Leu Ile Glu Ser Ala Ala Arg Phe Ala Gly Trp Asn Met Ile Pro
            325                 330                 335 aat att aaa aag gtc ttt ggc ctt gat atg gcg caa tta tta tta gat     1056
Asn Ile Lys Lys Val Phe Gly Leu Asp Met Ala Gln Leu Leu Leu Asp
340                 345                 350 gtc ctc tgt ttc gga aaa gac gcc gat ctg ccg gac gga tta ttg gat     1104
Val Leu Cys Phe Gly Lys Asp Ala Asp Leu Pro Asp Gly Leu Leu Asp
        355                 360                 365 caa gag cct tat tat gtt gcc gac tgc cat ttg tac ccg cag cat ttc     1152
Gln Glu Pro Tyr Tyr Val Ala Asp Cys His Leu Tyr Pro Gln His Phe
370                 375                 380 aaa caa aat ggc cag att cca gaa acc gct gag gat ttg gtc att gaa     1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt     1248
Ala Ile Asp Ile Pro Asp Gly Leu Leu Lys Gly Asp Thr Glu Ile Val
            405                 410                 415 tca ttt tca gcc gca gca cca ggc act tca gtt gat ttg aca ttg ttt     1296
Ser Phe Ser Ala Ala Ala Pro Gly Thr Ser Val Asp Leu Thr Leu Phe
        420                 425                 430 gaa gct ttc aat tcc att gct gca ttt gaa ctg aaa ggc agt aat tca     1344
Glu Ala Phe Asn Ser Ile Ala Ala Phe Glu Leu Lys Gly Ser Asn Ser
            435                 440                 445 cag gat gtg gct gaa tca atc aga caa att cag cag cat gca aag ctg     1392
Gln Asp Val Ala Glu Ser Ile Arg Gln Ile Gln Gln His Ala Lys Leu
450                 455                 460 acg gca aag tat gtg ctg cca gta                                     1416
Thr Ala Lys Tyr Val Leu Pro Val
465                 470

<210> SEQ ID NO 18
<211> LENGTH: 93
<212> TYPE: PRT
<213> ORGANISM: Bacillus subtilis 168

<400> SEQUENCE: 18

Gly Ala Gly Val Gln Ala Ala Glu Asn Ala Arg Asp Lys Asn Lys Met
1               5                   10                  15

Arg Asp Ala Phe Asn Lys Ala Gly Val Lys Ser Ile Lys Asn Lys Arg
            20                  25                  30

Val Thr Thr Leu Glu Asp Phe Arg Ala Ala Leu Glu Glu Ile Gly Thr
        35                  40                  45
```

```
Pro Leu Ile Leu Lys Pro Thr Tyr Leu Ala Ser Ser Ile Gly Val Thr
         50                  55                  60

Leu Ile Thr Asp Thr Glu Thr Ala Glu Asp Glu Phe Asn Arg Val Asn
 65                  70                  75                  80

Asp Tyr Leu Lys Ser Ile Asn Val Pro Lys Ala Val Thr
             85                  90
```

<210> SEQ ID NO 19
<211> LENGTH: 279
<212> TYPE: DNA
<213> ORGANISM: Bacillus subtilis 168

<400> SEQUENCE: 19

```
ggt gcc ggc gtg cag gca gcc gaa aat gcc aga gat aaa aat aaa atg    48
Gly Ala Gly Val Gln Ala Ala Glu Asn Ala Arg Asp Lys Asn Lys Met
 1               5                  10                  15 agg gac gct ttt aat aag gcc gga gtc aaa tcg atc aaa aac aaa cga    96
Arg Asp Ala Phe Asn Lys Ala Gly Val Lys Ser Ile Lys Asn Lys Arg
             20                  25                  30 gtc aca act ctt gaa gat ttc cgt gct gct ctt gaa gag atc ggc aca   144
Val Thr Thr Leu Glu Asp Phe Arg Ala Ala Leu Glu Glu Ile Gly Thr
         35                  40                  45 cct ctt atc tta aag cct aca tac tta gcg agt tct atc ggt gta acg   192
Pro Leu Ile Leu Lys Pro Thr Tyr Leu Ala Ser Ser Ile Gly Val Thr
     50                  55                  60 ctg att acg gac act gag acg gca gaa gat gaa ttt aac aga gtc aat   240
Leu Ile Thr Asp Thr Glu Thr Ala Glu Asp Glu Phe Asn Arg Val Asn
 65                  70                  75                  80 gac tat ctg aaa tca att aac gtg cca aag gcg gtt acg               279
Asp Tyr Leu Lys Ser Ile Asn Val Pro Lys Ala Val Thr
             85                  90
```

<210> SEQ ID NO 20
<211> LENGTH: 503
<212> TYPE: PRT
<213> ORGANISM: Escherichia coli

<400> SEQUENCE: 20

```
Met Glu Phe Ser Val Lys Ser Gly Ser Pro Glu Lys Gln Arg Ser Ala
 1               5                  10                  15

Cys Ile Val Val Gly Val Phe Glu Pro Arg Arg Leu Ser Pro Ile Ala
             20                  25                  30

Glu Gln Leu Asp Lys Ile Ser Asp Gly Tyr Ile Ser Ala Leu Leu Arg
         35                  40                  45

Arg Gly Glu Leu Glu Gly Lys Pro Gly Gln Thr Leu Leu Leu His His
     50                  55                  60

Val Pro Asn Val Leu Ser Glu Arg Ile Leu Ile Gly Cys Gly Lys
 65                  70                  75                  80

Glu Arg Glu Leu Asp Glu Arg Gln Tyr Lys Gln Val Ile Gln Lys Thr
             85                  90                  95

Ile Asn Thr Leu Asn Asp Thr Gly Ser Met Glu Ala Val Cys Phe Leu
        100                 105                 110

Thr Glu Leu His Val Lys Gly Arg Asn Asn Tyr Trp Lys Val Arg Gln
        115                 120                 125

Ala Val Glu Thr Ala Lys Glu Thr Leu Tyr Ser Phe Asp Gln Leu Lys
    130                 135                 140

Thr Asn Lys Ser Glu Pro Arg Arg Pro Leu Arg Lys Met Val Phe Asn
145                 150                 155                 160
```

```
Val Pro Thr Arg Arg Glu Leu Thr Ser Gly Glu Arg Ala Ile Gln His
            165                 170                 175

Gly Leu Ala Ile Ala Ala Gly Ile Lys Ala Ala Lys Asp Leu Gly Asn
            180                 185                 190

Met Pro Pro Asn Ile Cys Asn Ala Ala Tyr Leu Ala Ser Gln Ala Arg
            195                 200                 205

Gln Leu Ala Asp Ser Tyr Ser Lys Asn Val Ile Thr Arg Val Ile Gly
            210                 215                 220

Glu Gln Gln Met Lys Glu Leu Gly Met His Ser Tyr Leu Ala Val Gly
225                 230                 235                 240

Gln Gly Ser Gln Asn Glu Ser Leu Met Ser Val Ile Glu Tyr Lys Gly
            245                 250                 255

Asn Ala Ser Glu Asp Ala Arg Pro Ile Val Leu Val Gly Lys Gly Leu
            260                 265                 270

Thr Phe Asp Ser Gly Gly Ile Ser Ile Lys Pro Ser Glu Gly Met Asp
            275                 280                 285

Glu Met Lys Tyr Asp Met Cys Gly Ala Ala Ala Val Tyr Gly Val Met
            290                 295                 300

Arg Met Val Ala Glu Leu Gln Leu Pro Ile Asn Val Ile Gly Val Leu
305                 310                 315                 320

Ala Gly Cys Glu Asn Met Pro Gly Gly Arg Ala Tyr Arg Pro Gly Asp
            325                 330                 335

Val Leu Thr Thr Met Ser Gly Gln Thr Val Glu Val Leu Asn Thr Asp
            340                 345                 350

Ala Glu Gly Arg Leu Val Leu Cys Asp Val Leu Thr Tyr Val Glu Arg
            355                 360                 365

Phe Glu Pro Glu Ala Val Ile Asp Val Ala Thr Leu Thr Gly Ala Cys
            370                 375                 380

Val Ile Ala Leu Gly His His Ile Thr Gly Leu Met Ala Asn His Asn
385                 390                 395                 400

Pro Leu Ala His Glu Leu Ile Ala Ala Ser Glu Gln Ser Gly Asp Arg
            405                 410                 415

Ala Trp Arg Leu Pro Leu Gly Asp Glu Tyr Gln Glu Gln Leu Glu Ser
            420                 425                 430

Asn Phe Ala Asp Met Ala Asn Ile Gly Gly Arg Pro Gly Gly Ala Ile
            435                 440                 445

Thr Ala Gly Cys Phe Leu Ser Arg Phe Thr Arg Lys Tyr Asn Trp Ala
            450                 455                 460

His Leu Asp Ile Ala Gly Thr Ala Trp Arg Ser Gly Lys Ala Lys Gly
465                 470                 475                 480

Ala Thr Gly Arg Pro Val Ala Leu Leu Ala Gln Phe Leu Leu Asn Arg
            485                 490                 495

Ala Gly Phe Asn Gly Glu Glu
            500

<210> SEQ ID NO 21
<211> LENGTH: 427
<212> TYPE: PRT
<213> ORGANISM: Escherichia coli

<400> SEQUENCE: 21

Met Thr Glu Ala Met Lys Ile Thr Leu Ser Thr Gln Pro Ala Asp Ala
1               5                   10                  15

Arg Trp Gly Glu Lys Ala Thr Tyr Ser Ile Asn Asn Asp Gly Ile Thr
            20                  25                  30
```

```
Leu His Leu Asn Gly Ala Asp Leu Gly Leu Ile Gln Arg Ala Ala
         35                  40                  45

Arg Lys Ile Asp Gly Leu Gly Ile Lys His Val Gln Leu Ser Gly Glu
 50                  55                  60

Gly Trp Asp Ala Asp Arg Cys Trp Ala Phe Trp Gln Gly Tyr Lys Ala
 65                  70                  75                  80

Pro Lys Gly Thr Arg Lys Val Val Trp Pro Asp Leu Asp Asp Ala Gln
                 85                  90                  95

Arg Gln Glu Leu Asp Asn Arg Leu Met Ile Ile Asp Trp Val Arg Asp
             100                 105                 110

Thr Ile Asn Ala Pro Ala Glu Glu Leu Gly Pro Ser Gln Leu Ala Gln
         115                 120                 125

Arg Ala Val Asp Leu Ile Ser Asn Val Ala Gly Asp Arg Val Thr Tyr
     130                 135                 140

Arg Ile Thr Lys Gly Glu Asp Leu Arg Glu Gln Gly Tyr Met Gly Leu
145                 150                 155                 160

His Thr Val Gly Arg Gly Ser Glu Arg Ser Pro Val Leu Leu Ala Leu
                165                 170                 175

Asp Tyr Asn Pro Thr Gly Asp Lys Glu Ala Pro Val Tyr Ala Cys Leu
            180                 185                 190

Val Gly Lys Gly Ile Thr Phe Asp Ser Gly Gly Tyr Ser Ile Lys Gln
        195                 200                 205

Thr Ala Phe Met Asp Ser Met Lys Ser Asp Met Gly Gly Ala Ala Thr
    210                 215                 220

Val Thr Gly Ala Leu Ala Phe Ala Ile Thr Arg Gly Leu Asn Lys Arg
225                 230                 235                 240

Val Lys Leu Phe Leu Cys Cys Ala Asp Asn Leu Ile Ser Gly Asn Ala
                245                 250                 255

Phe Lys Leu Gly Asp Ile Ile Thr Tyr Arg Asn Gly Lys Lys Val Glu
            260                 265                 270

Val Met Asn Thr Asp Ala Glu Gly Arg Leu Val Leu Ala Asp Gly Leu
        275                 280                 285

Ile Asp Ala Ser Ala Gln Lys Pro Glu Met Ile Ile Asp Ala Ala Thr
    290                 295                 300

Leu Thr Gly Ala Ala Lys Thr Ala Leu Gly Asn Asp Tyr His Ala Leu
305                 310                 315                 320

Phe Ser Phe Asp Asp Ala Leu Ala Gly Arg Leu Leu Ala Ser Ala Ala
                325                 330                 335

Gln Glu Asn Glu Pro Phe Trp Arg Leu Pro Leu Ala Glu Phe His Arg
            340                 345                 350

Ser Gln Leu Pro Ser Asn Phe Ala Glu Leu Asn Asn Thr Gly Ser Ala
        355                 360                 365

Ala Tyr Pro Ala Gly Ala Ser Thr Ala Ala Gly Phe Leu Ser His Phe
    370                 375                 380

Val Glu Asn Tyr Gln Gln Gly Trp Leu His Ile Asp Cys Ser Ala Thr
385                 390                 395                 400

Tyr Arg Lys Ala Pro Val Glu Gln Trp Ser Ala Gly Ala Thr Gly Leu
                405                 410                 415

Gly Val Arg Thr Ile Ala Asn Leu Leu Thr Ala
            420                 425

<210> SEQ ID NO 22
<211> LENGTH: 485
<212> TYPE: PRT
<213> ORGANISM: Escherichia coli
```

<400> SEQUENCE: 22

```
Met Ser Glu Leu Ser Gln Leu Ser Pro Gln Pro Leu Trp Asp Ile Phe
 1               5                  10                  15

Ala Lys Ile Cys Ser Ile Pro His Pro Ser Tyr His Glu Glu Gln Leu
            20                  25                  30

Ala Glu Tyr Ile Val Gly Trp Ala Lys Glu Lys Gly Phe His Val Glu
        35                  40                  45

Arg Asp Gln Val Gly Asn Ile Leu Ile Arg Lys Pro Ala Thr Ala Gly
    50                  55                  60

Met Glu Asn Arg Lys Pro Val Val Leu Gln Ala His Leu Asp Met Val
65                  70                  75                  80

Pro Gln Lys Asn Asp Thr Val His Asp Phe Thr Lys Asp Pro Ile
                85                  90                  95

Gln Pro Tyr Ile Asp Gly Glu Trp Val Lys Ala Arg Gly Thr Thr Leu
            100                 105                 110

Gly Ala Asp Asn Gly Ile Gly Met Ala Ser Ala Leu Ala Val Leu Ala
        115                 120                 125

Asp Glu Asn Val Val His Gly Pro Leu Glu Val Leu Leu Thr Met Thr
    130                 135                 140

Glu Glu Ala Gly Met Asp Gly Ala Phe Gly Leu Gln Gly Asn Trp Leu
145                 150                 155                 160

Gln Ala Asp Ile Leu Ile Asn Thr Asp Ser Glu Glu Gly Glu Ile
                165                 170                 175

Tyr Met Gly Cys Ala Gly Gly Ile Asp Phe Thr Ser Asn Leu His Leu
            180                 185                 190

Asp Arg Glu Ala Val Pro Ala Gly Phe Glu Thr Phe Lys Leu Thr Leu
        195                 200                 205

Lys Gly Leu Lys Gly Gly His Ser Gly Gly Glu Ile His Val Gly Leu
    210                 215                 220

Gly Asn Ala Asn Lys Leu Leu Val Arg Phe Leu Ala Gly His Ala Glu
225                 230                 235                 240

Glu Leu Asp Leu Arg Leu Ile Asp Phe Asn Gly Gly Thr Leu Arg Asn
                245                 250                 255

Ala Ile Pro Arg Glu Ala Phe Ala Thr Ile Ala Val Ala Ala Asp Lys
            260                 265                 270

Val Asp Val Leu Lys Ser Leu Val Asn Thr Tyr Gln Glu Ile Leu Lys
        275                 280                 285

Asn Glu Leu Ala Glu Lys Glu Lys Asn Leu Ala Leu Leu Asp Ser
    290                 295                 300

Val Ala Asn Asp Lys Ala Ala Leu Ile Ala Lys Ser Arg Asp Thr Phe
305                 310                 315                 320

Ile Arg Leu Leu Asn Ala Thr Pro Asn Gly Val Ile Arg Asn Ser Asp
                325                 330                 335

Val Ala Lys Gly Val Val Glu Thr Ser Leu Asn Val Gly Val Val Thr
            340                 345                 350

Met Thr Asp Asn Asn Val Glu Ile His Cys Leu Ile Arg Ser Leu Ile
        355                 360                 365

Asp Ser Gly Lys Asp Tyr Val Val Ser Met Leu Asp Ser Leu Gly Lys
    370                 375                 380

Leu Ala Gly Ala Lys Thr Glu Ala Lys Gly Ala Tyr Pro Gly Trp Gln
385                 390                 395                 400

Pro Asp Ala Asn Ser Pro Val Met His Leu Val Arg Glu Thr Tyr Gln
                405                 410                 415
```

```
Arg Leu Phe Asn Lys Thr Pro Asn Ile Gln Ile Ile His Ala Gly Leu
            420                 425                 430

Glu Cys Gly Leu Phe Lys Lys Pro Tyr Pro Glu Met Asp Met Val Ser
        435                 440                 445

Ile Gly Pro Thr Ile Thr Gly Pro His Ser Pro Asp Glu Gln Val His
    450                 455                 460

Ile Glu Ser Val Gly His Tyr Trp Thr Leu Leu Thr Glu Leu Leu Lys
465                 470                 475                 480

Glu Ile Pro Ala Lys
                485

<210> SEQ ID NO 23
<211> LENGTH: 870
<212> TYPE: PRT
<213> ORGANISM: Escherichia coli

<400> SEQUENCE: 23

Met Thr Gln Gln Pro Gln Ala Lys Tyr Arg His Asp Tyr Arg Ala Pro
  1               5                  10                  15

Asp Tyr Gln Ile Thr Asp Ile Asp Leu Thr Phe Asp Leu Asp Ala Gln
             20                  25                  30

Lys Thr Val Val Thr Ala Val Ser Gln Ala Val Arg His Gly Ala Ser
         35                  40                  45

Asp Ala Pro Leu Arg Leu Asn Gly Glu Asp Leu Lys Leu Val Ser Val
     50                  55                  60

His Ile Asn Asp Glu Pro Trp Thr Ala Trp Lys Glu Glu Gly Ala
 65                  70                  75                  80

Leu Val Ile Ser Asn Leu Pro Glu Arg Phe Thr Leu Lys Ile Ile Asn
                 85                  90                  95

Glu Ile Ser Pro Ala Ala Asn Thr Ala Leu Glu Gly Leu Tyr Gln Ser
            100                 105                 110

Gly Asp Ala Leu Cys Thr Gln Cys Glu Ala Glu Gly Phe Arg His Ile
        115                 120                 125

Thr Tyr Tyr Leu Asp Arg Pro Asp Val Leu Ala Arg Phe Thr Thr Lys
    130                 135                 140

Ile Ile Ala Asp Lys Ile Lys Tyr Pro Phe Leu Leu Ser Asn Gly Asn
145                 150                 155                 160

Arg Val Ala Gln Gly Glu Leu Glu Asn Gly Arg His Trp Val Gln Trp
                165                 170                 175

Gln Asp Pro Phe Pro Lys Pro Cys Tyr Leu Phe Ala Leu Val Ala Gly
            180                 185                 190

Asp Phe Asp Val Leu Arg Asp Thr Phe Thr Thr Arg Ser Gly Arg Glu
        195                 200                 205

Val Ala Leu Glu Leu Tyr Val Asp Arg Gly Asn Leu Asp Arg Ala Pro
    210                 215                 220

Trp Ala Met Thr Ser Leu Lys Asn Ser Met Lys Trp Asp Glu Glu Arg
225                 230                 235                 240

Phe Gly Leu Glu Tyr Asp Leu Asp Ile Tyr Met Ile Val Ala Val Asp
                245                 250                 255

Phe Phe Asn Met Gly Ala Met Glu Asn Lys Gly Leu Asn Ile Phe Asn
            260                 265                 270

Ser Lys Tyr Val Leu Ala Arg Thr Asp Thr Ala Thr Asp Lys Asp Tyr
        275                 280                 285

Leu Asp Ile Glu Arg Val Ile Gly His Glu Tyr Phe His Asn Trp Thr
    290                 295                 300
```

```
Gly Asn Arg Val Thr Cys Arg Asp Trp Phe Gln Leu Ser Leu Lys Glu
305                 310                 315                 320

Gly Leu Thr Val Phe Arg Asp Gln Glu Phe Ser Ser Asp Leu Gly Ser
                325                 330                 335

Arg Ala Val Asn Arg Ile Asn Asn Val Arg Thr Met Arg Gly Leu Gln
            340                 345                 350

Phe Ala Glu Asp Ala Ser Pro Met Ala His Pro Ile Arg Pro Asp Met
        355                 360                 365

Val Ile Glu Met Asn Asn Phe Tyr Thr Leu Thr Val Tyr Glu Lys Gly
    370                 375                 380

Ala Glu Val Ile Arg Met Ile His Thr Leu Leu Gly Glu Glu Asn Phe
385                 390                 395                 400

Gln Lys Gly Met Gln Leu Tyr Phe Glu Arg His Asp Gly Ser Ala Ala
                405                 410                 415

Thr Cys Asp Asp Phe Val Gln Ala Met Glu Asp Ala Ser Asn Val Asp
            420                 425                 430

Leu Ser His Phe Arg Arg Trp Tyr Ser Gln Ser Gly Thr Pro Ile Val
        435                 440                 445

Thr Val Lys Asp Asp Tyr Asn Pro Glu Thr Glu Gln Tyr Thr Leu Thr
    450                 455                 460

Ile Ser Gln Arg Thr Pro Ala Thr Pro Asp Gln Ala Glu Lys Gln Pro
465                 470                 475                 480

Leu His Ile Pro Phe Ala Ile Glu Leu Tyr Asp Asn Glu Gly Lys Val
                485                 490                 495

Ile Pro Leu Gln Lys Gly Gly His Pro Val Asn Ser Val Leu Asn Val
            500                 505                 510

Thr Gln Ala Glu Gln Thr Phe Val Phe Asp Asn Val Tyr Phe Gln Pro
        515                 520                 525

Val Pro Ala Leu Leu Cys Glu Phe Ser Ala Pro Val Lys Leu Glu Tyr
    530                 535                 540

Lys Trp Ser Asp Gln Gln Leu Thr Phe Leu Met Arg His Ala Arg Asn
545                 550                 555                 560

Asp Phe Ser Arg Trp Asp Ala Ala Gln Ser Leu Leu Ala Thr Tyr Ile
                565                 570                 575

Lys Leu Asn Val Ala Arg His Gln Gln Gly Gln Pro Leu Ser Leu Pro
            580                 585                 590

Val His Val Ala Asp Ala Phe Arg Ala Val Leu Leu Asp Glu Lys Ile
        595                 600                 605

Asp Pro Ala Leu Ala Ala Glu Ile Leu Thr Leu Pro Ser Val Asn Glu
    610                 615                 620

Met Ala Glu Leu Phe Asp Ile Ile Asp Pro Ile Ala Ile Ala Glu Val
625                 630                 635                 640

Arg Glu Ala Leu Thr Arg Thr Leu Ala Thr Glu Leu Ala Asp Glu Leu
                645                 650                 655

Leu Ala Ile Tyr Asn Ala Asn Tyr Gln Ser Glu Tyr Arg Val Glu His
            660                 665                 670

Glu Asp Ile Ala Lys Arg Thr Leu Arg Asn Ala Cys Leu Arg Phe Leu
        675                 680                 685

Ala Phe Gly Glu Thr His Leu Ala Asp Val Leu Val Ser Lys Gln Phe
    690                 695                 700

His Glu Ala Asn Asn Met Thr Asp Ala Leu Ala Ala Leu Ser Ala Ala
705                 710                 715                 720

Val Ala Ala Gln Leu Pro Cys Arg Asp Ala Leu Met Gln Glu Tyr Asp
```

```
                    725                 730                 735
Asp Lys Trp His Gln Asn Gly Leu Val Met Asp Lys Trp Phe Ile Leu
            740                 745                 750

Gln Ala Thr Ser Pro Ala Ala Asn Val Leu Glu Thr Val Arg Gly Leu
        755                 760                 765

Leu Gln His Arg Ser Phe Thr Met Ser Asn Pro Asn Arg Ile Arg Ser
    770                 775                 780

Leu Ile Gly Ala Phe Ala Gly Ser Asn Pro Ala Ala Phe His Ala Glu
785                 790                 795                 800

Asp Gly Ser Gly Tyr Leu Phe Leu Val Glu Met Leu Thr Asp Leu Asn
            805                 810                 815

Ser Arg Asn Pro Gln Val Ala Ser Arg Leu Ile Glu Pro Leu Ile Arg
        820                 825                 830

Leu Lys Arg Tyr Asp Ala Lys Arg Gln Glu Lys Met Arg Ala Ala Leu
    835                 840                 845

Glu Gln Leu Lys Gly Leu Glu Asn Leu Ser Gly Asp Leu Tyr Glu Lys
850                 855                 860

Ile Thr Lys Ala Leu Ala
865                 870

<210> SEQ ID NO 24
<211> LENGTH: 535
<212> TYPE: PRT
<213> ORGANISM: Escherichia coli

<400> SEQUENCE: 24

Met Arg Ile Ser Leu Lys Lys Ser Gly Met Leu Lys Leu Gly Leu Ser
1               5                   10                  15

Leu Val Ala Met Thr Val Ala Ala Ser Val Gln Ala Lys Thr Leu Val
            20                  25                  30

Tyr Cys Ser Glu Gly Ser Pro Glu Gly Phe Asn Pro Gln Leu Phe Thr
        35                  40                  45

Ser Gly Thr Thr Tyr Asp Ala Ser Ser Val Pro Leu Tyr Asn Arg Leu
    50                  55                  60

Val Glu Phe Lys Ile Gly Thr Thr Glu Val Ile Pro Gly Leu Ala Glu
65                  70                  75                  80

Lys Trp Glu Val Ser Glu Asp Gly Lys Thr Tyr Thr Phe His Leu Arg
                85                  90                  95

Lys Gly Val Lys Trp His Asp Asn Lys Glu Phe Lys Pro Thr Arg Glu
            100                 105                 110

Leu Asn Ala Asp Asp Val Val Phe Ser Phe Asp Arg Gln Lys Asn Ala
        115                 120                 125

Gln Asn Pro Tyr His Lys Val Ser Gly Gly Ser Tyr Glu Tyr Phe Glu
    130                 135                 140

Gly Met Gly Leu Pro Glu Leu Ile Ser Glu Val Lys Lys Val Asp Asp
145                 150                 155                 160

Asn Thr Val Gln Phe Val Leu Thr Arg Pro Glu Ala Pro Phe Leu Ala
                165                 170                 175

Asp Leu Ala Met Asp Phe Ala Ser Ile Leu Ser Lys Glu Tyr Ala Asp
            180                 185                 190

Ala Met Met Lys Ala Gly Thr Pro Glu Lys Leu Asp Leu Asn Pro Ile
        195                 200                 205

Gly Thr Gly Pro Phe Gln Leu Gln Gln Tyr Gln Lys Asp Ser Arg Ile
    210                 215                 220

Arg Tyr Lys Ala Phe Asp Gly Tyr Trp Gly Thr Lys Pro Gln Ile Asp
```

```
                225                 230                 235                 240
Thr Leu Val Phe Ser Ile Thr Pro Asp Ala Ser Val Arg Tyr Ala Lys
                    245                 250                 255
Leu Gln Lys Asn Glu Cys Gln Val Met Pro Tyr Pro Asn Pro Ala Asp
                260                 265                 270
Ile Ala Arg Met Lys Gln Asp Lys Ser Ile Asn Leu Met Glu Met Pro
            275                 280                 285
Gly Leu Asn Val Gly Tyr Leu Ser Tyr Asn Val Gln Lys Lys Pro Leu
        290                 295                 300
Asp Asp Val Lys Val Arg Gln Ala Leu Thr Tyr Ala Val Asn Lys Asp
305                 310                 315                 320
Ala Ile Ile Lys Ala Val Tyr Gln Gly Ala Gly Val Ser Ala Lys Asn
                325                 330                 335
Leu Ile Pro Pro Thr Met Trp Gly Tyr Asn Asp Asp Val Gln Asp Tyr
                340                 345                 350
Thr Tyr Asp Pro Glu Lys Ala Lys Ala Leu Leu Lys Glu Ala Gly Leu
            355                 360                 365
Glu Lys Gly Phe Ser Ile Asp Leu Trp Ala Met Pro Val Gln Arg Pro
        370                 375                 380
Tyr Asn Pro Asn Ala Arg Arg Met Ala Glu Met Ile Gln Ala Asp Trp
385                 390                 395                 400
Ala Lys Val Gly Val Gln Ala Lys Ile Val Thr Tyr Glu Trp Gly Glu
                405                 410                 415
Tyr Leu Lys Arg Ala Lys Asp Gly Glu His Gln Thr Val Met Met Gly
                420                 425                 430
Trp Thr Gly Asp Asn Gly Asp Pro Asp Asn Phe Phe Ala Thr Leu Phe
            435                 440                 445
Ser Cys Ala Ala Ser Glu Gln Gly Ser Asn Tyr Ser Lys Trp Cys Tyr
        450                 455                 460
Lys Pro Phe Glu Asp Leu Ile Gln Pro Ala Arg Ala Thr Asp Asp His
465                 470                 475                 480
Asn Lys Arg Val Glu Leu Tyr Lys Gln Ala Gln Val Val Met His Asp
                485                 490                 495
Gln Ala Pro Ala Leu Ile Ile Ala His Ser Thr Val Phe Glu Pro Val
                500                 505                 510
Arg Lys Glu Val Lys Gly Tyr Val Val Asp Pro Leu Gly Lys His His
            515                 520                 525
Phe Glu Asn Val Ser Ile Glu
        530                 535

<210> SEQ ID NO 25
<211> LENGTH: 339
<212> TYPE: PRT
<213> ORGANISM: Escherichia coli

<400> SEQUENCE: 25

Met Leu Gln Phe Ile Leu Arg Arg Leu Gly Leu Val Ile Pro Thr Phe
1               5                   10                  15
Ile Gly Ile Thr Leu Leu Thr Phe Ala Phe Val His Met Ile Pro Gly
                20                  25                  30
Asp Pro Val Met Ile Met Ala Gly Glu Arg Gly Ile Ser Pro Glu Arg
            35                  40                  45
His Ala Gln Leu Leu Ala Glu Leu Gly Leu Asp Lys Pro Met Trp Gln
        50                  55                  60
Gln Tyr Leu His Tyr Ile Trp Gly Val Met His Gly Asp Leu Gly Ile
```

```
                65                  70                  75                  80
Ser Met Lys Ser Arg Ile Pro Val Trp Glu Glu Phe Val Pro Arg Phe
                    85                  90                  95
Gln Ala Thr Leu Glu Leu Gly Val Cys Ala Met Ile Phe Ala Thr Ala
                    100                 105                 110
Val Gly Ile Pro Val Gly Val Leu Ala Val Lys Arg Gly Ser Ile
                    115                 120                 125
Phe Asp His Thr Ala Val Gly Leu Ala Leu Thr Gly Tyr Ser Met Pro
    130                 135                 140
Ile Phe Trp Trp Gly Met Met Leu Ile Met Leu Val Ser Val His Trp
145                 150                 155                 160
Asn Leu Thr Pro Val Ser Gly Arg Val Ser Asp Met Val Phe Leu Asp
                    165                 170                 175
Asp Ser Asn Pro Leu Thr Gly Phe Met Leu Ile Asp Thr Ala Ile Trp
                    180                 185                 190
Gly Glu Asp Gly Asn Phe Ile Asp Ala Val Ala His Met Ile Leu Pro
                    195                 200                 205
Ala Ile Val Leu Gly Thr Ile Pro Leu Ala Val Ile Val Arg Met Thr
    210                 215                 220
Arg Ser Ser Met Leu Glu Val Leu Gly Glu Asp Tyr Ile Arg Thr Ala
225                 230                 235                 240
Arg Ala Lys Gly Leu Thr Arg Met Arg Val Ile Val His Ala Leu
                    245                 250                 255
Arg Asn Ala Met Leu Pro Val Val Thr Val Ile Gly Leu Gln Val Gly
                    260                 265                 270
Thr Leu Leu Ala Gly Ala Ile Leu Thr Glu Thr Ile Phe Ser Trp Pro
    275                 280                 285
Gly Leu Gly Arg Trp Leu Ile Asp Ala Leu Gln Arg Arg Asp Tyr Pro
    290                 295                 300
Val Val Gln Gly Gly Val Leu Leu Val Ala Thr Met Ile Ile Leu Val
305                 310                 315                 320
Asn Leu Leu Val Asp Leu Leu Tyr Gly Val Val Asn Pro Arg Ile Arg
                    325                 330                 335
His Lys Lys

<210> SEQ ID NO 26
<211> LENGTH: 300
<212> TYPE: PRT
<213> ORGANISM: Escherichia coli

<400> SEQUENCE: 26

Met Ser Gln Val Thr Glu Asn Lys Val Ile Ser Ala Pro Val Pro Met
1               5                   10                  15
Thr Pro Leu Gln Glu Phe Trp His Tyr Phe Lys Arg Asn Lys Gly Ala
                    20                  25                  30
Val Val Gly Leu Val Tyr Val Ile Val Leu Phe Ile Ala Ile Phe
                    35                  40                  45
Ala Asn Trp Ile Ala Pro Tyr Asn Pro Ala Glu Gln Phe Arg Asp Ala
    50                  55                  60
Leu Leu Ala Pro Pro Ala Trp Gln Glu Gly Gly Ser Met Ala His Leu
65                  70                  75                  80
Leu Gly Thr Asp Asp Val Gly Arg Asp Val Leu Ser Arg Leu Met Tyr
                    85                  90                  95
Gly Ala Arg Leu Ser Leu Leu Val Gly Cys Leu Val Val Val Leu Ser
                    100                 105                 110
```

```
Leu Ile Met Gly Val Ile Leu Gly Leu Ile Ala Gly Tyr Phe Gly Gly
            115                 120                 125

Leu Val Asp Asn Ile Ile Met Arg Val Val Asp Ile Met Leu Ala Leu
130                 135                 140

Pro Ser Leu Leu Leu Ala Leu Val Leu Val Ala Ile Phe Gly Pro Ser
145                 150                 155                 160

Ile Gly Asn Ala Ala Leu Ala Leu Thr Phe Val Ala Leu Pro His Tyr
                165                 170                 175

Val Arg Leu Thr Arg Ala Ala Val Leu Val Glu Val Asn Arg Asp Tyr
            180                 185                 190

Val Thr Ala Ser Arg Val Ala Gly Ala Gly Ala Met Arg Gln Met Phe
        195                 200                 205

Ile Asn Ile Phe Pro Asn Cys Leu Ala Pro Leu Ile Val Gln Ala Ser
210                 215                 220

Leu Gly Phe Ser Asn Ala Ile Leu Asp Met Ala Ala Leu Gly Phe Leu
225                 230                 235                 240

Gly Met Gly Ala Gln Pro Pro Thr Pro Glu Trp Gly Thr Met Leu Ser
                245                 250                 255

Asp Val Leu Gln Phe Ala Gln Ser Ala Trp Trp Val Val Thr Phe Pro
            260                 265                 270

Gly Leu Ala Ile Leu Leu Thr Val Leu Ala Phe Asn Leu Met Gly Asp
        275                 280                 285

Gly Leu Arg Asp Ala Leu Asp Pro Lys Leu Lys Gln
    290                 295                 300

<210> SEQ ID NO 27
<211> LENGTH: 327
<212> TYPE: PRT
<213> ORGANISM: Escherichia coli

<400> SEQUENCE: 27

Met Ala Leu Leu Asn Val Asp Lys Leu Ser Val His Phe Gly Asp Glu
  1               5                  10                  15

Ser Ala Pro Phe Arg Ala Val Asp Arg Ile Ser Tyr Ser Val Lys Gln
                20                  25                  30

Gly Glu Val Val Gly Ile Val Gly Glu Ser Gly Ser Gly Lys Ser Val
            35                  40                  45

Ser Ser Leu Ala Ile Met Gly Leu Ile Asp Tyr Pro Gly Arg Val Met
        50                  55                  60

Ala Glu Lys Leu Glu Phe Asn Gly Gln Asp Leu Gln Arg Ile Ser Glu
65                  70                  75                  80

Lys Glu Arg Arg Asn Leu Val Gly Ala Glu Val Ala Met Ile Phe Gln
                85                  90                  95

Asp Pro Met Thr Ser Leu Asn Pro Cys Tyr Thr Val Gly Phe Gln Ile
            100                 105                 110

Met Glu Ala Ile Lys Val His Gln Gly Gly Asn Lys Ser Thr Arg Arg
        115                 120                 125

Gln Arg Ala Ile Asp Leu Leu Asn Gln Val Gly Ile Pro Asp Pro Ala
    130                 135                 140

Ser Arg Leu Asp Val Tyr Pro His Gln Leu Ser Gly Gly Met Ser Gln
145                 150                 155                 160

Arg Val Met Ile Ala Met Ala Ile Ala Cys Arg Pro Lys Leu Leu Ile
                165                 170                 175

Ala Asp Glu Pro Thr Thr Ala Leu Asp Val Thr Ile Gln Ala Gln Ile
            180                 185                 190
```

```
Ile Glu Leu Leu Leu Glu Leu Gln Gln Lys Glu Asn Met Ala Leu Val
            195                 200                 205

Leu Ile Thr His Asp Leu Ala Leu Val Ala Glu Ala Ala His Lys Ile
210                 215                 220

Ile Val Met Tyr Ala Gly Gln Val Val Glu Thr Gly Asp Ala His Ala
225                 230                 235                 240

Ile Phe His Ala Pro Arg His Pro Tyr Thr Gln Ala Leu Leu Arg Ala
                245                 250                 255

Leu Pro Glu Phe Ala Gln Asp Lys Glu Arg Leu Ala Ser Leu Pro Gly
            260                 265                 270

Val Val Pro Gly Lys Tyr Asp Arg Pro Asn Gly Cys Leu Leu Asn Pro
        275                 280                 285

Arg Cys Pro Tyr Ala Thr Asp Arg Cys Arg Ala Glu Glu Pro Ala Leu
    290                 295                 300

Asn Met Leu Ala Asp Gly Arg Gln Ser Lys Cys His Tyr Pro Leu Asp
305                 310                 315                 320

Asp Ala Gly Arg Pro Thr Leu
                325

<210> SEQ ID NO 28
<211> LENGTH: 334
<212> TYPE: PRT
<213> ORGANISM: Escherichia coli

<400> SEQUENCE: 28

Met Ser Thr Gln Glu Ala Thr Leu Gln Gln Pro Leu Leu Gln Ala Ile
1               5                   10                  15

Asp Leu Lys Lys His Tyr Pro Val Lys Lys Gly Met Phe Ala Pro Glu
            20                  25                  30

Arg Leu Val Lys Ala Leu Asp Gly Val Ser Phe Asn Leu Glu Arg Gly
        35                  40                  45

Lys Thr Leu Ala Val Val Gly Glu Ser Gly Cys Gly Lys Ser Thr Leu
    50                  55                  60

Gly Arg Leu Leu Thr Met Ile Glu Met Pro Thr Gly Gly Glu Leu Tyr
65                  70                  75                  80

Tyr Gln Gly Gln Asp Leu Leu Lys His Asp Pro Gln Ala Gln Lys Leu
                85                  90                  95

Arg Arg Gln Lys Ile Gln Ile Val Phe Gln Asn Pro Tyr Gly Ser Leu
            100                 105                 110

Asn Pro Arg Lys Lys Val Gly Gln Ile Leu Glu Glu Pro Leu Leu Ile
        115                 120                 125

Asn Thr Ser Leu Ser Lys Glu Gln Arg Arg Glu Lys Ala Leu Ser Met
    130                 135                 140

Met Ala Lys Val Gly Leu Lys Thr Glu His Tyr Asp Arg Tyr Pro His
145                 150                 155                 160

Met Phe Ser Gly Gly Gln Arg Gln Arg Ile Ala Ile Ala Arg Gly Leu
                165                 170                 175

Met Leu Asp Pro Asp Val Val Ile Ala Asp Glu Pro Val Ser Ala Leu
            180                 185                 190

Asp Val Ser Val Arg Ala Gln Val Leu Asn Leu Met Met Asp Leu Gln
        195                 200                 205

Gln Glu Leu Gly Leu Ser Tyr Val Phe Ile Ser His Asp Leu Ser Val
    210                 215                 220

Val Glu His Ile Ala Asp Glu Val Met Val Met Tyr Leu Gly Arg Cys
225                 230                 235                 240
```

| | | | | | | | | | | | | |
|---|---|---|---|---|---|---|---|---|---|---|---|---|
|Val|Glu|Lys|Gly|Thr|Lys|Asp|Gln|Ile|Phe|Asn|Asn|Pro|Arg|His|Pro|
| | | | |245| | | |250| | | |255| | | |
|Tyr|Thr|Gln|Ala|Leu|Leu|Ser|Ala|Thr|Pro|Arg|Leu|Asn|Pro|Asp|Asp|
| | | | |260| | | |265| | | |270| | | |
|Arg|Arg|Glu|Arg|Ile|Lys|Leu|Ser|Gly|Glu|Leu|Pro|Ser|Pro|Leu|Asn|
| | | | |275| | | |280| | | |285| | | |
|Pro|Pro|Pro|Gly|Cys|Ala|Phe|Asn|Ala|Arg|Cys|Arg|Arg|Phe|Gly|
| | | |290| | | |295| | | |300| | | |
|Pro|Cys|Thr|Gln|Leu|Gln|Pro|Gln|Leu|Lys|Asp|Tyr|Gly|Gly|Gln|Leu|
|305| | | |310| | | |315| | | | | | |320|
|Val|Ala|Cys|Phe|Ala|Val|Asp|Gln|Asp|Glu|Asn|Pro|Gln|Arg|
| | | | |325| | | |330| | | | | |

```
<210> SEQ ID NO 29
<211> LENGTH: 1509
<212> TYPE: DNA
<213> ORGANISM: Escherichia coli

<400> SEQUENCE: 29
```

| | | | | | | | | | | | | | | | | |
|---|---|---|---|---|---|---|---|---|---|---|---|---|---|---|---|---|
|atg|gag|ttt|agt|gta|aaa|agc|ggt|agc|ccg|gag|aaa|cag|cgg|agt|gcc| 48|
|Met|Glu|Phe|Ser|Val|Lys|Ser|Gly|Ser|Pro|Glu|Lys|Gln|Arg|Ser|Ala| |
|1| | | |5| | | | |10| | | | |15| | |
|tgc|atc|gtc|gtg|ggc|gtc|ttc|gaa|cca|cgt|cgc|ctt|tct|ccg|att|gca| 96|
|Cys|Ile|Val|Val|Gly|Val|Phe|Glu|Pro|Arg|Arg|Leu|Ser|Pro|Ile|Ala| |
| | | |20| | | | |25| | | | |30| | | |
|gaa|cag|ctc|gat|aaa|atc|agc|gat|ggg|tac|atc|agc|gcc|ctg|cta|cgt| 144|
|Glu|Gln|Leu|Asp|Lys|Ile|Ser|Asp|Gly|Tyr|Ile|Ser|Ala|Leu|Leu|Arg| |
| | |35| | | | |40| | | | |45| | | | |
|cgg|ggc|gaa|ctg|gaa|gga|aaa|ccg|ggg|cag|aca|ttg|ttg|ctg|cac|cat| 192|
|Arg|Gly|Glu|Leu|Glu|Gly|Lys|Pro|Gly|Gln|Thr|Leu|Leu|Leu|His|His| |
| |50| | | | |55| | | | |60| | | | | |
|gtt|ccg|aat|gta|ctt|tcc|gag|cga|att|ctc|ctt|att|ggt|tgc|ggc|aaa| 240|
|Val|Pro|Asn|Val|Leu|Ser|Glu|Arg|Ile|Leu|Leu|Ile|Gly|Cys|Gly|Lys| |
|65| | | | |70| | | | |75| | | | |80| |
|gaa|cgt|gag|ctg|gat|gag|cgt|cag|tac|aag|cag|gtt|att|cag|aaa|acc| 288|
|Glu|Arg|Glu|Leu|Asp|Glu|Arg|Gln|Tyr|Lys|Gln|Val|Ile|Gln|Lys|Thr| |
| | | | |85| | | | |90| | | | |95| | |
|att|aat|acg|ctg|aat|gat|act|ggc|tca|atg|gaa|gcg|gtc|tgc|ttt|ctg| 336|
|Ile|Asn|Thr|Leu|Asn|Asp|Thr|Gly|Ser|Met|Glu|Ala|Val|Cys|Phe|Leu| |
| | | |100| | | | |105| | | | |110| | | |
|act|gag|ctg|cac|gtt|aaa|ggc|cgt|aac|aac|tac|tgg|aaa|gtg|cgt|cag| 384|
|Thr|Glu|Leu|His|Val|Lys|Gly|Arg|Asn|Asn|Tyr|Trp|Lys|Val|Arg|Gln| |
| | |115| | | | |120| | | | |125| | | | |
|gct|gtc|gag|acg|gca|aaa|gag|acg|ctc|tac|agt|ttc|gat|cag|ctg|aaa| 432|
|Ala|Val|Glu|Thr|Ala|Lys|Glu|Thr|Leu|Tyr|Ser|Phe|Asp|Gln|Leu|Lys| |
| |130| | | | |135| | | | |140| | | | | |
|acg|aac|aag|agc|gaa|ccg|cgt|cgt|ccg|ctg|cgt|aag|atg|gtg|ttc|aac| 480|
|Thr|Asn|Lys|Ser|Glu|Pro|Arg|Arg|Pro|Leu|Arg|Lys|Met|Val|Phe|Asn| |
|145| | | | |150| | | | |155| | | | |160| |
|gtg|ccg|acc|cgc|cgt|gaa|ctg|acc|agc|ggt|gag|cgc|gcg|atc|cag|cac| 528|
|Val|Pro|Thr|Arg|Arg|Glu|Leu|Thr|Ser|Gly|Glu|Arg|Ala|Ile|Gln|His| |
| | | | |165| | | | |170| | | | |175| | |
|ggt|ctg|gcg|att|gcc|gcc|ggg|att|aaa|gca|gca|aaa|gat|ctc|ggc|aat| 576|
|Gly|Leu|Ala|Ile|Ala|Ala|Gly|Ile|Lys|Ala|Ala|Lys|Asp|Leu|Gly|Asn| |
| | | |180| | | | |185| | | | |190| | | |
|atg|ccg|ccg|aat|atc|tgt|aac|gcc|gct|tac|ctc|gct|tca|caa|gcg|cgc| 624|
|Met|Pro|Pro|Asn|Ile|Cys|Asn|Ala|Ala|Tyr|Leu|Ala|Ser|Gln|Ala|Arg| |
| | |195| | | | |200| | | | |205| | | | |
|cag|ctg|gct|gac|agc|tac|agc|aag|aat|gtc|atc|acc|cgc|gtt|atc|ggc| 672|

```
                Gln Leu Ala Asp Ser Tyr Ser Lys Asn Val Ile Thr Arg Val Ile Gly
                    210                 215                 220 gaa cag cag atg aaa gag ctg ggg atg cat tcc tat ctg gcg gtc ggt         720
Glu Gln Gln Met Lys Glu Leu Gly Met His Ser Tyr Leu Ala Val Gly
225                 230                 235                 240 cag ggt tcg caa aac gaa tcg ctg atg tcg gtg att gag tac aaa ggc         768
Gln Gly Ser Gln Asn Glu Ser Leu Met Ser Val Ile Glu Tyr Lys Gly
                245                 250                 255 aac gcg tcg gaa gat gca cgc cca atc gtg ctg gtg ggt aaa ggt tta         816
Asn Ala Ser Glu Asp Ala Arg Pro Ile Val Leu Val Gly Lys Gly Leu
            260                 265                 270 acc ttc gac tcc ggc ggt atc tcg atc aag cct tca gaa ggc atg gat         864
Thr Phe Asp Ser Gly Gly Ile Ser Ile Lys Pro Ser Glu Gly Met Asp
        275                 280                 285 gag atg aag tac gat atg tgc ggt gcg gca gcg gtt tac ggc gtg atg         912
Glu Met Lys Tyr Asp Met Cys Gly Ala Ala Ala Val Tyr Gly Val Met
    290                 295                 300 cgg atg gtc gcg gag cta caa ctg ccg att aac gtt atc ggc gtg ttg         960
Arg Met Val Ala Glu Leu Gln Leu Pro Ile Asn Val Ile Gly Val Leu
305                 310                 315                 320 gca ggc tgc gaa aac atg cct ggc gga cga gcc tat cgt ccg ggc gat        1008
Ala Gly Cys Glu Asn Met Pro Gly Gly Arg Ala Tyr Arg Pro Gly Asp
                325                 330                 335 gtg tta acc acc atg tcc ggt caa acc gtt gaa gtg ctg aac acc gac        1056
Val Leu Thr Thr Met Ser Gly Gln Thr Val Glu Val Leu Asn Thr Asp
                340                 345                 350 gct gaa ggc cgc ctg gta ctg tgc gac gtg tta act tac gtt gag cgt        1104
Ala Glu Gly Arg Leu Val Leu Cys Asp Val Leu Thr Tyr Val Glu Arg
            355                 360                 365 ttt gag ccg gaa gcg gtg att gac gtg gcg acg ctg acc ggt gcc tgc        1152
Phe Glu Pro Glu Ala Val Ile Asp Val Ala Thr Leu Thr Gly Ala Cys
        370                 375                 380 gtg atc gcg ctg ggt cat cat att act ggt ctg atg gcg aac cat aat        1200
Val Ile Ala Leu Gly His His Ile Thr Gly Leu Met Ala Asn His Asn
385                 390                 395                 400 ccg ctg gcc cat gaa ctg att gcc gcg tct gaa caa tcc ggt gac cgc        1248
Pro Leu Ala His Glu Leu Ile Ala Ala Ser Glu Gln Ser Gly Asp Arg
                405                 410                 415 gca tgg cgc tta ccg ctg ggt gac gag tat cag gaa caa ctg gag tcc        1296
Ala Trp Arg Leu Pro Leu Gly Asp Glu Tyr Gln Glu Gln Leu Glu Ser
                420                 425                 430 aat ttt gcc gat atg gcg aac att ggc ggt cgt cct ggt ggg gcg att        1344
Asn Phe Ala Asp Met Ala Asn Ile Gly Gly Arg Pro Gly Gly Ala Ile
            435                 440                 445 acc gca ggt tgc ttc ctg tca cgc ttt acc cgt aag tac aac tgg gcg        1392
Thr Ala Gly Cys Phe Leu Ser Arg Phe Thr Arg Lys Tyr Asn Trp Ala
        450                 455                 460 cac ctg gat atc gcc ggt acc gcc tgg cgt tct ggt aaa gca aaa ggc        1440
His Leu Asp Ile Ala Gly Thr Ala Trp Arg Ser Gly Lys Ala Lys Gly
465                 470                 475                 480 gcc acc ggt cgt ccg gta gcg ttg ctg gca cag ttc ctg tta aac cgc        1488
Ala Thr Gly Arg Pro Val Ala Leu Leu Ala Gln Phe Leu Leu Asn Arg
                485                 490                 495 gct ggg ttt aac ggc gaa gag                                            1509
Ala Gly Phe Asn Gly Glu Glu
                500

<210> SEQ ID NO 30
<211> LENGTH: 1281
<212> TYPE: DNA
<213> ORGANISM: Escherichia coli
```

```
<400> SEQUENCE: 30 atg aca gaa gcg atg aag att acc ctc tct acc caa cct gcc gac gcg        48
Met Thr Glu Ala Met Lys Ile Thr Leu Ser Thr Gln Pro Ala Asp Ala
 1               5                  10                  15 cgc tgg gga gaa aaa gca act tac agc att aat aat gac ggc att acc        96
Arg Trp Gly Glu Lys Ala Thr Tyr Ser Ile Asn Asn Asp Gly Ile Thr
             20                  25                  30 ctg cat ttg aac ggg gca gac gat ctg ggg ctg atc cag cgt gcg gcg       144
Leu His Leu Asn Gly Ala Asp Asp Leu Gly Leu Ile Gln Arg Ala Ala
         35                  40                  45 cgc aag att gac ggt ctg ggc atc aag cat gtt cag tta agc ggt gaa       192
Arg Lys Ile Asp Gly Leu Gly Ile Lys His Val Gln Leu Ser Gly Glu
     50                  55                  60 ggc tgg gat gcg gat cgc tgc tgg gca ttc tgg caa ggt tac aaa gcc       240
Gly Trp Asp Ala Asp Arg Cys Trp Ala Phe Trp Gln Gly Tyr Lys Ala
 65                  70                  75                  80 ccg aaa ggc acg cgt aaa gtg gtg tgg ccg gat ctg gac gat gcc cag       288
Pro Lys Gly Thr Arg Lys Val Val Trp Pro Asp Leu Asp Asp Ala Gln
                 85                  90                  95 cgc cag gaa ctg gat aac cgc ctg atg atc atc gac tgg gtg cgt gac       336
Arg Gln Glu Leu Asp Asn Arg Leu Met Ile Ile Asp Trp Val Arg Asp
            100                 105                 110 acc atc aac gca ccg gca gaa gaa ttg gga cca tcg caa ctg gca cag       384
Thr Ile Asn Ala Pro Ala Glu Glu Leu Gly Pro Ser Gln Leu Ala Gln
        115                 120                 125 cgt gct gtt gat ctg atc agc aac gtc gcg ggc gat cgt gtg act tat       432
Arg Ala Val Asp Leu Ile Ser Asn Val Ala Gly Asp Arg Val Thr Tyr
    130                 135                 140 cgg atc acc aaa ggc gaa gat ctg cgt gag caa ggt tat atg ggg ctg       480
Arg Ile Thr Lys Gly Glu Asp Leu Arg Glu Gln Gly Tyr Met Gly Leu
145                 150                 155                 160 cac aca gtc gga cgc ggt tca gaa cgt tct ccg gta ttg ctg gcg ctg       528
His Thr Val Gly Arg Gly Ser Glu Arg Ser Pro Val Leu Leu Ala Leu
                165                 170                 175 gat tac aac cca act ggc gat aaa gaa gcg cca gtg tac gcg tgc ctg       576
Asp Tyr Asn Pro Thr Gly Asp Lys Glu Ala Pro Val Tyr Ala Cys Leu
            180                 185                 190 gta ggt aaa ggt atc act ttt gac tcc ggc ggc tac agc atc aaa cag       624
Val Gly Lys Gly Ile Thr Phe Asp Ser Gly Gly Tyr Ser Ile Lys Gln
        195                 200                 205 act gcg ttt atg gac tcg atg aag tcg gac atg ggc ggc gcg gca acg       672
Thr Ala Phe Met Asp Ser Met Lys Ser Asp Met Gly Gly Ala Ala Thr
    210                 215                 220 gtt acc ggg gcg ctg gca ttt gcc att acg cgc gga ctg aac aag cgc       720
Val Thr Gly Ala Leu Ala Phe Ala Ile Thr Arg Gly Leu Asn Lys Arg
225                 230                 235                 240 gtg aag ctg ttc ctc tgc tgt gcg gat aac ctg att agc ggc aat gcg       768
Val Lys Leu Phe Leu Cys Cys Ala Asp Asn Leu Ile Ser Gly Asn Ala
                245                 250                 255 ttc aag ctg ggc gat atc atc acc tat cgc aac ggt aaa aaa gtt gaa       816
Phe Lys Leu Gly Asp Ile Ile Thr Tyr Arg Asn Gly Lys Lys Val Glu
            260                 265                 270 gtg atg aac act gat gcc gaa ggg cgt ctg gtg ctt gcc gat ggt ctg       864
Val Met Asn Thr Asp Ala Glu Gly Arg Leu Val Leu Ala Asp Gly Leu
        275                 280                 285 att gat gcc agt gcg cag aaa ccg gaa atg atc att gat gcg gcg acc       912
Ile Asp Ala Ser Ala Gln Lys Pro Glu Met Ile Ile Asp Ala Ala Thr
    290                 295                 300 ctc acc ggg gcg gcg aaa act gcg ctg ggt aat gat tat cac gcg ctg       960
```

-continued

```
Leu Thr Gly Ala Ala Lys Thr Ala Leu Gly Asn Asp Tyr His Ala Leu
305                 310                 315                 320 ttc agt ttt gac gat gcg ctg gcc ggt cgt ttg ctg gcg agt gcc gcg     1008
Phe Ser Phe Asp Asp Ala Leu Ala Gly Arg Leu Leu Ala Ser Ala Ala
                325                 330                 335 cag gag aac gaa ccg ttc tgg cgt ctg ccg ctg gcg gag ttc cac cgc     1056
Gln Glu Asn Glu Pro Phe Trp Arg Leu Pro Leu Ala Glu Phe His Arg
            340                 345                 350 agc cag ctg ccg tct aac ttt gcc gaa ctg aac aat acc gga agc gcg     1104
Ser Gln Leu Pro Ser Asn Phe Ala Glu Leu Asn Asn Thr Gly Ser Ala
        355                 360                 365 gcg tat ccg gca ggc gcg agc acg gcg gcg ggc ttc ctg tcg cac ttt     1152
Ala Tyr Pro Ala Gly Ala Ser Thr Ala Ala Gly Phe Leu Ser His Phe
    370                 375                 380 gtt gag aac tat cag caa ggc tgg ctg cat atc gac tgc tcg gcg act     1200
Val Glu Asn Tyr Gln Gln Gly Trp Leu His Ile Asp Cys Ser Ala Thr
385                 390                 395                 400 tac cgt aaa gcg ccg gtt gaa cag tgg tct gcg ggc gct acg gga ctt     1248
Tyr Arg Lys Ala Pro Val Glu Gln Trp Ser Ala Gly Ala Thr Gly Leu
                405                 410                 415 ggt gtg cgc acg ata gct aat ctg tta acg gcg                         1281
Gly Val Arg Thr Ile Ala Asn Leu Leu Thr Ala
            420                 425

<210> SEQ ID NO 31
<211> LENGTH: 1455
<212> TYPE: DNA
<213> ORGANISM: Escherichia coli

<400> SEQUENCE: 31 gtg tct gaa ctg tct caa tta tct cca cag ccg ctg tgg gat att ttt      48
Val Ser Glu Leu Ser Gln Leu Ser Pro Gln Pro Leu Trp Asp Ile Phe
  1               5                  10                  15 gcc aaa atc tgt tct att cct cac ccg tcc tat cat gaa gag caa ctc      96
Ala Lys Ile Cys Ser Ile Pro His Pro Ser Tyr His Glu Glu Gln Leu
                 20                  25                  30 gct gaa tac att gtt ggt tgg gca aaa gag aaa ggt ttc cat gtc gaa     144
Ala Glu Tyr Ile Val Gly Trp Ala Lys Glu Lys Gly Phe His Val Glu
             35                  40                  45 cgc gat cag gta ggt aat atc ctg att cgt aaa cct gct acc gca ggt     192
Arg Asp Gln Val Gly Asn Ile Leu Ile Arg Lys Pro Ala Thr Ala Gly
         50                  55                  60 atg gaa aat cgt aaa ccg gtc gtc tta cag gcc cac ctc gat atg gtg     240
Met Glu Asn Arg Lys Pro Val Val Leu Gln Ala His Leu Asp Met Val
 65                  70                  75                  80 ccg cag aaa aat aac gac acc gtg cat gac ttc acg aaa gat cct atc     288
Pro Gln Lys Asn Asn Asp Thr Val His Asp Phe Thr Lys Asp Pro Ile
                 85                  90                  95 cag cct tat att gat ggc gaa tgg gtt aaa gcg cgc ggc acc acg ctg     336
Gln Pro Tyr Ile Asp Gly Glu Trp Val Lys Ala Arg Gly Thr Thr Leu
            100                 105                 110 ggt gcg gat aac ggc att ggt atg gcc tct gcg ctg gcg gtt ctg gct     384
Gly Ala Asp Asn Gly Ile Gly Met Ala Ser Ala Leu Ala Val Leu Ala
        115                 120                 125 gac gaa aac gtg gtt cac ggc ccg ctg gaa gtg ctg ctg acc atg acc     432
Asp Glu Asn Val Val His Gly Pro Leu Glu Val Leu Leu Thr Met Thr
    130                 135                 140 gaa gaa gcc ggt atg gac ggt gcg ttc ggc tta cag ggc aac tgg ttg     480
Glu Glu Ala Gly Met Asp Gly Ala Phe Gly Leu Gln Gly Asn Trp Leu
145                 150                 155                 160 cag gct gat att ctg att aac acc gac tcc gaa gaa gaa ggt gaa atc     528
Gln Ala Asp Ile Leu Ile Asn Thr Asp Ser Glu Glu Glu Gly Glu Ile
```

```
Gln Ala Asp Ile Leu Ile Asn Thr Asp Ser Glu Glu Gly Glu Ile
                165                 170                 175 tac atg ggt tgt gcg ggg ggt atc gac ttc acc tcc aac ctg cat tta       576
Tyr Met Gly Cys Ala Gly Gly Ile Asp Phe Thr Ser Asn Leu His Leu
                180                 185                 190 gat cgt gaa gcg gtt cca gct ggt ttt gaa acc ttc aag tta acc tta       624
Asp Arg Glu Ala Val Pro Ala Gly Phe Glu Thr Phe Lys Leu Thr Leu
                195                 200                 205 aaa ggt ctg aaa ggc ggt cac tcc ggc ggg gaa atc cac gtt ggg ctg       672
Lys Gly Leu Lys Gly Gly His Ser Gly Gly Glu Ile His Val Gly Leu
            210                 215                 220 ggt aat gcc aac aaa ctg ctg gtg cgc ttc ctg gcg ggt cat gcg gaa       720
Gly Asn Ala Asn Lys Leu Leu Val Arg Phe Leu Ala Gly His Ala Glu
225                 230                 235                 240 gaa ctg gat ctg cgc ctt atc gat ttc aac ggc ggc aca ctg cgt aac       768
Glu Leu Asp Leu Arg Leu Ile Asp Phe Asn Gly Gly Thr Leu Arg Asn
                245                 250                 255 gcc atc ccg cgt gaa gcc ttt gcg acc att gct gtc gca gct gat aaa       816
Ala Ile Pro Arg Glu Ala Phe Ala Thr Ile Ala Val Ala Ala Asp Lys
                260                 265                 270 gtc gac gtc ctg aaa tct ctg gtg aat acc tat cag gag atc ctg aaa       864
Val Asp Val Leu Lys Ser Leu Val Asn Thr Tyr Gln Glu Ile Leu Lys
            275                 280                 285 aac gag ctg gca gaa aaa gag aaa aat ctg gcc ttg ttg ctg gac tct       912
Asn Glu Leu Ala Glu Lys Glu Lys Asn Leu Ala Leu Leu Leu Asp Ser
    290                 295                 300 gta gcg aac gat aaa gct gcc ctg att gcg aaa tct cgc gat acc ttt       960
Val Ala Asn Asp Lys Ala Ala Leu Ile Ala Lys Ser Arg Asp Thr Phe
305                 310                 315                 320 att cgt ctg ctg aac gcc acc ccg aac ggt gtg att cgt aac tcc gat      1008
Ile Arg Leu Leu Asn Ala Thr Pro Asn Gly Val Ile Arg Asn Ser Asp
                325                 330                 335 gta gcc aaa ggt gtg gtt gaa acc tcc ctg aac gtc ggt gtg gtg acc      1056
Val Ala Lys Gly Val Val Glu Thr Ser Leu Asn Val Gly Val Val Thr
                340                 345                 350 atg act gac aat aac gta gaa att cac tgc ctg atc cgt tca ctg atc      1104
Met Thr Asp Asn Asn Val Glu Ile His Cys Leu Ile Arg Ser Leu Ile
            355                 360                 365 gac agc ggt aaa gac tac gtg gtg agc atg ctg gat tcg ctg ggt aaa      1152
Asp Ser Gly Lys Asp Tyr Val Val Ser Met Leu Asp Ser Leu Gly Lys
    370                 375                 380 ctg gct ggc gcg aaa acc gaa gcg aaa ggc gca tat cct ggc tgg cag      1200
Leu Ala Gly Ala Lys Thr Glu Ala Lys Gly Ala Tyr Pro Gly Trp Gln
385                 390                 395                 400 ccg gac gct aat tct ccg gtg atg cat ctg gta cgt gaa acc tat cag      1248
Pro Asp Ala Asn Ser Pro Val Met His Leu Val Arg Glu Thr Tyr Gln
                405                 410                 415 cgc ctg ttc aac aag acg ccg aac atc cag att atc cac gcg ggc ctg      1296
Arg Leu Phe Asn Lys Thr Pro Asn Ile Gln Ile Ile His Ala Gly Leu
                420                 425                 430 gaa tgt ggt ctg ttc aaa aaa ccg tat ccg gaa atg gac atg gtt tct      1344
Glu Cys Gly Leu Phe Lys Lys Pro Tyr Pro Glu Met Asp Met Val Ser
            435                 440                 445 atc ggg cca act atc acc ggt cca cac tct ccg gat gag caa gtt cac      1392
Ile Gly Pro Thr Ile Thr Gly Pro His Ser Pro Asp Glu Gln Val His
    450                 455                 460 atc gaa agc gta ggt cat tac tgg aca ctg ctg act gaa ctg ctg aaa      1440
Ile Glu Ser Val Gly His Tyr Trp Thr Leu Leu Thr Glu Leu Leu Lys
465                 470                 475                 480 gaa att ccg gcg aag                                                   1455
Glu Ile Pro Ala Lys
```

```
Glu Ile Pro Ala Lys
              485

<210> SEQ ID NO 32
<211> LENGTH: 2610
<212> TYPE: DNA
<213> ORGANISM: Escherichia coli

<400> SEQUENCE: 32 atg act caa cag cca caa gcc aaa tac cgt cac gat tat cgt gcg ccg     48
Met Thr Gln Gln Pro Gln Ala Lys Tyr Arg His Asp Tyr Arg Ala Pro
 1               5                  10                  15 gat tac cag att act gat att gac ttg acc ttt gac ctc gac gcg caa     96
Asp Tyr Gln Ile Thr Asp Ile Asp Leu Thr Phe Asp Leu Asp Ala Gln
             20                  25                  30 aag acg gtc gtt acc gcg gtc agc cag gct gtc cgt cat ggt gca tca    144
Lys Thr Val Val Thr Ala Val Ser Gln Ala Val Arg His Gly Ala Ser
         35                  40                  45 gat gct ccc ctt cgt ctc aac ggc gaa gac ctc aaa ctg gtt tct gtt    192
Asp Ala Pro Leu Arg Leu Asn Gly Glu Asp Leu Lys Leu Val Ser Val
     50                  55                  60 cat att aat gat gag ccg tgg acc gcc tgg aaa gaa gaa gag ggc gca    240
His Ile Asn Asp Glu Pro Trp Thr Ala Trp Lys Glu Glu Glu Gly Ala
 65                  70                  75                  80 ctg gtt atc agt aat ttg ccg gag cgt ttt acg ctt aag atc att aat    288
Leu Val Ile Ser Asn Leu Pro Glu Arg Phe Thr Leu Lys Ile Ile Asn
                 85                  90                  95 gaa ata agc ccg gcg gcg aat acc gcg ctg gaa ggg ctt tat cag tca    336
Glu Ile Ser Pro Ala Ala Asn Thr Ala Leu Glu Gly Leu Tyr Gln Ser
            100                 105                 110 ggc gat gcg ctt tgc acc cag tgt gaa gcc gaa ggt ttc cgc cat att    384
Gly Asp Ala Leu Cys Thr Gln Cys Glu Ala Glu Gly Phe Arg His Ile
        115                 120                 125 acg tat tat ctc gac cgc ccg gac gtg ctg gcg cgt ttt acc acc aaa    432
Thr Tyr Tyr Leu Asp Arg Pro Asp Val Leu Ala Arg Phe Thr Thr Lys
    130                 135                 140 att att gcc gat aaa atc aaa tat ccc ttc ctg ctt tcc aat ggt aac    480
Ile Ile Ala Asp Lys Ile Lys Tyr Pro Phe Leu Leu Ser Asn Gly Asn
145                 150                 155                 160 cgc gtt gcg caa ggc gaa ctg gaa aac gga cgc cat tgg gta cag tgg    528
Arg Val Ala Gln Gly Glu Leu Glu Asn Gly Arg His Trp Val Gln Trp
                165                 170                 175 cag gac ccg ttc ccg aaa ccg tgc tac ctg ttt gcg ctg gtg gca ggc    576
Gln Asp Pro Phe Pro Lys Pro Cys Tyr Leu Phe Ala Leu Val Ala Gly
            180                 185                 190 gac ttt gat gta ctg cgc gat acc ttt acc acg cgt tct ggt cgc gaa    624
Asp Phe Asp Val Leu Arg Asp Thr Phe Thr Thr Arg Ser Gly Arg Glu
        195                 200                 205 gta gca ctg gag ctg tac gtc gat cgc ggc aac ctt gat cgc gcg ccg    672
Val Ala Leu Glu Leu Tyr Val Asp Arg Gly Asn Leu Asp Arg Ala Pro
    210                 215                 220 tgg gcg atg acc tcg ctg aaa aac tcc atg aaa tgg gat gaa gaa cgc    720
Trp Ala Met Thr Ser Leu Lys Asn Ser Met Lys Trp Asp Glu Glu Arg
225                 230                 235                 240 ttt ggc ctg gag tat gac ctc gac atc tat atg atc gtc gcg gtg gat    768
Phe Gly Leu Glu Tyr Asp Leu Asp Ile Tyr Met Ile Val Ala Val Asp
                245                 250                 255 ttc ttc aat atg ggc gca atg gag aat aag ggg ctg aat atc ttt aac    816
Phe Phe Asn Met Gly Ala Met Glu Asn Lys Gly Leu Asn Ile Phe Asn
            260                 265                 270 tcc aaa tat gtg ctg gcc cgc acc gac acc gcc acc gac aaa gat tac    864
```

```
Ser Lys Tyr Val Leu Ala Arg Thr Asp Thr Ala Thr Asp Lys Asp Tyr
        275                 280                 285 ctc gat att gaa cgc gtt atc ggc cat gaa tat ttc cat aac tgg acc      912
Leu Asp Ile Glu Arg Val Ile Gly His Glu Tyr Phe His Asn Trp Thr
        290                 295                 300 ggt aac cga gtg acc tgt cgc gac tgg ttc cag ctc agc ctg aaa gaa      960
Gly Asn Arg Val Thr Cys Arg Asp Trp Phe Gln Leu Ser Leu Lys Glu
305                 310                 315                 320 ggt tta acc gtc ttc cgc gat cag gag ttc agc tct gac ctt ggt tcc     1008
Gly Leu Thr Val Phe Arg Asp Gln Glu Phe Ser Ser Asp Leu Gly Ser
                325                 330                 335 cgc gca gtt aac cgc atc aat aat gta cgc acc atg cgc gga ttg cag     1056
Arg Ala Val Asn Arg Ile Asn Asn Val Arg Thr Met Arg Gly Leu Gln
                340                 345                 350 ttt gca gaa gac gcc agc ccg atg gcg cac ccg atc cgc ccg gat atg     1104
Phe Ala Glu Asp Ala Ser Pro Met Ala His Pro Ile Arg Pro Asp Met
                355                 360                 365 gtc att gag atg aac aac ttc tac acc ctg acc gtt tac gag aag ggc     1152
Val Ile Glu Met Asn Asn Phe Tyr Thr Leu Thr Val Tyr Glu Lys Gly
370                 375                 380 gcg gaa gtg att cgc atg atc cac acc ctg ctt ggc gaa gaa aac ttc     1200
Ala Glu Val Ile Arg Met Ile His Thr Leu Leu Gly Glu Glu Asn Phe
385                 390                 395                 400 cag aaa ggg atg cag ctt tat ttc gag cgt cat gat ggt agt gca gcg     1248
Gln Lys Gly Met Gln Leu Tyr Phe Glu Arg His Asp Gly Ser Ala Ala
                405                 410                 415 acc tgt gac gac ttt gtg cag gcg atg gaa gat gcg tcg aat gtc gat     1296
Thr Cys Asp Asp Phe Val Gln Ala Met Glu Asp Ala Ser Asn Val Asp
                420                 425                 430 ctc tcc cat ttc cgc cgt tgg tac agc cag tcc ggt aca ccg att gtg     1344
Leu Ser His Phe Arg Arg Trp Tyr Ser Gln Ser Gly Thr Pro Ile Val
                435                 440                 445 acc gtc aaa gac gac tac aat ccg gaa acc gag cag tac acc ctg acc     1392
Thr Val Lys Asp Asp Tyr Asn Pro Glu Thr Glu Gln Tyr Thr Leu Thr
                450                 455                 460 atc agc cag cgc acg cca gcc acg ccg gat cag gca gaa aaa cag ccg     1440
Ile Ser Gln Arg Thr Pro Ala Thr Pro Asp Gln Ala Glu Lys Gln Pro
465                 470                 475                 480 ctg cat att ccg ttt gcc atc gaa ctg tat gat aac gaa ggc aaa gtg     1488
Leu His Ile Pro Phe Ala Ile Glu Leu Tyr Asp Asn Glu Gly Lys Val
                485                 490                 495 atc ccg ttg cag aaa ggc ggt cat ccg gtg aat tcc gtg ctg aac gtc     1536
Ile Pro Leu Gln Lys Gly Gly His Pro Val Asn Ser Val Leu Asn Val
                500                 505                 510 act cag gcg gaa cag acc ttt gtc ttt gat aat gtc tac ttc cag ccg     1584
Thr Gln Ala Glu Gln Thr Phe Val Phe Asp Asn Val Tyr Phe Gln Pro
                515                 520                 525 gtg cct gcg ctg ctg tgc gaa ttc tct gcg cca gtg aaa ctg gaa tat     1632
Val Pro Ala Leu Leu Cys Glu Phe Ser Ala Pro Val Lys Leu Glu Tyr
530                 535                 540 aag tgg agc gat cag caa ctg acc ttc ctg atg cgt cat gcg cgt aat     1680
Lys Trp Ser Asp Gln Gln Leu Thr Phe Leu Met Arg His Ala Arg Asn
545                 550                 555                 560 gat ttc tcc cgc tgg gat gcg gcg caa agt ttg ctg gca acc tac atc     1728
Asp Phe Ser Arg Trp Asp Ala Ala Gln Ser Leu Leu Ala Thr Tyr Ile
                565                 570                 575 aag ctg aac gtc gcg cgt cat cag caa ggt cag ccg ctg tct ctg ccg     1776
Lys Leu Asn Val Ala Arg His Gln Gln Gly Gln Pro Leu Ser Leu Pro
                580                 585                 590 gtg cat gtg gct gat gct ttc cgc gcg gta ctg ctt gat gag aag att     1824
```

|   |   |   |   |   |   |   |   |   |   |   |   |   |   |   |   |
|---|---|---|---|---|---|---|---|---|---|---|---|---|---|---|---|
|   | Val | His | Val | Ala | Asp | Ala | Phe | Arg | Ala | Val | Leu | Leu | Asp | Glu | Lys | Ile |
|   |   | 595 |   |   |   | 600 |   |   |   | 605 |   |   |   |

```
gat cca gcg ctg gcg gca gaa atc ctg acg ctg cct tct gtc aat gaa     1872
Asp Pro Ala Leu Ala Ala Glu Ile Leu Thr Leu Pro Ser Val Asn Glu
610                 615                 620 atg gct gaa ttg ttc gat atc atc gac ccg att gct att gcc gaa gta     1920
Met Ala Glu Leu Phe Asp Ile Ile Asp Pro Ile Ala Ile Ala Glu Val
625                 630                 635                 640 cgc gaa gca ctc act cgt act ctg gcg act gaa ctg gcg gat gag cta     1968
Arg Glu Ala Leu Thr Arg Thr Leu Ala Thr Glu Leu Ala Asp Glu Leu
            645                 650                 655 ctg gct att tac aac gcg aat tac cag agc gag tac cgt gtt gag cat     2016
Leu Ala Ile Tyr Asn Ala Asn Tyr Gln Ser Glu Tyr Arg Val Glu His
        660                 665                 670 gaa gat att gca aaa cgc act ctg cgt aat gcc tgc ctg cgt ttc ctc     2064
Glu Asp Ile Ala Lys Arg Thr Leu Arg Asn Ala Cys Leu Arg Phe Leu
    675                 680                 685 gct ttt ggt gaa acg cat ctg gct gat gtg ctg gtg agc aag cag ttc     2112
Ala Phe Gly Glu Thr His Leu Ala Asp Val Leu Val Ser Lys Gln Phe
690                 695                 700 cac gaa gca aac aat atg act gat gcg ctg gcg gcg ctt tct gcg gcg     2160
His Glu Ala Asn Asn Met Thr Asp Ala Leu Ala Ala Leu Ser Ala Ala
705                 710                 715                 720 gtt gcc gca cag ctg cct tgc cgt gac gcg ctg atg cag gag tac gac     2208
Val Ala Ala Gln Leu Pro Cys Arg Asp Ala Leu Met Gln Glu Tyr Asp
            725                 730                 735 gac aag tgg cat cag aac ggt ctg gtg atg gat aaa tgg ttt atc ctg     2256
Asp Lys Trp His Gln Asn Gly Leu Val Met Asp Lys Trp Phe Ile Leu
        740                 745                 750 caa gcc acc agc ccg gcg gcg aat gtg ctg gag acg gtg cgc ggc ctg     2304
Gln Ala Thr Ser Pro Ala Ala Asn Val Leu Glu Thr Val Arg Gly Leu
    755                 760                 765 ttg cag cat cgc tca ttt acc atg agc aac ccg aac cgt att cgt tcg     2352
Leu Gln His Arg Ser Phe Thr Met Ser Asn Pro Asn Arg Ile Arg Ser
770                 775                 780 ttg att ggc gcg ttt gcg ggc agc aat ccg gca gcg ttc cat gcc gaa     2400
Leu Ile Gly Ala Phe Ala Gly Ser Asn Pro Ala Ala Phe His Ala Glu
785                 790                 795                 800 gat ggc agc ggt tac ctg ttc ctg gtg gaa atg ctt acc gac ctc aac     2448
Asp Gly Ser Gly Tyr Leu Phe Leu Val Glu Met Leu Thr Asp Leu Asn
            805                 810                 815 agc cgt aac ccg cag gtg gct tca cgt ctg att gaa ccg ctg att cgc     2496
Ser Arg Asn Pro Gln Val Ala Ser Arg Leu Ile Glu Pro Leu Ile Arg
        820                 825                 830 ctg aaa cgt tac gat gcc aaa cgt cag gag aaa atg cgc gcg gcg ctg     2544
Leu Lys Arg Tyr Asp Ala Lys Arg Gln Glu Lys Met Arg Ala Ala Leu
    835                 840                 845 gaa cag ttg aaa ggg ctg gaa aat ctc tct ggc gat ctg tac gag aag     2592
Glu Gln Leu Lys Gly Leu Glu Asn Leu Ser Gly Asp Leu Tyr Glu Lys
850                 855                 860 ata act aaa gca ctg gct                                             2610
Ile Thr Lys Ala Leu Ala
865                 870

<210> SEQ ID NO 33
<211> LENGTH: 1605
<212> TYPE: DNA
<213> ORGANISM: Escherichia coli

<400> SEQUENCE: 33 atg cgt att tcc ttg aaa aag tca ggg atg ctg aag ctt ggt ctc agc       48
```

```
                                                     -continued

Met Arg Ile Ser Leu Lys Lys Ser Gly Met Leu Lys Leu Gly Leu Ser
 1               5                  10                  15 ctg gtg gct atg acc gtc gca gca agt gtt cag gct aaa act ctg gtt      96
Leu Val Ala Met Thr Val Ala Ala Ser Val Gln Ala Lys Thr Leu Val
             20                  25                  30 tat tgc tca gaa gga tct ccg gaa ggg ttt aac ccg cag ctg ttt acc     144
Tyr Cys Ser Glu Gly Ser Pro Glu Gly Phe Asn Pro Gln Leu Phe Thr
         35                  40                  45 tcc ggc acc acc tat gac gcc tct tcc gtc ccg ctt tat aac cgt ctg     192
Ser Gly Thr Thr Tyr Asp Ala Ser Ser Val Pro Leu Tyr Asn Arg Leu
     50                  55                  60 gtt gaa ttt aaa atc ggc acc acc gaa gtg atc ccg ggc ctc gct gaa     240
Val Glu Phe Lys Ile Gly Thr Thr Glu Val Ile Pro Gly Leu Ala Glu
 65                  70                  75                  80 aag tgg gaa gtc agc gaa gac ggt aaa acc tat acc ttc cat ctg cgt     288
Lys Trp Glu Val Ser Glu Asp Gly Lys Thr Tyr Thr Phe His Leu Arg
                 85                  90                  95 aaa ggt gtg aag tgg cac gac aat aaa gaa ttc aaa ccg acg cgt gaa     336
Lys Gly Val Lys Trp His Asp Asn Lys Glu Phe Lys Pro Thr Arg Glu
            100                 105                 110 ctg aac gcc gat gat gtg gtg ttc tcg ttc gat cgt cag aaa aac gcg     384
Leu Asn Ala Asp Asp Val Val Phe Ser Phe Asp Arg Gln Lys Asn Ala
        115                 120                 125 caa aac ccg tac cat aaa gtt tct ggc ggc agc tac gaa tac ttc gaa     432
Gln Asn Pro Tyr His Lys Val Ser Gly Gly Ser Tyr Glu Tyr Phe Glu
    130                 135                 140 ggc atg ggc ttg cca gag ctg atc agt gaa gtg aaa aag gtg gac gac     480
Gly Met Gly Leu Pro Glu Leu Ile Ser Glu Val Lys Lys Val Asp Asp
145                 150                 155                 160 aac acc gtt cag ttt gtg ctg act cgc ccg gaa gcg ccg ttc ctc gct     528
Asn Thr Val Gln Phe Val Leu Thr Arg Pro Glu Ala Pro Phe Leu Ala
                165                 170                 175 gac ctg gca atg gac ttc gcc tct att ctg tca aaa gaa tat gct gat     576
Asp Leu Ala Met Asp Phe Ala Ser Ile Leu Ser Lys Glu Tyr Ala Asp
            180                 185                 190 gcg atg atg aaa gcc ggt aca ccg gaa aaa ctg gac ctc aac cca atc     624
Ala Met Met Lys Ala Gly Thr Pro Glu Lys Leu Asp Leu Asn Pro Ile
        195                 200                 205 gga acc ggt ccg ttc cag tta cag cag tat caa aaa gat tcc cgt atc     672
Gly Thr Gly Pro Phe Gln Leu Gln Gln Tyr Gln Lys Asp Ser Arg Ile
    210                 215                 220 cgc tac aaa gcg ttt gat ggc tac tgg ggc acc aaa ccg cag atc gat     720
Arg Tyr Lys Ala Phe Asp Gly Tyr Trp Gly Thr Lys Pro Gln Ile Asp
225                 230                 235                 240 acg ctg gtt ttc tct att acc cct gac gct tcc gtg cgt tac gcg aaa     768
Thr Leu Val Phe Ser Ile Thr Pro Asp Ala Ser Val Arg Tyr Ala Lys
                245                 250                 255 ttg cag aag aat gaa tgc cag gtg atg ccg tac ccg aac ccg gca gat     816
Leu Gln Lys Asn Glu Cys Gln Val Met Pro Tyr Pro Asn Pro Ala Asp
            260                 265                 270 atc gct cgc atg aag cag gat aaa tcc atc aat ctg atg gaa atg ccg     864
Ile Ala Arg Met Lys Gln Asp Lys Ser Ile Asn Leu Met Glu Met Pro
        275                 280                 285 ggg ctg aac gtc ggt tat ctc tcg tat aac gtg cag aaa aaa cca ctc     912
Gly Leu Asn Val Gly Tyr Leu Ser Tyr Asn Val Gln Lys Lys Pro Leu
    290                 295                 300 gat gac gtg aaa gtt cgc cag gct ctg acc tac gcg gtg aac aaa gac     960
Asp Asp Val Lys Val Arg Gln Ala Leu Thr Tyr Ala Val Asn Lys Asp
305                 310                 315                 320 gcg atc atc aaa gcg gtt tat cag ggc gcg ggc gta tca gcg aaa aac    1008
```

```
Ala Ile Ile Lys Ala Val Tyr Gln Gly Ala Gly Val Ser Ala Lys Asn
            325                 330                 335 ctg atc ccg cca acc atg tgg ggc tat aac gac gac gtt cag gac tac    1056
Leu Ile Pro Pro Thr Met Trp Gly Tyr Asn Asp Asp Val Gln Asp Tyr
            340                 345                 350 acc tac gat cct gaa aaa gcg aaa gcc ttg ctg aaa gaa gcg ggt ctg    1104
Thr Tyr Asp Pro Glu Lys Ala Lys Ala Leu Leu Lys Glu Ala Gly Leu
            355                 360                 365 gaa aaa ggt ttc tcc atc gac ctg tgg gcg atg ccg gta caa cgt ccg    1152
Glu Lys Gly Phe Ser Ile Asp Leu Trp Ala Met Pro Val Gln Arg Pro
        370                 375                 380 tat aac ccg aac gct cgc cgc atg gcg gag atg att cag gca gac tgg    1200
Tyr Asn Pro Asn Ala Arg Arg Met Ala Glu Met Ile Gln Ala Asp Trp
385                 390                 395                 400 gcg aaa gtc ggc gtg cag gcc aaa att gtc acc tac gaa tgg ggt gag    1248
Ala Lys Val Gly Val Gln Ala Lys Ile Val Thr Tyr Glu Trp Gly Glu
                405                 410                 415 tac ctc aag cgt gcg aaa gat ggc gag cac cag acg gta atg atg ggc    1296
Tyr Leu Lys Arg Ala Lys Asp Gly Glu His Gln Thr Val Met Met Gly
            420                 425                 430 tgg act ggc gat aac ggg gat ccg gat aac ttc ttc gcc acc ctg ttc    1344
Trp Thr Gly Asp Asn Gly Asp Pro Asp Asn Phe Phe Ala Thr Leu Phe
            435                 440                 445 agc tgc gcc gcc tct gaa caa ggc tcc aac tac tca aaa tgg tgc tac    1392
Ser Cys Ala Ala Ser Glu Gln Gly Ser Asn Tyr Ser Lys Trp Cys Tyr
        450                 455                 460 aaa ccg ttt gaa gat ctg att caa ccg gcg cgt gct acc gac gac cac    1440
Lys Pro Phe Glu Asp Leu Ile Gln Pro Ala Arg Ala Thr Asp Asp His
465                 470                 475                 480 aat aaa cgc gtt gaa ctg tac aaa caa gcg cag gtg gtg atg cac gat    1488
Asn Lys Arg Val Glu Leu Tyr Lys Gln Ala Gln Val Val Met His Asp
                485                 490                 495 cag gct ccg gca ctg atc atc gct cac tcc acc gtg ttt gaa ccg gta    1536
Gln Ala Pro Ala Leu Ile Ile Ala His Ser Thr Val Phe Glu Pro Val
            500                 505                 510 cgt aaa gaa gtt aaa ggc tat gtg gtt gat cca tta ggc aaa cat cac    1584
Arg Lys Glu Val Lys Gly Tyr Val Val Asp Pro Leu Gly Lys His His
            515                 520                 525 ttc gaa aac gtc tct atc gaa                                        1605
Phe Glu Asn Val Ser Ile Glu
        530                 535

<210> SEQ ID NO 34
<211> LENGTH: 1017
<212> TYPE: DNA
<213> ORGANISM: Escherichia coli

<400> SEQUENCE: 34 atg ttg cag ttt att ctc cga cgt ttg gga ctc gtc atc ccc acg ttt      48
Met Leu Gln Phe Ile Leu Arg Arg Leu Gly Leu Val Ile Pro Thr Phe
  1               5                  10                  15 atc ggt att acc ctt ctc aca ttt gcc ttt gtc cac atg atc ccg ggc      96
Ile Gly Ile Thr Leu Leu Thr Phe Ala Phe Val His Met Ile Pro Gly
                20                  25                  30 gat ccg gtg atg atc atg gcg ggc gaa cgt ggg atc tcc cca gag cgt     144
Asp Pro Val Met Ile Met Ala Gly Glu Arg Gly Ile Ser Pro Glu Arg
            35                  40                  45 cac gcg cag ctg ctg gct gaa ctc ggc tta gat aaa ccg atg tgg cag     192
His Ala Gln Leu Leu Ala Glu Leu Gly Leu Asp Lys Pro Met Trp Gln
        50                  55                  60 cag tat ctc cat tac att tgg ggc gtt atg cat ggc gat cta ggc att     240
```

|  |  |  |  |  |  |  |  |  |  |  |  |  |  |  |  |
|---|---|---|---|---|---|---|---|---|---|---|---|---|---|---|---|
| Gln | Tyr | Leu | His | Tyr | Ile | Trp | Gly | Val | Met | His | Gly | Asp | Leu | Gly | Ile |
| 65 |  |  |  | 70 |  |  |  | 75 |  |  |  | 80 |  |  |  |

```
tca atg aaa agc cgc atc ccg gtt tgg gaa gag ttc gtg ccg cgc ttc      288
Ser Met Lys Ser Arg Ile Pro Val Trp Glu Glu Phe Val Pro Arg Phe
            85                  90                  95 cag gcc acg ctg gaa ctt ggc gtc tgc gcg atg att ttt gct acg gca      336
Gln Ala Thr Leu Glu Leu Gly Val Cys Ala Met Ile Phe Ala Thr Ala
       100                 105                 110 gtc ggt att ccg gtc ggc gtg ctg gct gcg gtt aaa cgc ggt tcc att      384
Val Gly Ile Pro Val Gly Val Leu Ala Ala Val Lys Arg Gly Ser Ile
           115                 120                 125 ttc gat cac aca gcg gtt ggc ctg gcg ctg aca ggt tat tca atg cct      432
Phe Asp His Thr Ala Val Gly Leu Ala Leu Thr Gly Tyr Ser Met Pro
130                 135                 140 atc ttc tgg tgg ggc atg atg ctg atc atg ctg gtt tcg gtg cac tgg      480
Ile Phe Trp Trp Gly Met Met Leu Ile Met Leu Val Ser Val His Trp
145                 150                 155                 160 aac ctg acg ccc gtc tcc ggt cgc gtg agc gat atg gtg ttc ctc gat      528
Asn Leu Thr Pro Val Ser Gly Arg Val Ser Asp Met Val Phe Leu Asp
                165                 170                 175 gac tcc aat ccg tta acc ggt ttt atg cta atc gac acc gcc atc tgg      576
Asp Ser Asn Pro Leu Thr Gly Phe Met Leu Ile Asp Thr Ala Ile Trp
            180                 185                 190 ggt gaa gac ggc aac ttt atc gat gcc gtc gcc cat atg atc ttg cct      624
Gly Glu Asp Gly Asn Phe Ile Asp Ala Val Ala His Met Ile Leu Pro
        195                 200                 205 gcc att gtg ctg ggt act att ccg ctg gcg gtc att gtg cgt atg aca      672
Ala Ile Val Leu Gly Thr Ile Pro Leu Ala Val Ile Val Arg Met Thr
   210                 215                 220 cgc tcc tcg atg ctg gaa gtg ctg ggc gag gat tac atc cgc acc gcg      720
Arg Ser Ser Met Leu Glu Val Leu Gly Glu Asp Tyr Ile Arg Thr Ala
225                 230                 235                 240 cgc gcc aaa ggg cta acc cgc atg cgg gtg att atc gtc cat gcg ctg      768
Arg Ala Lys Gly Leu Thr Arg Met Arg Val Ile Ile Val His Ala Leu
                245                 250                 255 cgt aac gcg atg ctg ccg gtg gtg acc gtt atc ggc ctg cag gtg gga      816
Arg Asn Ala Met Leu Pro Val Val Thr Val Ile Gly Leu Gln Val Gly
            260                 265                 270 aca ttg ctg gcg ggg gcg att ctg acc gaa acc atc ttc tcg tgg ccc      864
Thr Leu Leu Ala Gly Ala Ile Leu Thr Glu Thr Ile Phe Ser Trp Pro
        275                 280                 285 ggt ctg gga cgc tgg ttg att gac gca ctg caa cgc cgc gac tat ccg      912
Gly Leu Gly Arg Trp Leu Ile Asp Ala Leu Gln Arg Arg Asp Tyr Pro
    290                 295                 300 gta gtg cag ggc ggc gta ttg ctg gtg gcg acg atg att atc ctc gtc      960
Val Val Gln Gly Gly Val Leu Leu Val Ala Thr Met Ile Ile Leu Val
305                 310                 315                 320 aac ttg ctg gtc gat ctg ctg tac ggc gtg gtg aac ccg cgt att cgt     1008
Asn Leu Leu Val Asp Leu Leu Tyr Gly Val Val Asn Pro Arg Ile Arg
                325                 330                 335 cat aag aag                                                         1017
His Lys Lys <210> SEQ ID NO 35
<211> LENGTH: 900
<212> TYPE: DNA
<213> ORGANISM: Escherichia coli

<400> SEQUENCE: 35 atg tca cag gtt act gaa aat aaa gtg att agc gca ccg gtg ccg atg       48
Met Ser Gln Val Thr Glu Asn Lys Val Ile Ser Ala Pro Val Pro Met
```

```
                1               5              10               15
acc ccg tta cag gag ttc tgg cac tat ttt aaa cgc aac aaa ggc gcg       96
Thr Pro Leu Gln Glu Phe Trp His Tyr Phe Lys Arg Asn Lys Gly Ala
             20                  25                  30 gtc gtc ggg ctg gtt tac gtc gtc atc gtg ctg ttc atc gcg atc ttt      144
Val Val Gly Leu Val Tyr Val Val Ile Val Leu Phe Ile Ala Ile Phe
         35                  40                  45 gcc aac tgg att gca ccc tat aac ccg gcg gaa cag ttc cgc gat gca      192
Ala Asn Trp Ile Ala Pro Tyr Asn Pro Ala Glu Gln Phe Arg Asp Ala
 50                  55                  60 ctg ctc gcc ccg cca gcc tgg cag gaa ggc ggc agc atg gcg cac ttg      240
Leu Leu Ala Pro Pro Ala Trp Gln Glu Gly Gly Ser Met Ala His Leu
 65                  70                  75                  80 ctg ggc acc gat gac gta ggc cgt gat gtg ctg tcg cgc ctg atg tac      288
Leu Gly Thr Asp Asp Val Gly Arg Asp Val Leu Ser Arg Leu Met Tyr
             85                  90                  95 ggt gcg cgc ctg tcg ctg ctg gtt ggc tgt ctg gta gtt gtg tta tcg      336
Gly Ala Arg Leu Ser Leu Leu Val Gly Cys Leu Val Val Val Leu Ser
        100                 105                 110 ctg att atg ggc gtt att ctc ggc ctg atc gcc ggt tac ttt ggc ggc      384
Leu Ile Met Gly Val Ile Leu Gly Leu Ile Ala Gly Tyr Phe Gly Gly
        115                 120                 125 ctg gtc gat aac atc att atg cgc gtg gtc gat atc atg ctg gcg ctg      432
Leu Val Asp Asn Ile Ile Met Arg Val Val Asp Ile Met Leu Ala Leu
    130                 135                 140 cca agt ctg ctg ctg gcg ctg gtg ctg gtg gca att ttc ggc ccg tcg      480
Pro Ser Leu Leu Leu Ala Leu Val Leu Val Ala Ile Phe Gly Pro Ser
145                 150                 155                 160 att ggt aac gcc gcg ctg gca ctg acc ttc gtt gcc ttg ccg cac tat      528
Ile Gly Asn Ala Ala Leu Ala Leu Thr Phe Val Ala Leu Pro His Tyr
                165                 170                 175 gtg cgc tta acc cgc gcc gcc gtg ctg gtg gaa gtt aac cgc gat tac      576
Val Arg Leu Thr Arg Ala Ala Val Leu Val Glu Val Asn Arg Asp Tyr
            180                 185                 190 gtc acc gcg tct cgc gtg gcg ggt gcc ggg gcg atg cgt cag atg ttt      624
Val Thr Ala Ser Arg Val Ala Gly Ala Gly Ala Met Arg Gln Met Phe
        195                 200                 205 att aac atc ttc ccg aac tgc ctt gcg ccg ctg att gtt cag gcg tcg      672
Ile Asn Ile Phe Pro Asn Cys Leu Ala Pro Leu Ile Val Gln Ala Ser
    210                 215                 220 ctc ggt ttc tct aac gcc att ctc gat atg gct gct ctt ggt ttc ctc      720
Leu Gly Phe Ser Asn Ala Ile Leu Asp Met Ala Ala Leu Gly Phe Leu
225                 230                 235                 240 ggc atg ggg gca cag ccg cca acg cct gag tgg ggc acc atg ctc tcc      768
Gly Met Gly Ala Gln Pro Pro Thr Pro Glu Trp Gly Thr Met Leu Ser
                245                 250                 255 gac gtg ttg cag ttc gcg caa agc gcc tgg tgg gtc gtg acc ttc ccg      816
Asp Val Leu Gln Phe Ala Gln Ser Ala Trp Trp Val Val Thr Phe Pro
            260                 265                 270 ggt ctg gcg atc ctg ctg acg gtg ctg gca ttt aac ctg atg ggt gac      864
Gly Leu Ala Ile Leu Leu Thr Val Leu Ala Phe Asn Leu Met Gly Asp
        275                 280                 285 ggt ctg cgt gac gcg ctc gat ccc aaa ctg aag cag                      900
Gly Leu Arg Asp Ala Leu Asp Pro Lys Leu Lys Gln
    290                 295                 300

<210> SEQ ID NO 36
<211> LENGTH: 981
<212> TYPE: DNA
<213> ORGANISM: Escherichia coli
```

<400> SEQUENCE: 36

```
atg gcg tta tta aat gta gat aaa tta tcg gtg cat ttc ggc gac gaa      48
Met Ala Leu Leu Asn Val Asp Lys Leu Ser Val His Phe Gly Asp Glu
 1               5                  10                  15 agc gcg ccg ttc cgc gcc gta gac cgc atc agc tac agc gta aaa cag      96
Ser Ala Pro Phe Arg Ala Val Asp Arg Ile Ser Tyr Ser Val Lys Gln
            20                  25                  30 ggc gaa gtg gtc ggg att gtg ggt gag tcc ggc tcc ggt aag tcg gtc     144
Gly Glu Val Val Gly Ile Val Gly Glu Ser Gly Ser Gly Lys Ser Val
        35                  40                  45 agt tca ctg gcg att atg ggg ctg att gat tat ccg ggc cgc gta atg     192
Ser Ser Leu Ala Ile Met Gly Leu Ile Asp Tyr Pro Gly Arg Val Met
 50                  55                  60 gca gaa aaa ctg gag ttt aac ggc cag gat ttg cag cgt atc tca gaa     240
Ala Glu Lys Leu Glu Phe Asn Gly Gln Asp Leu Gln Arg Ile Ser Glu
 65                  70                  75                  80 aaa gag cgc cgc aac ctg gtg ggt gcc gaa gtg gcg atg atc ttc cag     288
Lys Glu Arg Arg Asn Leu Val Gly Ala Glu Val Ala Met Ile Phe Gln
                85                  90                  95 gac ccg atg acc agc ctt aac ccg tgc tac acc gtg ggt ttc cag att     336
Asp Pro Met Thr Ser Leu Asn Pro Cys Tyr Thr Val Gly Phe Gln Ile
            100                 105                 110 atg gaa gcg att aag gtg cat cag ggc ggc aac aaa agt acc cgc cgt     384
Met Glu Ala Ile Lys Val His Gln Gly Gly Asn Lys Ser Thr Arg Arg
        115                 120                 125 cag cga gcg att gac ctg ctg aat cag gtc ggt att ccc gat ccg gca     432
Gln Arg Ala Ile Asp Leu Leu Asn Gln Val Gly Ile Pro Asp Pro Ala
130                 135                 140 tcg cgt ctg gat gtt tac ccg cat cag ctt tcc ggc ggc atg agc cag     480
Ser Arg Leu Asp Val Tyr Pro His Gln Leu Ser Gly Gly Met Ser Gln
145                 150                 155                 160 cgc gtg atg atc gcc atg gcg att gcc tgt cgg cca aaa ctg ctg att     528
Arg Val Met Ile Ala Met Ala Ile Ala Cys Arg Pro Lys Leu Leu Ile
                165                 170                 175 gcc gat gaa ccg acc acc gcg ctg gac gtg acc att cag gcg caa atc     576
Ala Asp Glu Pro Thr Thr Ala Leu Asp Val Thr Ile Gln Ala Gln Ile
            180                 185                 190 atc gaa cta ctg ctg gag cta cag cag aaa gag aac atg gcg ctg gtg     624
Ile Glu Leu Leu Leu Glu Leu Gln Gln Lys Glu Asn Met Ala Leu Val
        195                 200                 205 tta att acc cat gac ctg gcg ctg gtg gcg gaa gcg gca cat aaa atc     672
Leu Ile Thr His Asp Leu Ala Leu Val Ala Glu Ala Ala His Lys Ile
210                 215                 220 atc gtg atg tat gca ggc cag gtg gtg gaa acc ggt gat gcg cac gcc     720
Ile Val Met Tyr Ala Gly Gln Val Val Glu Thr Gly Asp Ala His Ala
225                 230                 235                 240 atc ttc cat gcg ccg cgt cac ccg tat act cag gca ttg ctg cgt gcg     768
Ile Phe His Ala Pro Arg His Pro Tyr Thr Gln Ala Leu Leu Arg Ala
                245                 250                 255 ctg cca gaa ttt gct cag gac aaa gaa cgt ctg gcg tcg ttg cca ggt     816
Leu Pro Glu Phe Ala Gln Asp Lys Glu Arg Leu Ala Ser Leu Pro Gly
            260                 265                 270 gtc gtt ccc ggc aag tac gac cgc ccg aac ggc tgc ctg ctt aac ccg     864
Val Val Pro Gly Lys Tyr Asp Arg Pro Asn Gly Cys Leu Leu Asn Pro
        275                 280                 285 cgc tgc ccc tat gcc act gac aga tgt cgc gct gaa gaa ccg gcg ctg     912
Arg Cys Pro Tyr Ala Thr Asp Arg Cys Arg Ala Glu Glu Pro Ala Leu
290                 295                 300 aat atg ctc gct gac ggg cgt cag tcc aaa tgc cat tac cca ctt gat     960
Asn Met Leu Ala Asp Gly Arg Gln Ser Lys Cys His Tyr Pro Leu Asp
```

```
                  305                 310                 315                 320
gat gcc ggg agg ccg aca cta                                                             981
Asp Ala Gly Arg Pro Thr Leu
                325

<210> SEQ ID NO 37
<211> LENGTH: 1002
<212> TYPE: DNA
<213> ORGANISM: Escherichia coli

<400> SEQUENCE: 37 atg agt acg caa gag gcc acc ctg caa caa ccg ctg ttg cag gct atc           48
Met Ser Thr Gln Glu Ala Thr Leu Gln Gln Pro Leu Leu Gln Ala Ile
 1               5                  10                  15 gac ctg aaa aaa cat tat ccg gtg aag aaa ggc atg ttc gcg ccg gaa           96
Asp Leu Lys Lys His Tyr Pro Val Lys Lys Gly Met Phe Ala Pro Glu
                20                  25                  30 cgt ctg gtt aaa gcg ctg gat ggc gtt tcg ttt aac ctt gaa cgt ggc          144
Arg Leu Val Lys Ala Leu Asp Gly Val Ser Phe Asn Leu Glu Arg Gly
            35                  40                  45 aaa acg ctg gca gta gtg ggc gaa tct ggc tgc ggt aaa tcg acc ctc          192
Lys Thr Leu Ala Val Val Gly Glu Ser Gly Cys Gly Lys Ser Thr Leu
        50                  55                  60 ggt cgg ttg ctg acg atg att gaa atg ccc acc ggt ggc gag ctg tat          240
Gly Arg Leu Leu Thr Met Ile Glu Met Pro Thr Gly Gly Glu Leu Tyr
    65                  70                  75                  80 tac cag ggg cag gat ctg ctt aag cac gat ccg cag gcg cag aag ctg          288
Tyr Gln Gly Gln Asp Leu Leu Lys His Asp Pro Gln Ala Gln Lys Leu
                85                  90                  95 cgt cgg cag aaa atc cag atc gtc ttc cag aac cct tac ggt tcg ctg          336
Arg Arg Gln Lys Ile Gln Ile Val Phe Gln Asn Pro Tyr Gly Ser Leu
            100                 105                 110 aat ccg cgt aaa aaa gtc ggg caa att ctt gaa gag ccg ctg ctg atc          384
Asn Pro Arg Lys Lys Val Gly Gln Ile Leu Glu Glu Pro Leu Leu Ile
        115                 120                 125 aac acc agc tta agc aaa gaa cag cgt cgg gaa aaa gcc ctg tcg atg          432
Asn Thr Ser Leu Ser Lys Glu Gln Arg Arg Glu Lys Ala Leu Ser Met
    130                 135                 140 atg gcg aaa gtc ggc ctg aaa acc gag cac tat gac cgc tat ccg cat          480
Met Ala Lys Val Gly Leu Lys Thr Glu His Tyr Asp Arg Tyr Pro His
145                 150                 155                 160 atg ttc tcc ggc ggt cag cgt cag cgt atc gcc atc gcc cgt ggt ctg          528
Met Phe Ser Gly Gly Gln Arg Gln Arg Ile Ala Ile Ala Arg Gly Leu
                165                 170                 175 atg ctc gac ccg gat gtg gtg att gcc gat gaa ccg gtt tcc gcg ctg          576
Met Leu Asp Pro Asp Val Val Ile Ala Asp Glu Pro Val Ser Ala Leu
            180                 185                 190 gat gtt tca gtg cgc gcg cag gtg ctg aat ctg atg atg gat ttg cag          624
Asp Val Ser Val Arg Ala Gln Val Leu Asn Leu Met Met Asp Leu Gln
        195                 200                 205 cag gag ttg ggg ctg tct tat gtc ttt atc tcc cac gac ctg tcg gtg          672
Gln Glu Leu Gly Leu Ser Tyr Val Phe Ile Ser His Asp Leu Ser Val
    210                 215                 220 gtg gag cac att gct gat gaa gtg atg gtg atg tac ctg ggc cgc tgc          720
Val Glu His Ile Ala Asp Glu Val Met Val Met Tyr Leu Gly Arg Cys
225                 230                 235                 240 gtg gag aag gga acg aaa gac caa atc ttc aat aac ccg cgc cat ccg          768
Val Glu Lys Gly Thr Lys Asp Gln Ile Phe Asn Asn Pro Arg His Pro
                245                 250                 255 tac act cag gcg cta ctt tcc gcg acg ccg cgc ctg aac ccg gac gat          816
Tyr Thr Gln Ala Leu Leu Ser Ala Thr Pro Arg Leu Asn Pro Asp Asp
```

-continued

```
                            260                 265                 270
cgc cgc gag cgc atc aag ctc agc ggt gaa cta cca agc cca ctg aat        864
Arg Arg Glu Arg Ile Lys Leu Ser Gly Glu Leu Pro Ser Pro Leu Asn
            275                 280                 285 cca ccg ccg ggt tgc gcc ttc aac gcc cgc tgt cgt cgg cgc ttc ggc        912
Pro Pro Pro Gly Cys Ala Phe Asn Ala Arg Cys Arg Arg Arg Phe Gly
        290                 295                 300 ccc tgc acc cag ttg cag ccg cag cta aaa gac tac ggc ggt caa ctg        960
Pro Cys Thr Gln Leu Gln Pro Gln Leu Lys Asp Tyr Gly Gly Gln Leu
305                 310                 315                 320 gta gct tgt ttt gct gtt gat cag gat gaa aat ccg cag cgt               1002
Val Ala Cys Phe Ala Val Asp Gln Asp Glu Asn Pro Gln Arg
                325                 330
```

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
gaagttccta tactttctag agaataggaa cttc                                   34

<210> SEQ ID NO 39
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
ctaaccctgt gacctgcaat actgttttgc gggtgagtgt aggctggagc tgcttc           56

<210> SEQ ID NO 40
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
gaaactgccg gaaggcgatt aaacgccatc cggcagcata tgaatatcct ccttag           56

<210> SEQ ID NO 41
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
ttacgcaaca ggaatagact gaacaccaga ctctatgtgt aggctggagc tgcttc           56

<210> SEQ ID NO 42
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
agaaaacagg ggtaaattcc ccgaatggcg gcgctacata tgaatatcct ccttag         56

<210> SEQ ID NO 43
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
atggagttta gtgtaaaaag cggtagcccg gagaaagtgt aggctggagc tgcttc         56

<210> SEQ ID NO 44
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
ttactcttcg ccgttaaacc cagcgcggtt taacagcata tgaatatcct ccttag         56

<210> SEQ ID NO 45
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
atgacagaag cgatgaagat taccctctct acccaagtgt aggctggagc tgcttc         56

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
ttacgccgtt aacagattag ctatcgtgcg cacacccata tgaatatcct ccttag         56

<210> SEQ ID NO 47
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
gcatccccac ctcataacgt tgacccgacc gggcaagtgt aggctggagc tgcttc         56

<210> SEQ ID NO 48
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 48
ctgtacggca ttttgctatg cttgtcgcca ctgttgcata tgaatatcct ccttag         56

```
<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 49
gtgtctgaac tgtctcaatt a                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 50
cggaatttct ttcagcagtt c                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 51
atgactcaac agccacaagc c                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 52
tgctttagtt atcttctcgt a                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 53
agtgcctgca tcgtcgtggg c                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 54
ggcgcctttt gctttaccag a                                              21
```

```
<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 55
gacgcgcgct ggggagaaaa a                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 56
cgtagcgccc gcagaccact g                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 57
atgcgtattt ccttgaaaaa g                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 58
ttattcgata gagacgtttt c                                              21

<210> SEQ ID NO 59
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59
gttgagcggc tgccagagcc tttagccgag gaatcagtgt aggctggagc tgcttc        56

<210> SEQ ID NO 60
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 60
ctgccagctt gcccgcacca gttcacgctc tgcggtcata tgaatatcct ccttag        56

<210> SEQ ID NO 61
<211> LENGTH: 56
```

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
ctggacgatg tccgcgaagc actggccgaa gtcggtgtgt aggctggagc tgcttc         56

<210> SEQ ID NO 62
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
tgccgcgtcg tcctcttcac cggtacggat gcgaatcata tgaatatcct ccttag         56

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 63
agccaaccgc cgcaggccga cgaatgg                                         27

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 64
ggtcagcgcc atcgcttcct gctcttc                                         27

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 65
tcccgacacg agctggatgc aaacgat                                         27

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
atggaaacat ccggcaaccc ttgacgc                                         27

<210> SEQ ID NO 67
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 67
tacactcgag attaaagagg agaaattaa                                              29

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 68
ttaggatcct catactggca gcacatactt                                             30

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
caagaattct catgtttgac agct                                                   24

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 70
taactcgaga ttccctttt acgtgaac                                                28

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 71
aaaggatccc atatacagga ggagacagat                                             30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
tatggatcct taagcacccg ccacagatga                                             30
```